US009365542B2

(12) United States Patent
Balbas et al.

(10) Patent No.: US 9,365,542 B2
(45) Date of Patent: Jun. 14, 2016

(54) MODULATORS OF RESISTANT ANDROGEN RECEPTOR

(71) Applicant: MEMORIAL SLOAN-KETTERING CANCER CENTER, New York, NY (US)

(72) Inventors: Minna D. Balbas, San Francisco, NY (US); Michael J. Evans, Pacifica, NY (US); Charles L. Sawyers, New York, NY (US); Yang Shen, Chicago, IL (US); David Hosfield, Chicago, IL (US); Geoffrey L. Greene, Chicago, IL (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 14/438,584

(22) PCT Filed: Oct. 25, 2013

(86) PCT No.: PCT/US2013/066875
§ 371 (c)(1),
(2) Date: Apr. 24, 2015

(87) PCT Pub. No.: WO2014/066799
PCT Pub. Date: May 1, 2014

(65) Prior Publication Data
US 2015/0274693 A1    Oct. 1, 2015

Related U.S. Application Data

(60) Provisional application No. 61/719,117, filed on Oct. 26, 2012.

(51) Int. Cl.
*C07D 401/04* (2006.01)
*C07D 233/86* (2006.01)
*C07D 235/02* (2006.01)

(52) U.S. Cl.
CPC ............ *C07D 401/04* (2013.01); *C07D 233/86* (2013.01); *C07D 235/02* (2013.01)

(58) Field of Classification Search
None
See application file for complete search history.

(56) References Cited

U.S. PATENT DOCUMENTS

| 2007/0004753 | A1* | 1/2007 | Sawyers | ............... | C07D 233/70 514/254.05 |
|---|---|---|---|---|---|
| 2010/0172975 | A1 | 7/2010 | Sawyers et al. | | |
| 2013/0116269 | A1* | 5/2013 | Ivachtchenko | ....... | C07D 233/72 514/274 |

FOREIGN PATENT DOCUMENTS

| WO | WO-2011/106570 A1 | 9/2011 |
|---|---|---|
| WO | WO-2012/106368 A2 | 8/2012 |

OTHER PUBLICATIONS

Clegg et al., ARN-509: a novel anti-androgen for prostate cancer treatment, Cancer Research, 72(6):1494-1503 (2012).
International Search Report for PCT/US2013/066875 (5 pages) mailed Jun. 26, 2014.

* cited by examiner

*Primary Examiner* — Karl J Puttlitz
(74) *Attorney, Agent, or Firm* — Choate, Hall & Stewart LLP; Brenda Herschbach Jarrett; Michael A. Shinall

(57) ABSTRACT

The present invention provides compounds useful as modulators, agonists or antagonists of androgen receptor (AR), compositions thereof, and methods of making and using the same. Compounds of the present invention, and pharmaceutically acceptable compositions thereof, are useful in medicine, and particularly for treating any of a variety of diseases, disorders or conditions.

5 Claims, 27 Drawing Sheets

Results of an *in vitro* GFP reporter assay for 1uM and 10uM concentrations of Enzalutamide (MDV) and ARN509.

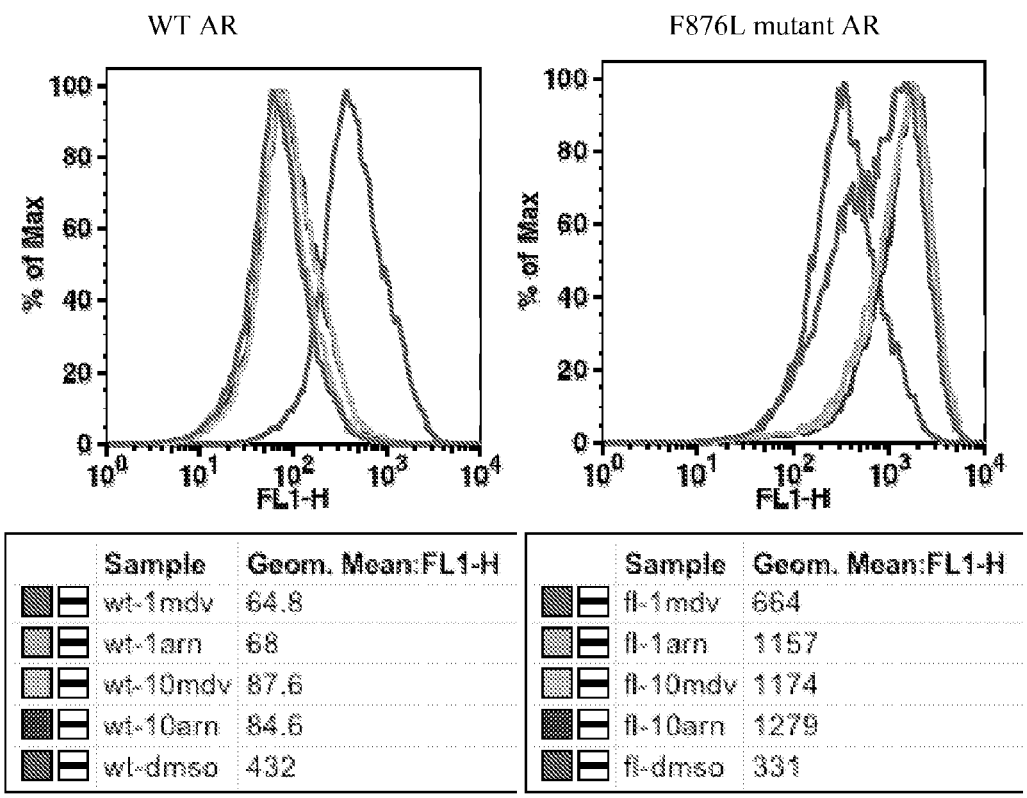
Figure 1. Results of an *in vitro* GFP reporter assay for 1uM and 10uM concentrations of Enzalutamide (MDV) and ARN509.

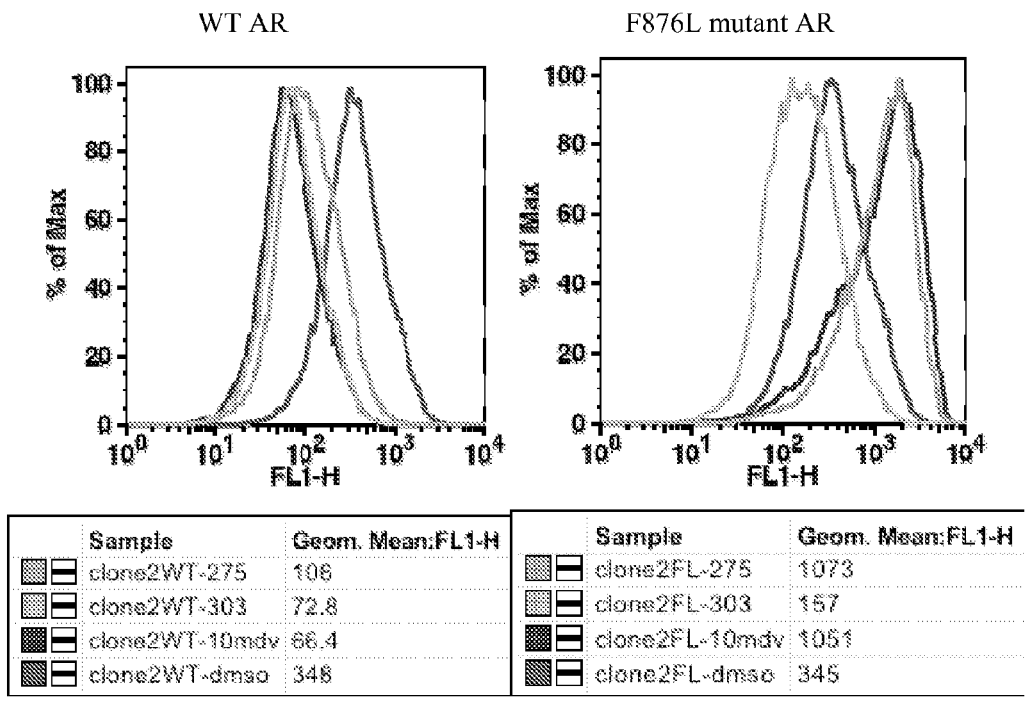
Figure 2. Results of an *in vitro* GFP reporter assay for 10uM concentrations of compounds I-9 (275) *rac* I-1, and Enzalutamide (MDV).

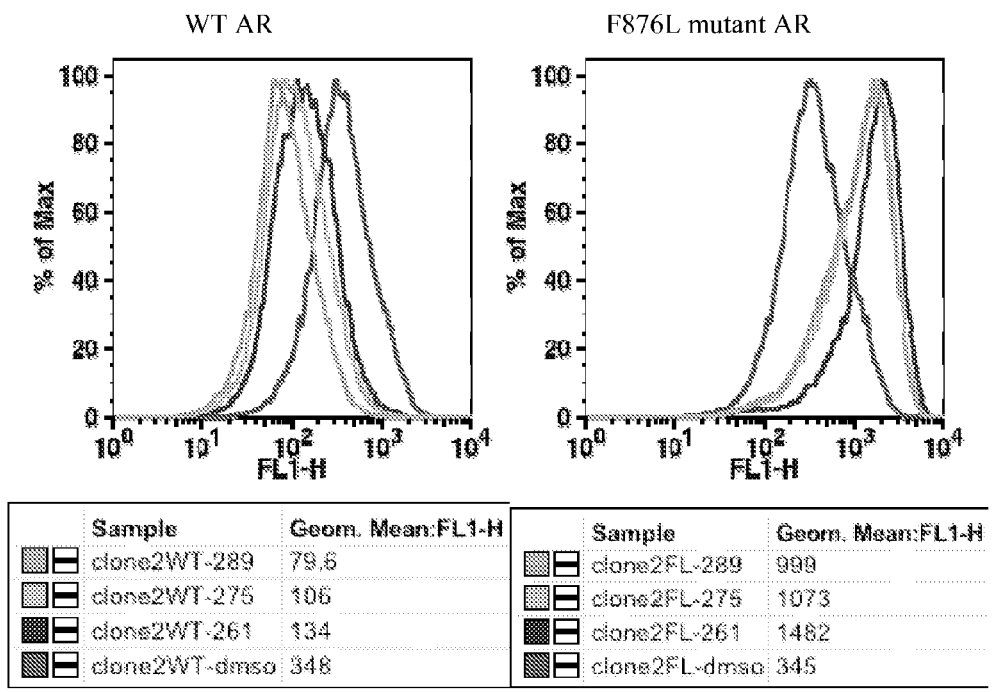
Figure 3. Results of an *in vitro* GFP reporter assay for 10uM concentrations of compounds I-10 (289), *rac* I-1 (275), and I-8 (261).

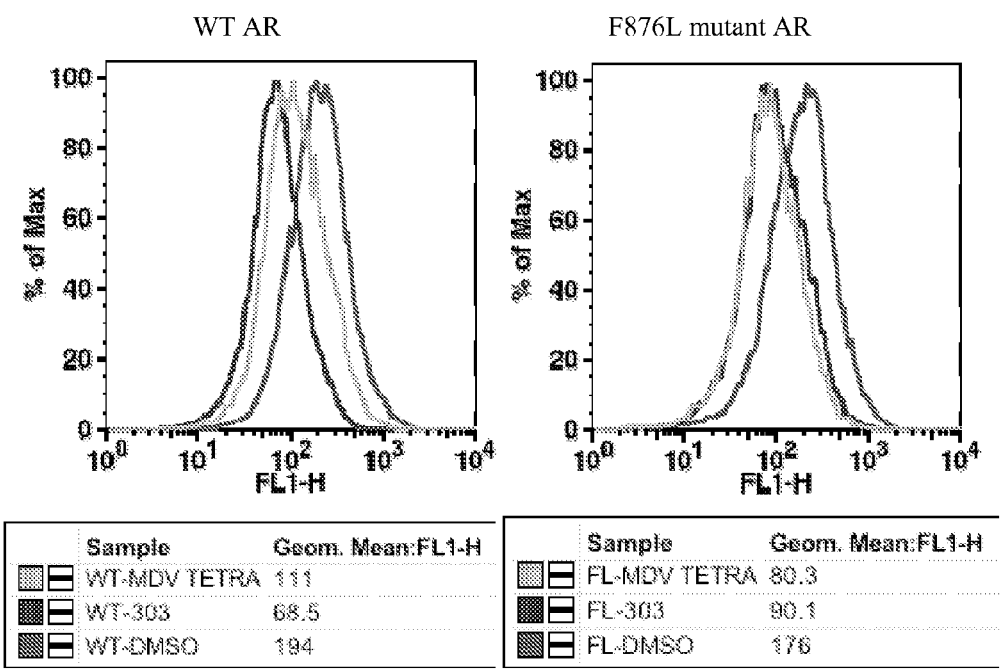
Figure 4. Results of an *in vitro* GFP reporter assay for 10uM concentrations of compounds I-5 (MDV TETRA), and *rac* I-1 (303).

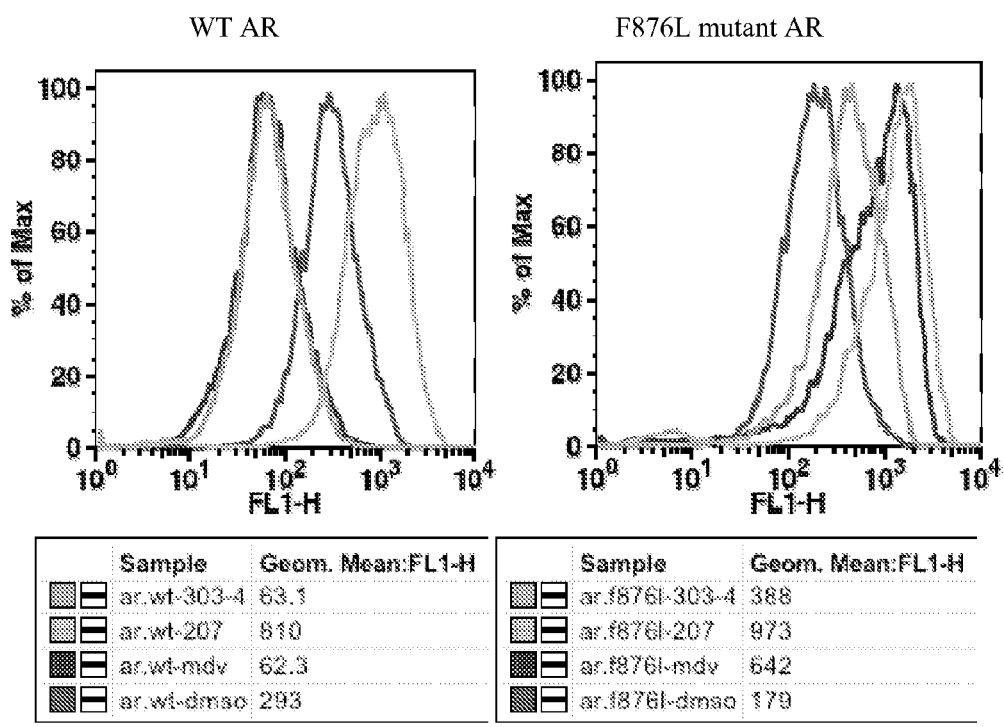
Figure 5. Results of an *in vitro* GFP reporter assay for 10uM concentrations of compounds I-26 (207), I-11 (303-4), and Enzalutamide (MDV).

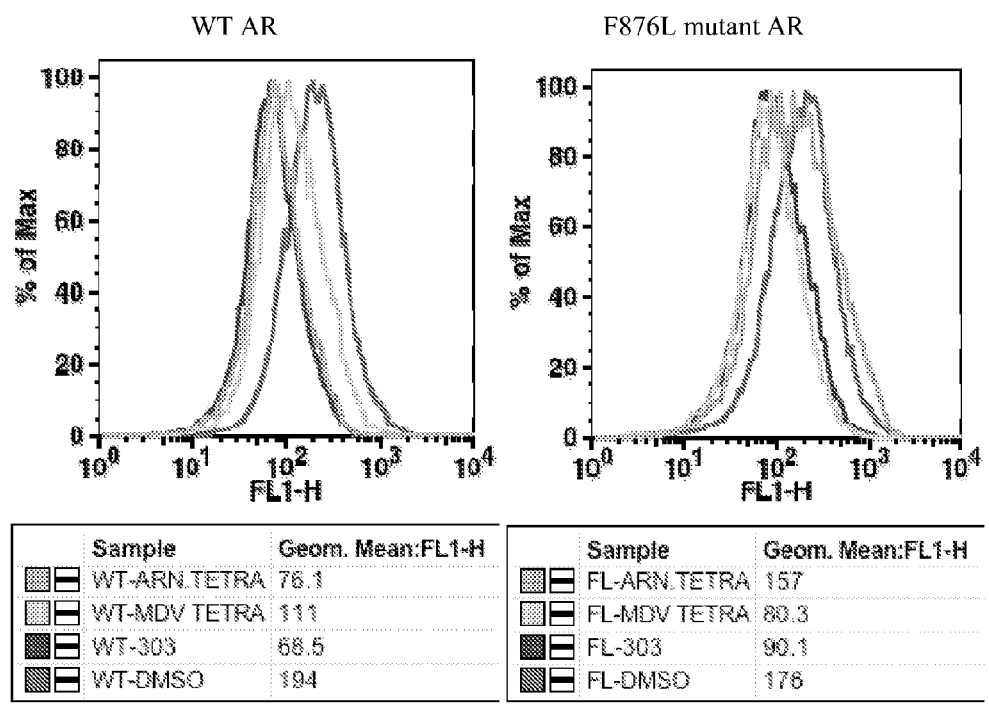
Figure 6. Results of an *in vitro* GFP reporter assay for 10uM concentrations of compounds I-5 (MDV TETRA), *rac* I-1 (303), and ARN509 (ARN.TETRA).

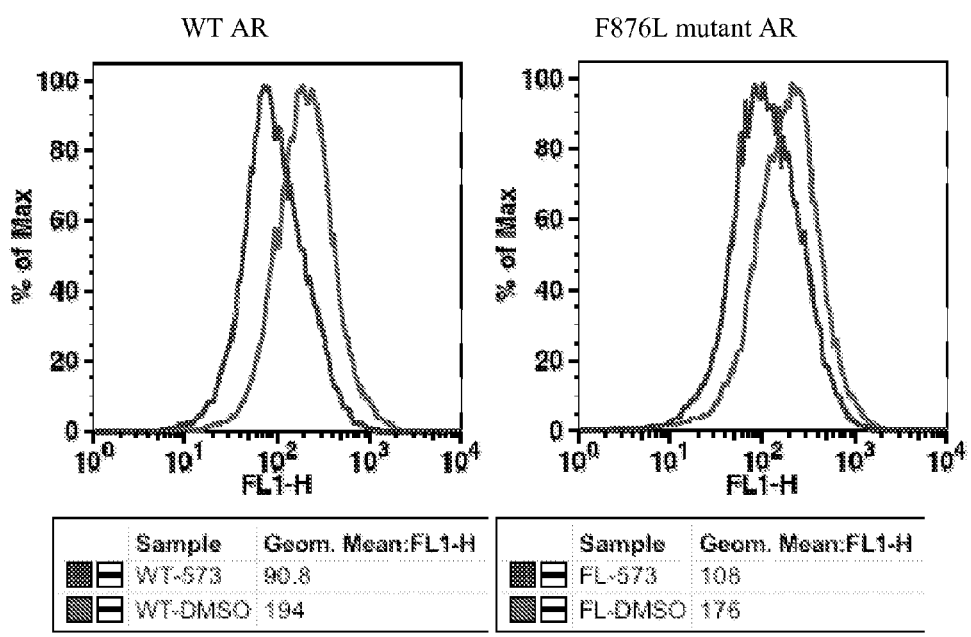
Figure 7. Results of an *in vitro* GFP reporter assay for a 10uM concentration of compound I-6 (573).

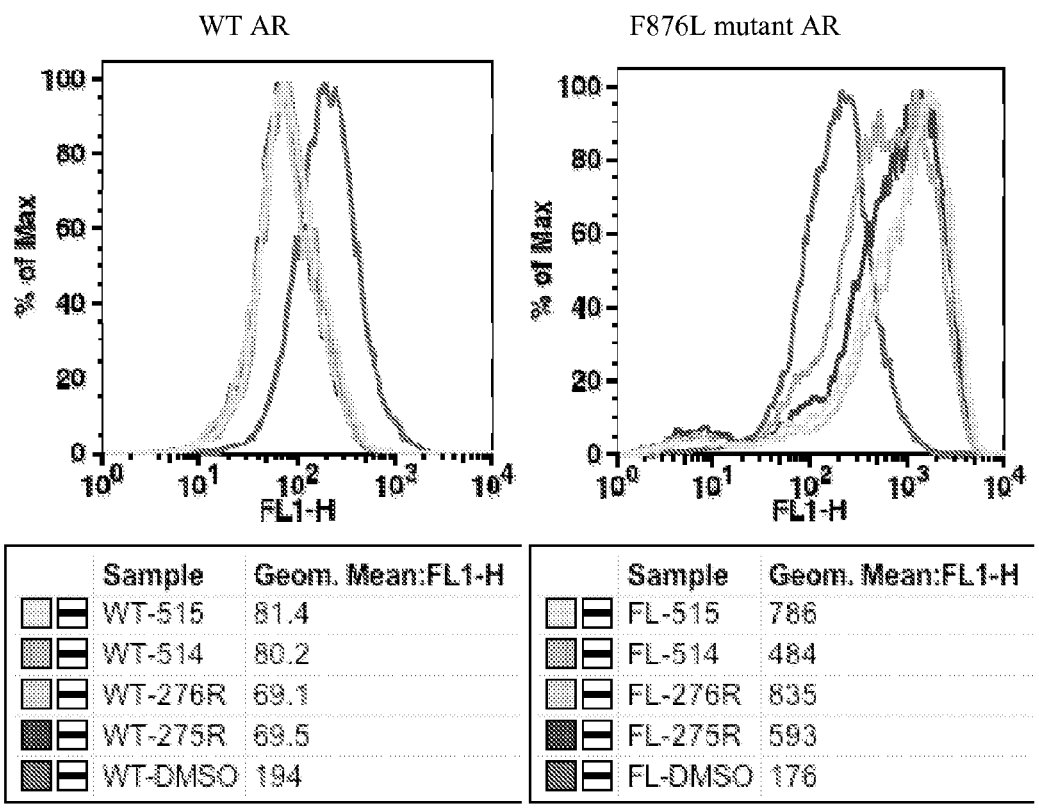
Figure 8. Results of an *in vitro* GFP reporter assay for 10uM concentrations of compounds I-21 (514), I-25 (515), I-22 (276R) and I-18 (275R).

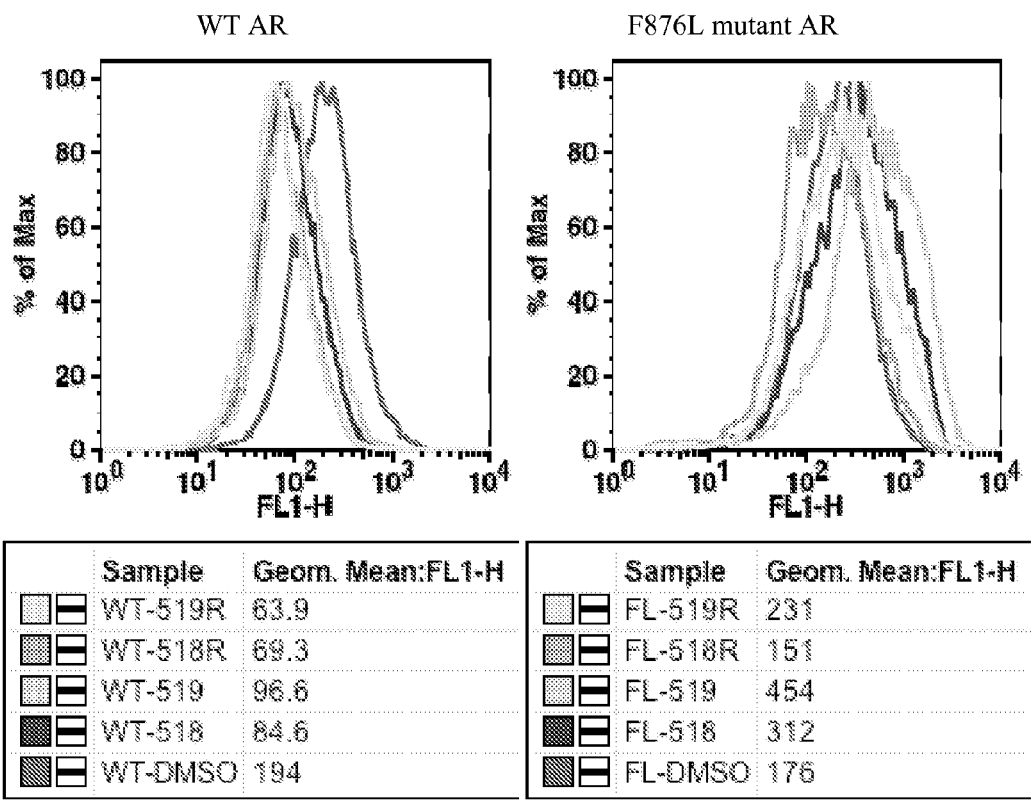
Figure 9. Results of an *in vitro* GFP reporter assay for 10uM concentrations of compounds I-23 (519), I-19 (518), I-24 (519R) and I-20 (518R).

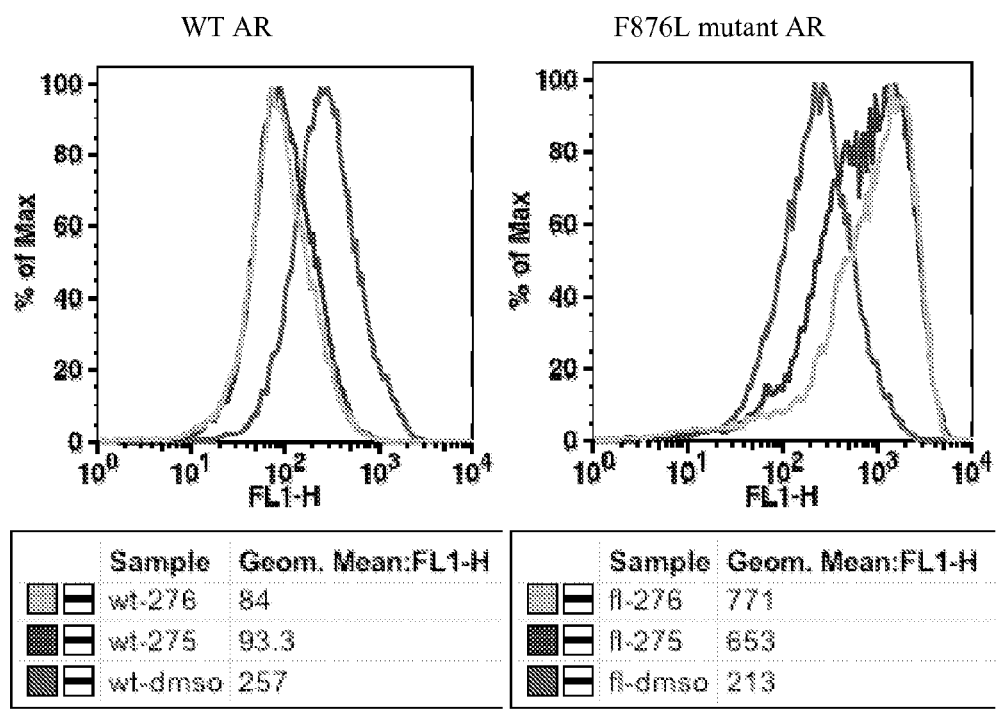
Figure 10. Results of an *in vitro* GFP reporter assay for 10uM concentrations of compounds I-9 (275) and I-14 (276).

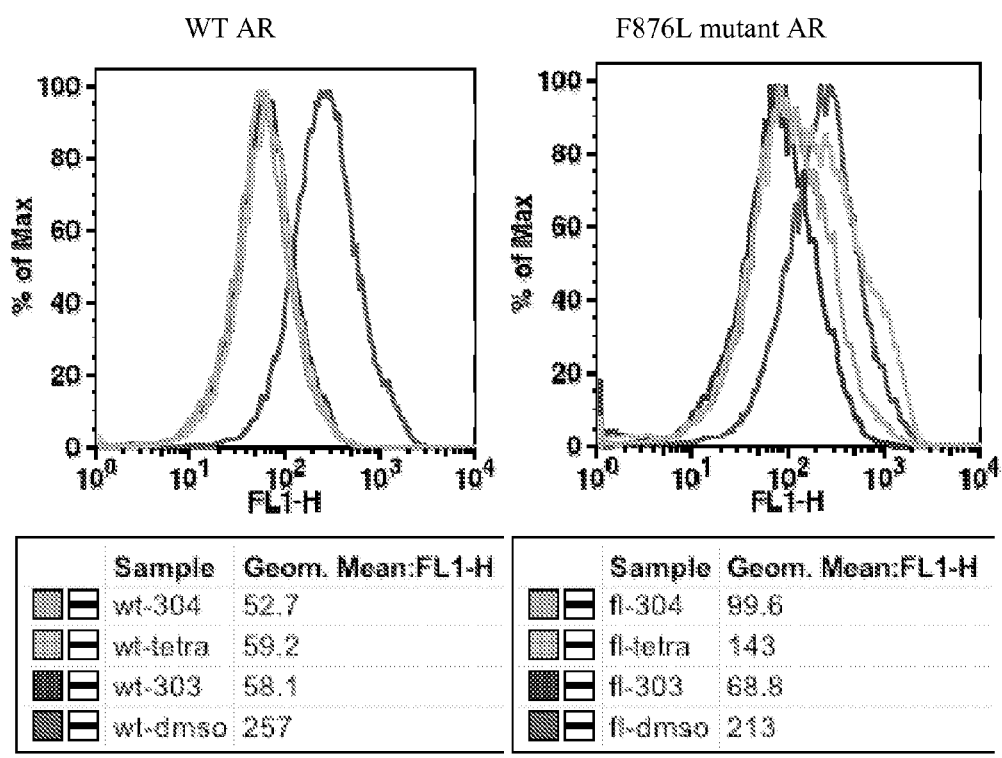
Figure 11. Results of an *in vitro* GFP reporter assay for 10uM concentrations of compounds *rac* I-1 (303), *rac* I-3 (304) and I-7 (tetra).

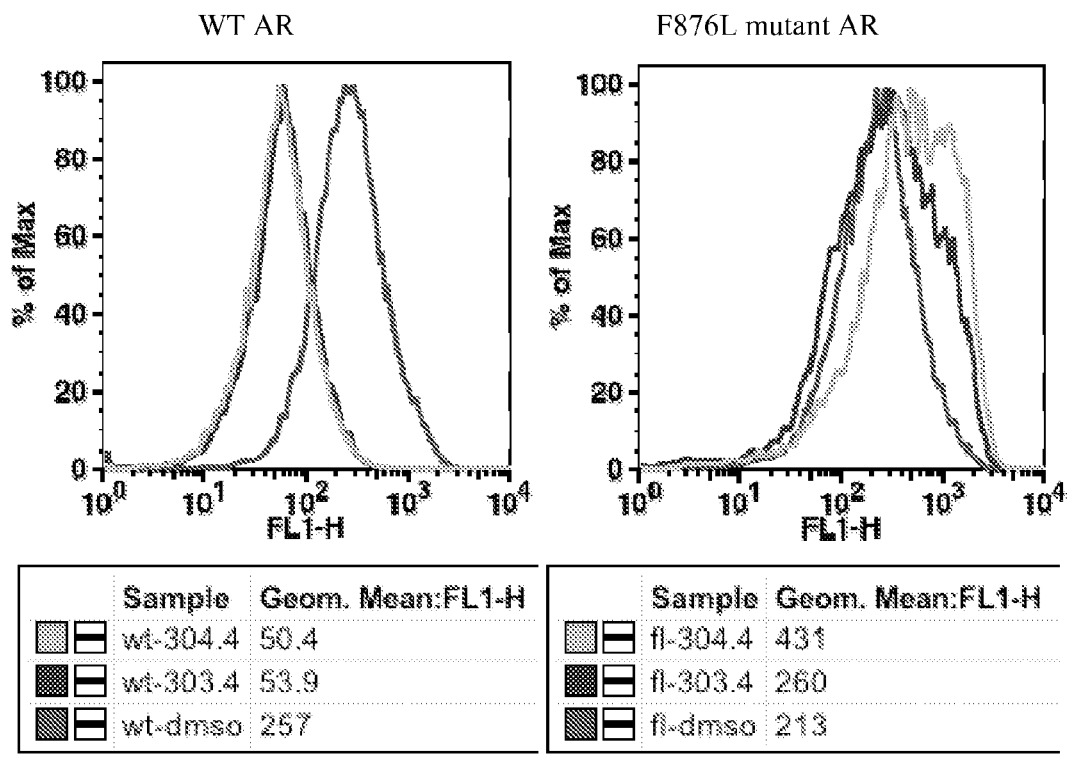
Figure 12. Results of an *in vitro* GFP reporter assay for 10uM concentrations of compounds I-11 (303.4) and I-16 (304.4).

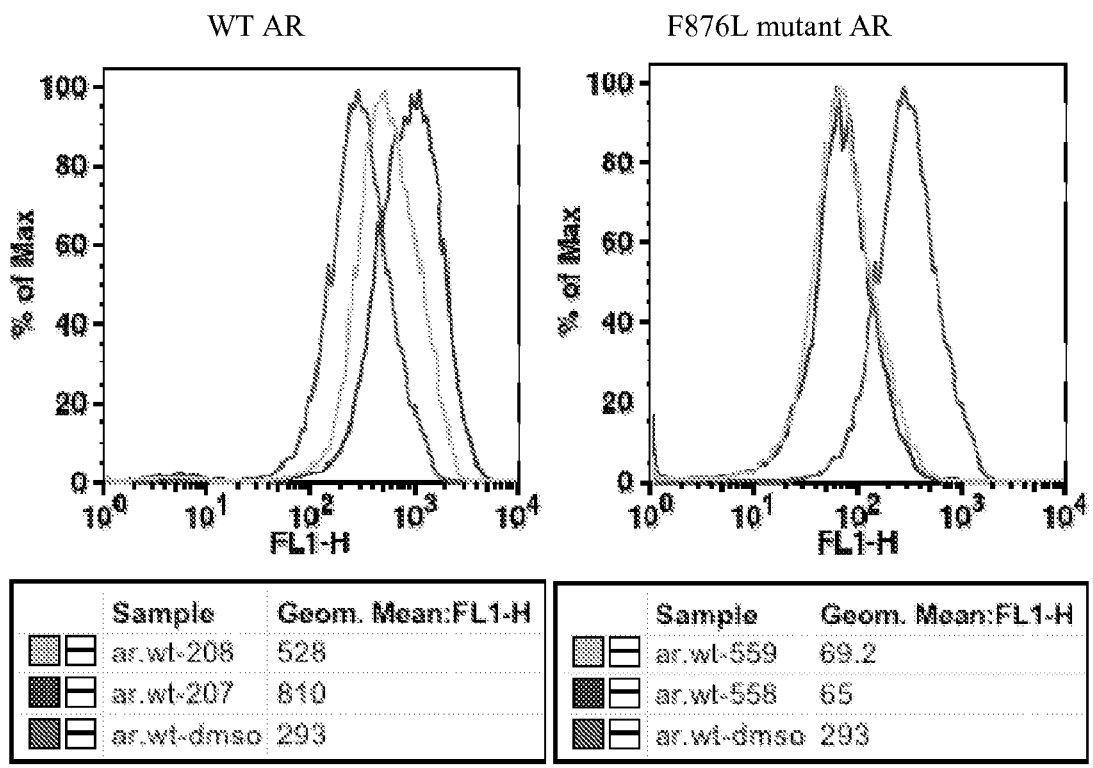
Figure 13. Results of an *in vitro* GFP reporter assay for 10uM concentrations of compounds I-27 (208) and I-26 (207).

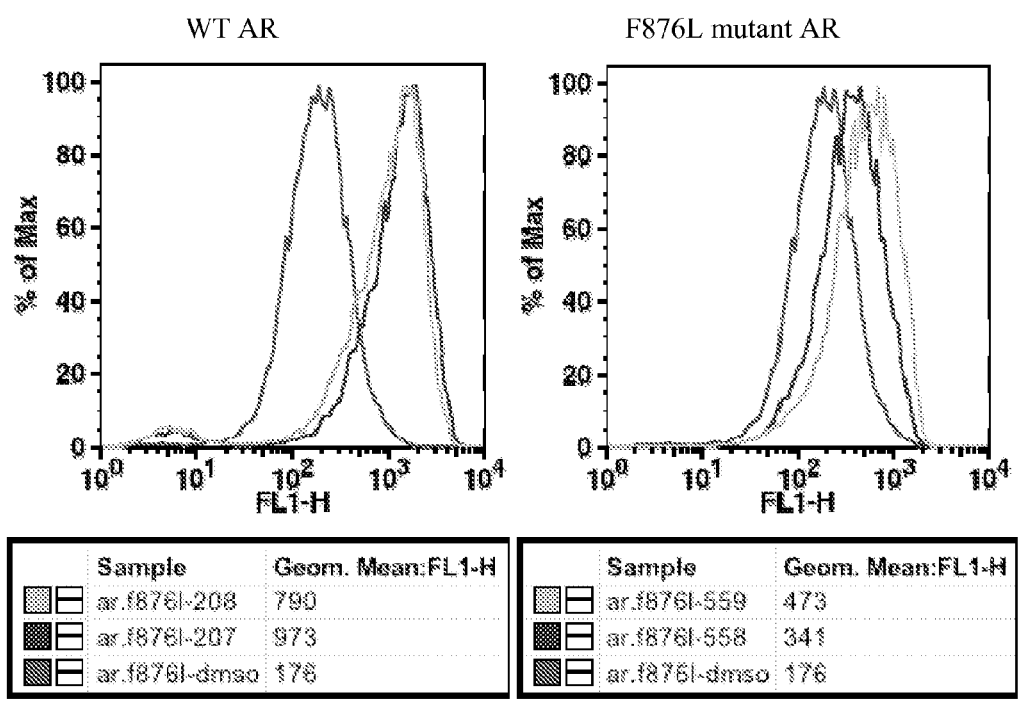
Figure 14. Results of an *in vitro* GFP reporter assay for 10uM concentrations of compounds I-17 (559) and I-12 (558).

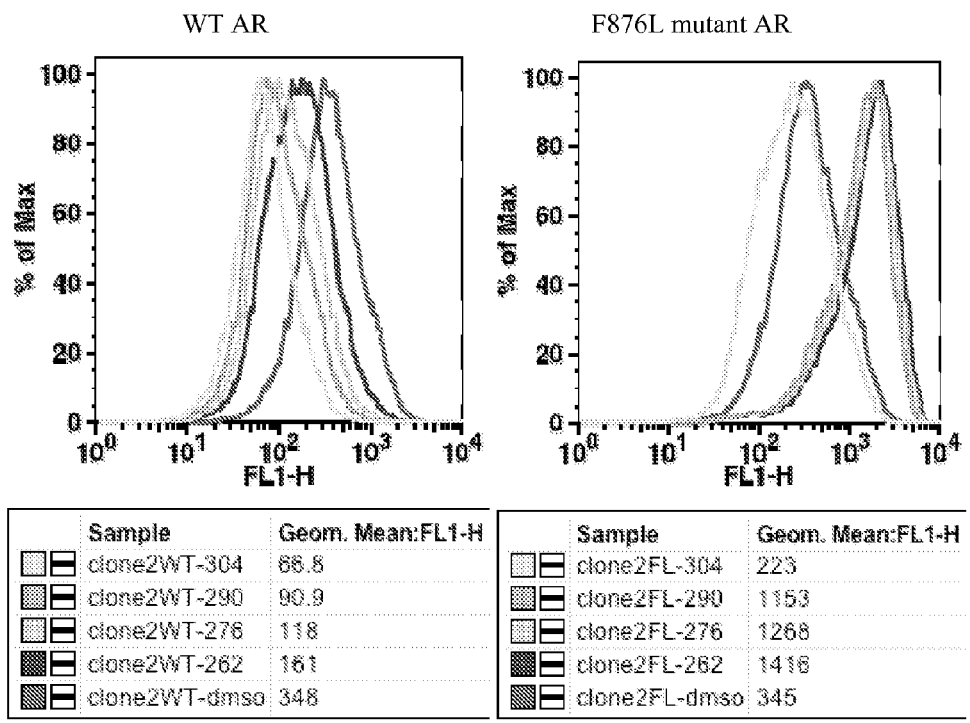
Figure 15. Results of an *in vitro* GFP reporter assay for 10uM concentrations of compounds (±)-I-3 (304), I-15 (290), I-14 (276) and I-13 (262). (±)

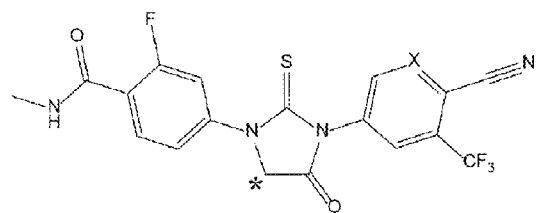

| Name | X | Substituent | WT | F876L |
|---|---|---|---|---|
| Enzalutamide | CH | (gem-dimethyl) | − | + |
| ARN-509 | N | (cyclobutyl) | − | + |
| I-8 | CH | (cyclopentyl) | − | + |
| I-9 | CH | (cyclohexyl) | − | + |
| I-10 | CH | (cycloheptyl) | − | + |
| (±)-I-1 | CH | (4-t-butylcyclohexyl) | − | − |
| I-11 | CH | (4,4-dimethylcyclohexyl) | − | + |
| I-5 | CH | (3,3,5,5-tetramethylcyclohexyl) | − | − |
| (±)-I-3 | N | (4-t-butylcyclohexyl) | − | − |
| I-26 | CH | CH₂ | + | + |

Figure 16. Results of experiments showing agonist (+) and antagonist (−) properties of compounds of formula I at both wild-type and F876L mutant AR.

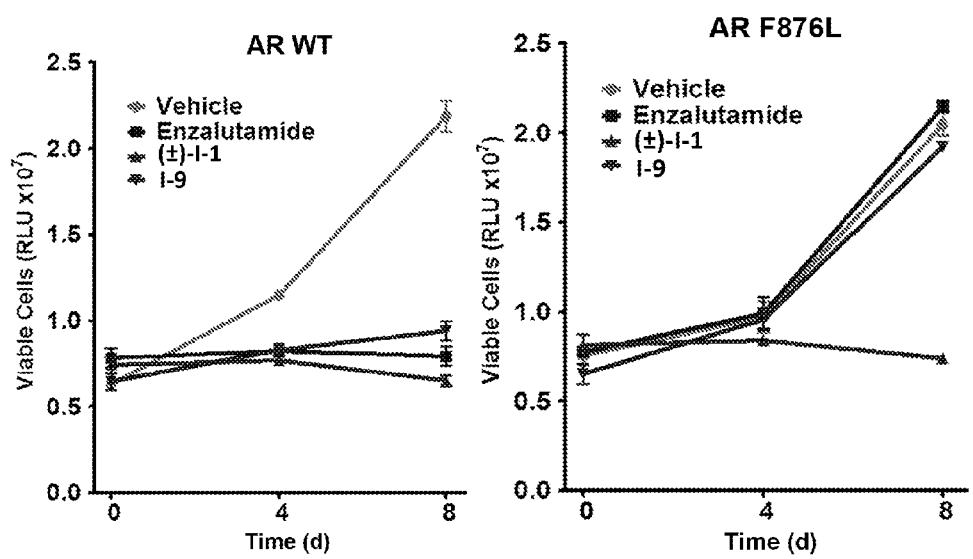
Figure 17. Results of an *in vitro* cell viability assay showing the ability of compound I-1 to kill or inhibit the growth of VCaP cells expressing either wild type or mutant F876L androgen receptor.

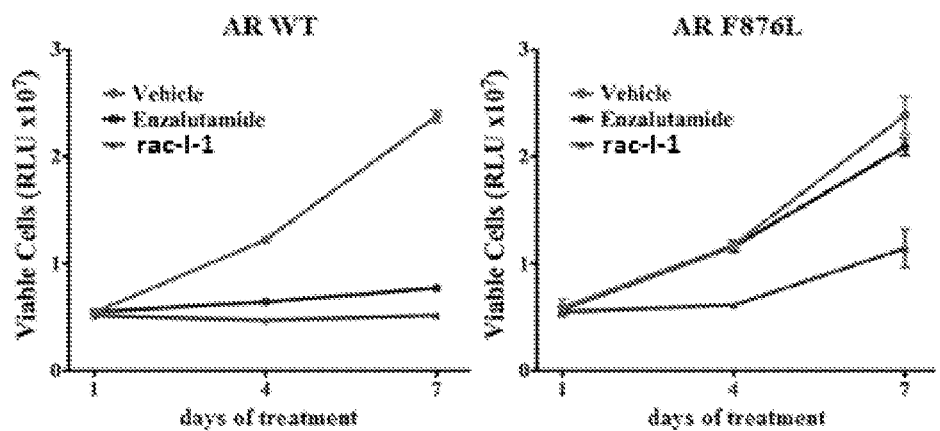
Figure 18. Results of an *in vitro* cell viability assay showing the ability of compound I-1 to kill or inhibit the growth of CWR22PC cells expressing either wild type or mutant F876L androgen receptor.

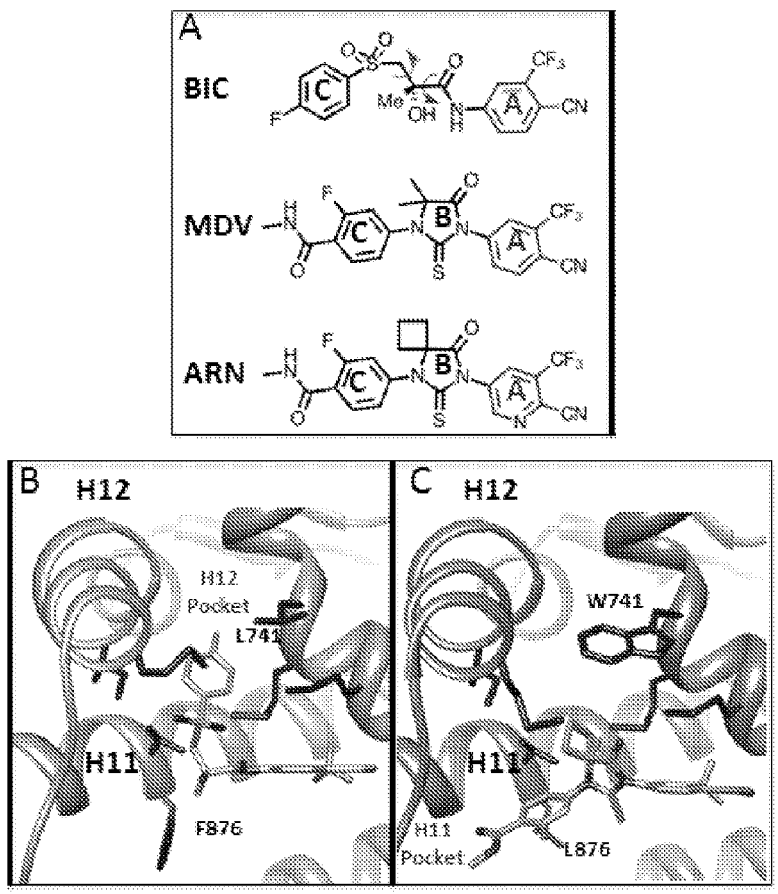

Figure 19: AR Antagonists, Crystal Structures, and Models. (A) Chemical Structures of Bicalutamide (BIC), Enzalutamide (MDV) and ARN-509 (ARN) highlighting the conserved A ring (red) and chemical similarity between MDV and ARN. The red arrows indicate torsional degrees of freedom available to BIC that permits access into the H12 pocket. (B) Crystal structure of BIC in complex with W741L AR LBD in an agonist-like conformation (rcsb ID: 1Z95) indicates interactions that facilitate C-ring penetration of the H12 pocket. (C) Initial energy-minimized models of MDV and ARN in an agonist-like conformation of F876L AR LBD (constructed using coordinates from 2AXA). The models suggest that the loss of torsional freedom imposed by the B ring of MDV and ARN imposes conformational restrictions that direct the C-ring of the antagonists towards the H11 pocket.

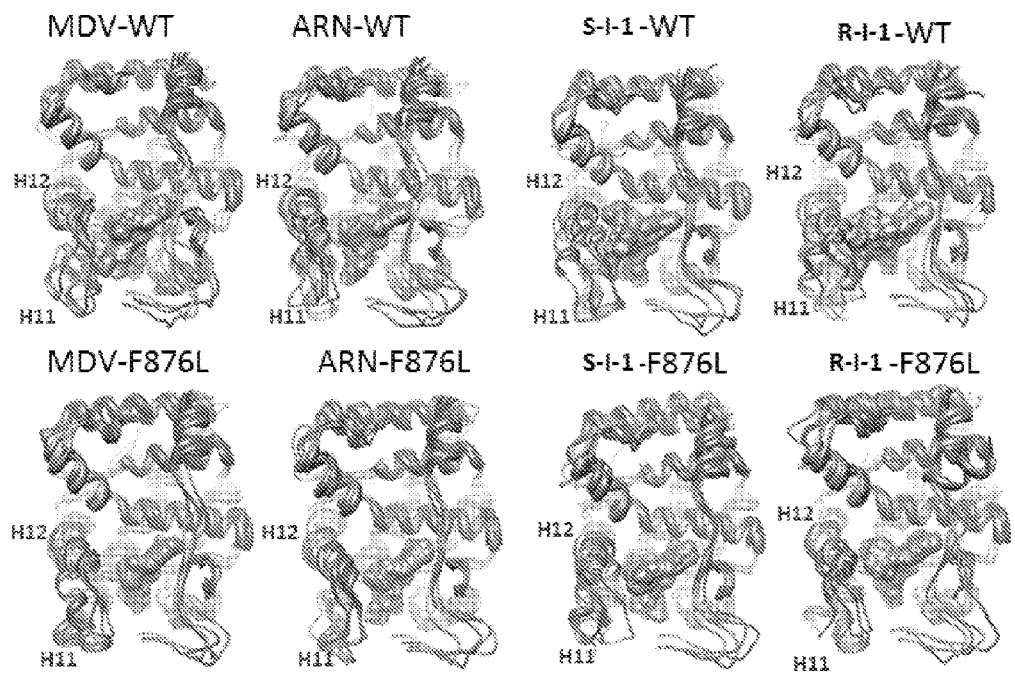

Figure 20: Molecular Dynamics Simulations of AR and ARF876L Antagonist Complexes. The coordinates for three 10-ns MD simulations with the indicated receptor (cyan) and drug compound (yellow) were overlaid on the 1Z95 structure (grey) to highlight structural differences between the agonist-like conformation AR W741L adopts in the presence of BIC. Conformational differences in the H12 position that are induced by MDV and ARN are reduced in F876L mutant, but not for (+)-(S)-I-1.

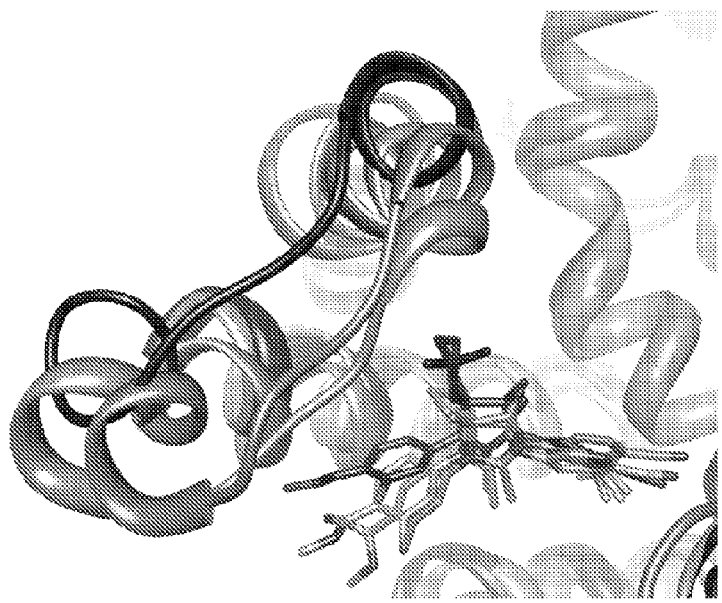
Figure 21: Comparison of AR Antagonist Models. The lowest-energy 10-ns MD models for AR F876L with MDV(cyan), ARN (yellow) and (+)-(S)-I-1 (red) were overlaid and highlight the progressive H11 and H12 displacements observed when larger substituents are appended to the thiohydantoin 3 position.

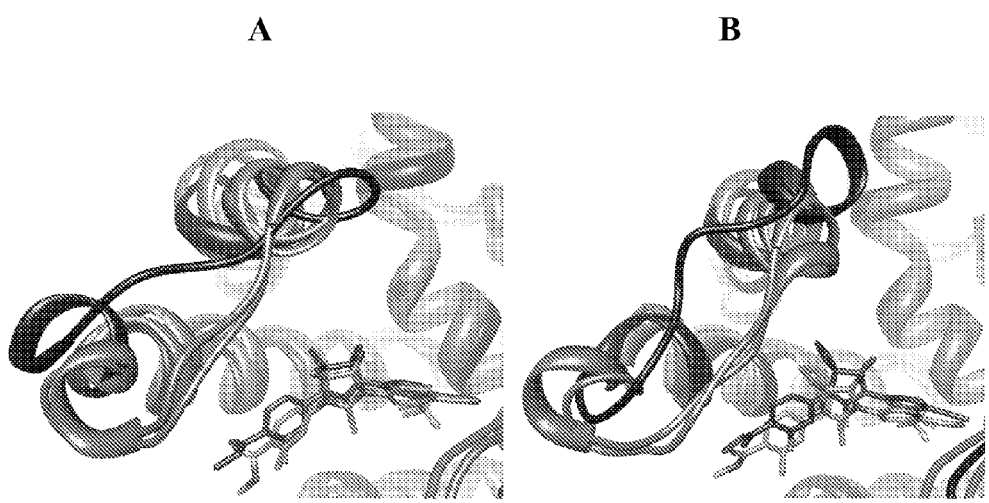

Figure 22: Comparison of AR Antagonist Models for AR WT and AR F876L. (A) The lowest-energy 10-ns MD models for MDV with WT AR (red) and F876L AR (cyan) are overlaid on 1Z95 (grey). (B) The lowest energy MD simulations for MDV with WT AR (red) and F876L AR (cyan) are overlaid on 1Z95 (grey). The simulations suggest how the F876L mutation allows the AR Ligand Binding Domain (LBD) to adopt a more agonist-like conformation of H11 and H12.

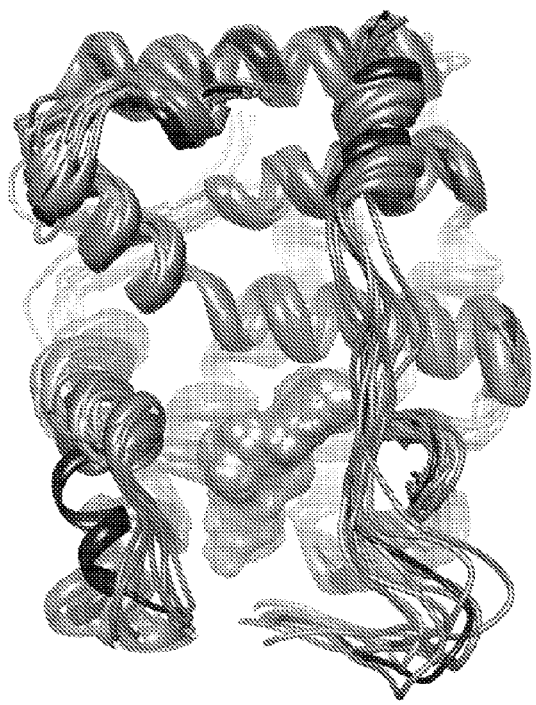
Figure 23: Extended molecular dynamics simulations of ARF876L with MDV3100. Eight 10-ns MD models with the F876L receptor (cyan) and MDV (yellow) were overlaid on the 1Z95 structure (grey) to highlight that 7 of the 8 simulations result in a typical H12 conformation that is observed in 1Z95.

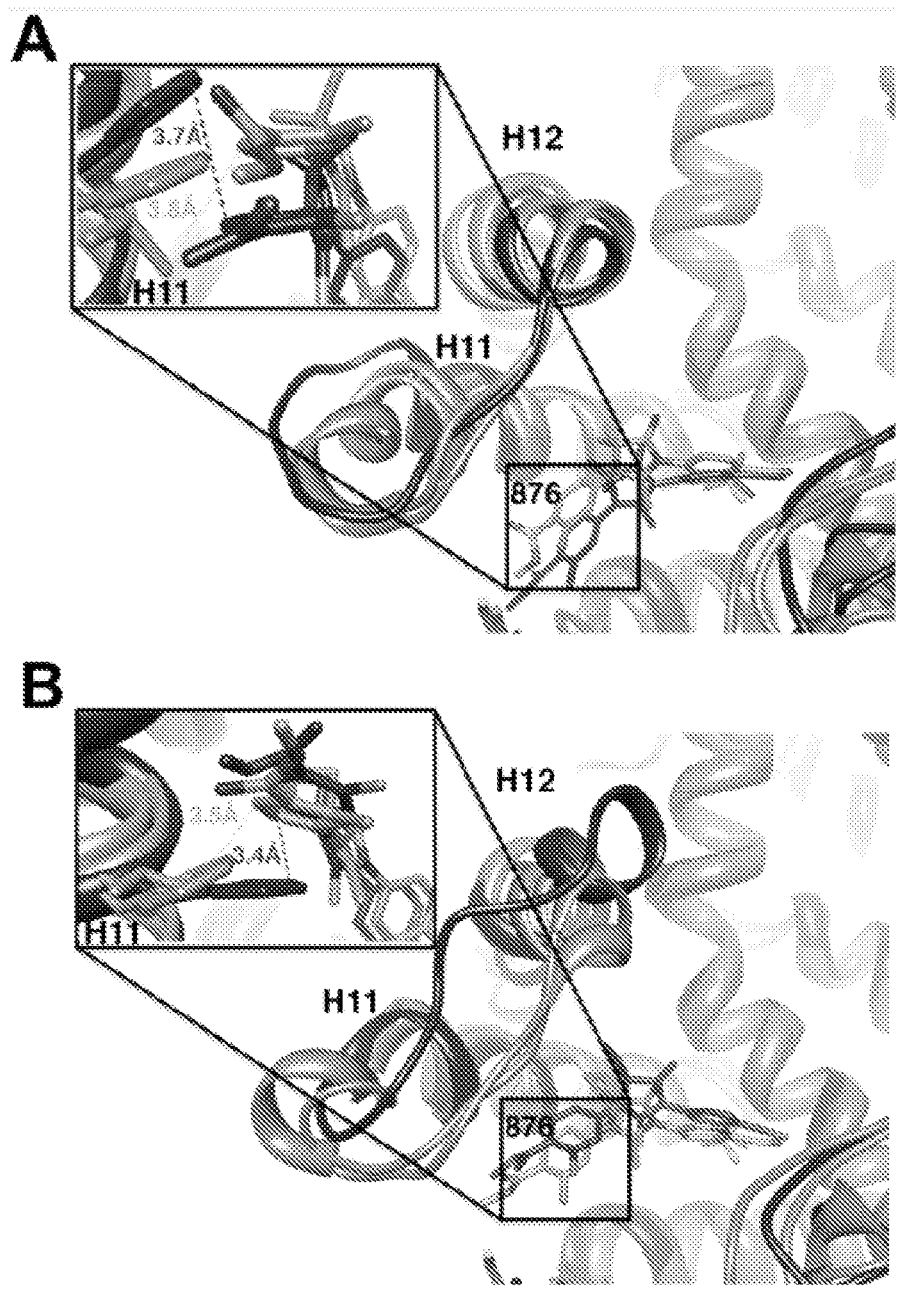
Figure 24: Zoomed in view of the H11 pocket of Figures 22A (A) and 22B (B).

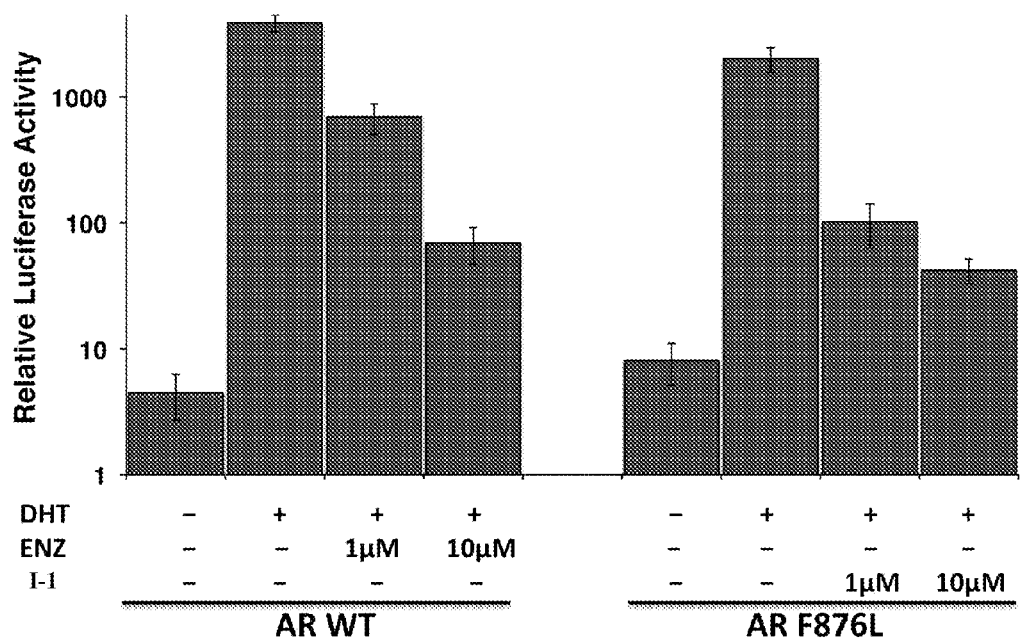
Figure 25: I-1 effectively competes with DHT for AR binding and induction of AR-regulated luciferase.

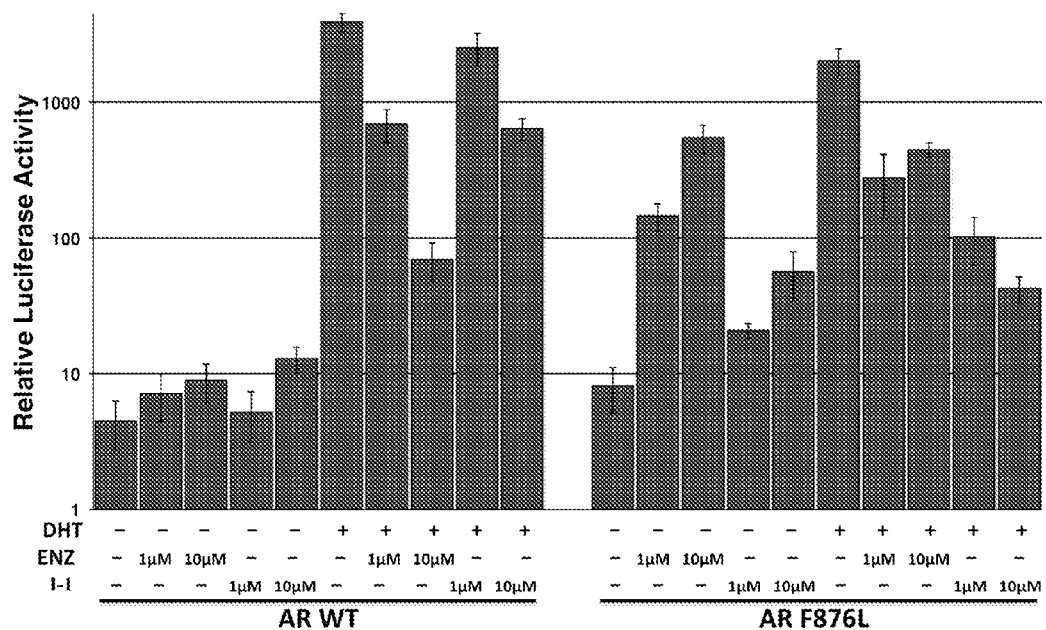
Figure 26: I-1 is a more potent agonist for AR F876L than AR WT.

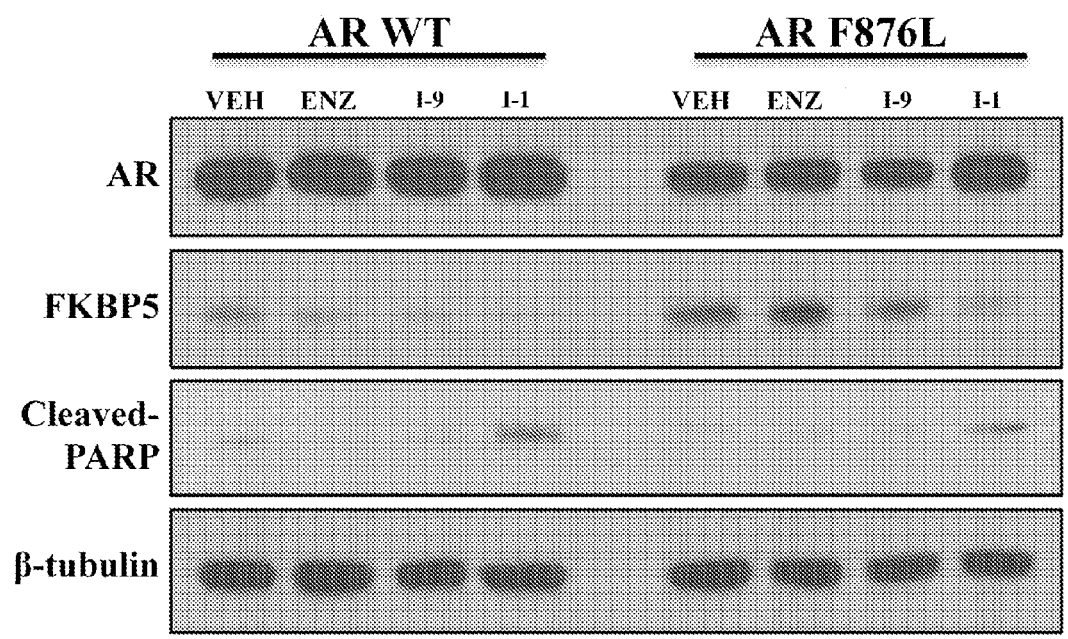
Figure 27: I-1 inhibits AR signaling and induce PARP cleavage in cells expressing both AR WT and AR F876L.

MODULATORS OF RESISTANT ANDROGEN RECEPTOR

CROSS-REFERENCE TO RELATED APPLICATIONS

The present application claims priority to U.S. provisional application Ser. No. 61/719,117, filed Oct. 26, 2012, the entirety of which is incorporated herein by reference.

BACKGROUND OF THE INVENTION

Prostate cancer is the ninth-most-common cancer in the world, but is the number-one non-skin cancer in men from the United States. As of 2011, prostate cancer is the second most frequently diagnosed cancer and the sixth leading cause of cancer death in males worldwide. In 2008, there were 186,000 new diagnoses and 28,600 deaths attributable to prostate cancer. In India in the 1990s, half of the people with prostate cancer confined to the prostate died within ten years. The continuing and highly prevalent problem of prostate cancer highlights the overwhelming need for new drugs to treat this condition and its underlying causes.

SUMMARY OF THE INVENTION

It has now been found that compounds of this invention, and pharmaceutically acceptable compositions thereof, are effective as modulators of androgen receptors (ARs). Such compounds have the general formula I:

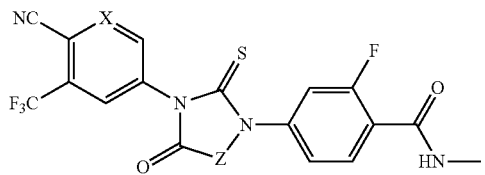

or a pharmaceutically acceptable salt thereof, wherein each variable is as defined and described herein.

Compounds of the present invention, and pharmaceutically acceptable compositions thereof, are useful in medicine, and particularly for treating any of a variety of diseases, disorders or conditions. For example, provided compounds are useful in treatment of diseases, disorders or conditions associated with ARs, and particularly with diseases, disorders or conditions associated with androgen-resistant ARs or an AR mutant associated with "castration-resistant" prostate cancer. Such diseases, disorders, or conditions include those described herein.

Compounds provided by this invention are also useful for the study of androgen receptors in biological and pathological phenomena; the study of intracellular signal transduction pathways occurring in reproductive and other bodily tissues; and the comparative evaluation of new AR modulators or treatments for AR-related diseases in vitro or in vivo.

In some embodiments, by virtue of their interaction with ARs the compounds of the present invention are useful as targeting moieties for the delivery of payloads targeting cancer cells expressing wild type or mutant androgen-resistant ARs or AR mutants associated with "castration-resistant" prostate cancer. Such uses as targeting agents for the delivery of payloads include those described herein.

BRIEF DESCRIPTION OF THE DRAWINGS

FIG. 1 presents results of an in vitro GFP reporter assay for 1 uM and 10 uM concentrations of Enzalutamide (MDV3100) and ARN509.

FIG. 2 presents results of an in vitro GFP reporter assay for 10 uM concentrations of compounds I-9, rac I-1, and Enzalutamide (MDV3100).

FIG. 3 presents results of an in vitro GFP reporter assay for 10 uM concentrations of compounds I-10, (±)-I-1, and I-8.

FIG. 4 presents results of an in vitro GFP reporter assay for 10 uM concentrations of compounds I-5, and (±)-I-1.

FIG. 5 presents results of an in vitro GFP reporter assay for 10 uM concentrations of compounds I-26, I-11, and Enzalutamide (MDV3100).

FIG. 6 presents results of an in vitro GFP reporter assay for 10 uM concentrations of compounds I-5, (±)-I-1, and ARN509.

FIG. 7 presents results of an in vitro GFP reporter assay for a 10 uM concentration of compound I-6.

FIG. 8 presents results of an in vitro GFP reporter assay for 10 uM concentrations of compounds I-21, I-25, I-22 and I-18.

FIG. 9 presents results of an in vitro GFP reporter assay for 10 uM concentrations of compounds I-23, I-19, I-24 and I-20.

FIG. 10 presents results of an in vitro GFP reporter assay for 10 uM concentrations of compounds I-9 and I-14.

FIG. 11 presents results of an in vitro GFP reporter assay for 10 uM concentrations of (±)-I-1, (±)-I-3 and I-7.

FIG. 12 presents results of an in vitro GFP reporter assay for 10 uM concentrations of compounds I-11 and I-16.

FIG. 13 presents results of an in vitro GFP reporter assay for 10 uM concentrations of compounds I-27 and I-26.

FIG. 14 presents results of an in vitro GFP reporter assay for 10 uM concentrations of compounds I-17 and I-12.

FIG. 15 presents results of an in vitro GFP reporter assay for 10 uM concentrations of compounds (±)-I-3, I-15, I-14 and I-13.

FIG. 16 presents tabulated results of GFP reporter assay experiments showing agonist (+) and antagonist (−) properties of compounds of formula I at both wild-type and F876L mutant AR.

FIG. 17 presents results of an in vitro cell viability assay showing the ability of compound I-1 to kill or inhibit the growth of VCaP cells expressing either wild type or mutant F876L androgen receptor.

FIG. 18 presents results of an in vitro cell viability assay showing the ability of compound I-1 to kill or inhibit the growth of CWR22PC cells expressing either wild type or mutant F876L androgen receptor.

FIG. 19 depicts chemical structures and ring naming for AR antagonist compounds, a crystal structure of bicalutamide bound to AR, and a molecular model of several antagonists in the AR binding pocket.

FIG. 20 depicts Molecular Dynamics Simulations of AR and ARF876L Antagonist Complexes.

FIG. 21 depicts a comparison of AR antagonist models illustrating displacements of helices H11 and H12 with a larger ring substituent on the antagonist.

FIG. 22 depicts a comparison of AR Antagonist Models for AR WT and AR F876L.

FIG. 23 depicts eight overlaid extended molecular dynamics simulations of AR F876L with MDV3100.

FIG. 24 depicts a zoomed in view of the H11 pocket of FIGS. 22A and 22B.

FIG. 25 depicts results of a luciferase reporter assay showing that I-1 effectively competes with dihydrotestosterone (DHT) for AR binding and induction of AR-regulated luciferase.

FIG. 26 depicts results of a luciferase reporter assay showing that I-1 is a more potent agonist for AR F876L than AR WT.

FIG. 27 depicts the ability of I-1 to inhibit AR signaling and induce PARP cleavage in cells expressing both AR WT and AR F876L.

DETAILED DESCRIPTION OF CERTAIN EMBODIMENTS

1. General Description of Compounds of the Invention:

In certain embodiments, the present invention provides modulators, agonists and antagonists of AR. In some embodiments, the present invention provides modulators, agonists and antagonists of androgen-resistant ARs. In some embodiments, the present invention provides modulators, agonists and antagonists of androgen-resistant AR mutants and/or AR mutants that are associated with castration-resistant prostate cancer. In some embodiments, such compounds include those of formula I:

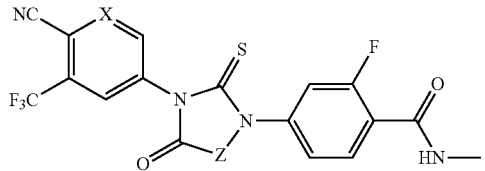

or a pharmaceutically acceptable salt thereof, wherein:

X is CH or N; and

Z is —CH$_2$— or Ring B; and

Ring B is an optionally substituted 5-14 membered saturated or partially unsaturated carbocyclic monocyclic or bicyclic ring, wherein said ring is spiro-fused at point Z.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The phrase "spiro fused at point Z", as used herein, means that when Z is Ring B, said Ring B is spiro-fused to the thiohydantoin ring of formula I in such a manner that both rings share a common tetrasubstituted carbon atom denoted Z in formula I. By way of a non-limiting example, in some embodiments when Ring B is a cyclopentane ring, compounds of formula I have the general formula:

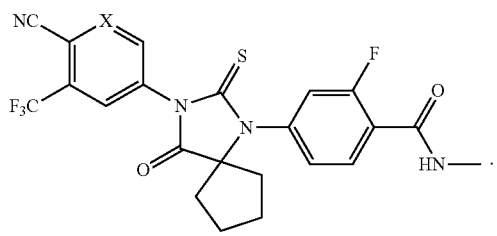

Furthermore, as a means for denoting the point of spiro fusion in the embodiments herein, specific examples of Ring B shall be understood to be fused to the thiohydantoin ring at the carbon atom denoted Z. Thus, as a non-limiting example, when it is desired to communicate that Ring B is a 4,4-dimethylcyclohexane ring fused to the thiohydantoin ring through position 1 of the cyclohexane ring, such a ring can be depicted in the following manner:

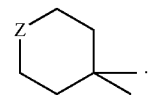

Alternatively, the point of attachment on each of the spiro-fused rings can be denoted by asterisks in the following manner:

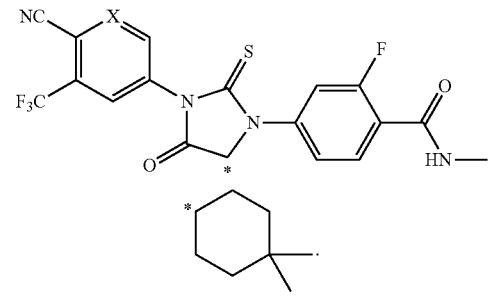

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C$_3$-C$_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

As used herein, the term "androgen" is used herein to refer to agents androgenic activity. Androgenic activity may be determined or characterized in any of a variety of ways, including in any of a variety of biological activity assays (e.g., in vitro or in vivo assays, for example utilizing animals and/or animal tissues) in which the agent is observed to have one or more activities similar or comparable to that of a known androgen assessed under comparable conditions (whether simultaneously or otherwise). In some embodiments, androgenic activity is or comprises transcriptional regulation (e.g., activation) of an androgen-responsive target gene. In some embodiments, androgenic activity is or comprises stimulation of prostate growth in rodents. Exemplary know androgens include, for example, androstanedione, androstenediol, androstenedione, androsterone, dehydroepiandrosterone, dehydroepiandrosterone sulfate, dihydrotestosterone (DHT), and testosterone.

As used herein, the term "antiandrogen" refers to any agent that inhibits biological activity of androgens. In some embodiments, antiandrogens inhibit biological activity of an AR. In some embodiments antiandrogens inhibit biological activity of a wild type AR. In some embodiments, antiandrogens inhibit biological activity of one or more AR included in Table A. In some embodiments, antiandrogens compete with one or more androgens for binding to an AR. In some embodiments, antiandrogens compete with one or more androgens for binding to a wild type AR. In some embodiments, antiandrgens compete with one or more androgens for binding to an AR included in Table A. In some embodiments, antiandrogens comprise 3,3'-diindolylmethane (DIM), ARN-509, bexlosteride, bicalutamide, N-butylbenzene-sulfonamide (NBBS), dutasteride, epristeride, enzalutamide, finasteride, flutamide, izonsteride, ketoconazole, N-butylbenzene-sulfonamide, nilutamide, megestrol, steroidal antiandrogens, and/or turosteride.

As used herein, the term "associated with" means correlated with or statistically likely to occur or appear together with another state, or condition. In some embodiments, the term "associated with" refers to statistically non-random or correlated events. In some embodiments, the term "associated with" refers to a physical association in three-dimensional space. In some such embodiments, such physical association is mediated by one or more covalent or non-covalent (e.g., hydrogen bonds, hydrophobic interactions, van der Waals interactions, electrostatic forces, magnetic forces, pi-pi interactions, sigma-pi interactions, etc.).

As used herein, the terms "correlates" or "correlated", as used herein, has its ordinary meaning of "showing a correlation with". Those of ordinary skill in the art will appreciate that two features, items or values show a correlation with one another if they show a tendency to appear and/or to vary, together. In some embodiments, a correlation is statistically significant when its p-value is less than 0.05; in some embodiments, a correlation is statistically significant when its p-value is less than 0.01. In some embodiments, correlation is assessed by regression analysis. In some embodiments, a correlation is a correlation coefficient.

As used herein, the term "corresponding to" is often used to designate the position/identity of a particular residue within a polymeric agent (e.g., within a nucleic acid or polypeptide). Those of ordinary skill will appreciate that, for purposes of simplicity, a canonical numbering system (based on a reference polymer) is often utilized herein in order to facilitate comparison of polymer sequences. Those of ordinary skill in the art understand how to align polymer sequences in order to determine which residues "correspond" to particular positions in a reference polymer. For example, those skilled in the art appreciate that a particular residue in a polypeptide of interest may "correspond to" a residue at a certain position in a reference polypeptide even if it is not found at the same position (relative to a terminus of the polypeptide) in the polypeptide of interest, so long as its context in the polypeptide of interest is sufficiently similar to that of the residue in the polypeptide of interest that it would be recognized by one skilled in the art as "corresponding to" that reference residue.

As used herein, a "detection moiety" in the context of provided multifunctional agents refers to a molecular structure or module that allows visualization/imaging, measurements (localization, quantification, etc.) and/or monitoring of an agent in vitro and/or in vivo using one or more detection techniques including but not limited to spectroscopic, photochemical, biochemical, immunochemical, electrical, optical, chemical or other means.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

As used herein, the terms "improve," "increase" or "reduce," or grammatical equivalents, indicate a change in a value relative to a comparable baseline or reference measurement. In some embodiments, a comparable baseline or reference measurement is a measurement taken in the same system (e.g., of the same individual) prior to initiation of an event of interest (e.g., of therapy). In some embodiments, a comparable baseline or reference measurement is one taken in a different system (e.g., a different individual or cell) under otherwise identical conditions (e.g., in a normal cell or individual as compared with one suffering from or susceptible to a particular disease, disorder or condition, for example due to presence of a particular genetic mutation).

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

As used herein, the term "mutant" refers to an altered (as compared with a reference) nucleic acid or polypeptide, or to a cell or organism containing or expressing such an altered nucleic acid or polypeptide.

The term "polypeptide" or "peptide", as used herein, generally has its art-recognized meaning of a polymer of at least three amino acids. Those of ordinary skill in the art will appreciate that the term "polypeptide" is intended to be sufficiently general as to encompass not only polypeptides having the a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein.

The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" may be used to refers to the multiple polypeptides that are physically associated coupled and function together as the discrete unit.

As will be understood from context, a reference sequence, sample, population, agent or individual is one that is sufficiently similar to a particular sequence, sample, population, agent or individual of interest to permit a relevant comparison (i.e., to be comparable). In some embodiments, information about a reference sample is obtained simultaneously with information about a particular sample. In some embodiments, information about a reference sample is historical. In some embodiments, information about a reference sample is stored for example in a computer-readable medium. In some embodiments, comparison of a particular sample of interest with a reference sample establishes identity with, similarity to, or difference of a particular sample of interest relative to a reference.

As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

As used herein, a "targeting moiety" in the context of provided multifunctional agents refers to a molecular structure or module that affects or controls the site of action by specifically interacting with, or has affinity for, a target of interest. In some embodiments, a targeting moiety useful for the present invention is a compound of formula I.

As used herein, a "therapeutic moiety" in the context of provided multifunctional agents refers to a molecular structure or module that confers a therapeutic effect. In some embodiments, therapeutic effects conferred by a therapeutic moiety of a multifunctional agent of the present invention include anti-cancer effects. Accordingly, a therapeutic moiety may be an anti-cancer agent (e.g., chemotherapeutic agent). In some embodiments, anti-cancer agents useful for the present invention are agents that inhibit tumor growth, agents that inhibit proliferation of cancer cells, agents that preferentially kill cancer cells, agents that inhibit angiogenesis, etc. In some embodiments, such agents are small molecules. Small molecules include, without limitation, small chemical-based entities, such as chemotoxins and cytostatic drugs, which may be referred to as "SCEs." Typically, SCEs are non-peptide, non-nucleic acid molecules. In those embodiments that include both a therapeutic entity and a diagnostic entity, the therapeutic entity and the target entity are not the same entity.

As used herein, the term "therapeutically effective amount" refers to an amount of an agent which confers a therapeutic effect on a treated subject, at a reasonable benefit/risk ratio applicable to any medical treatment. A therapeutic effect may be objective (i.e., measurable by some test or marker) or subjective (i.e., subject gives an indication of or feels an effect). In particular, a "therapeutically effective amount" refers to an amount of a therapeutic agent effective to treat, ameliorate, or prevent a desired disease or condition, or to exhibit a detectable therapeutic or preventative effect, such as by ameliorating symptoms associated with a disease, preventing or delaying onset of a disease, and/or also lessening severity or frequency of symptoms of a disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other agents. Also, a specific therapeutically effective amount (and/or unit dose) for any particular patient may depend upon a variety of factors including what disorder is being treated; disorder severity; activity of specific agents employed; specific composition employed; age, body weight, general health, and diet of a patient; time of administration, route of administration; treatment duration; and like factors as is well known in the medical arts.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

The term "unsaturated," as used herein, means that a moiety has one or more units of unsaturation.

As used herein, the term "wild-type" refers to a typical or common form existing in nature; in some embodiments it is the most common form.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

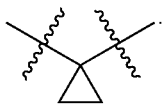 [SMILES: *C1(*)CC1]

As used herein, the term "cyclobutylenyl" refers to a bivalent cyclobutyl group of the following structure:

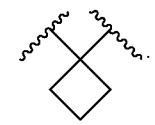 [SMILES: *C1(*)CCC1]

As used herein, the term "oxetanyl" refers to a bivalent oxetanyl group of the following structure:

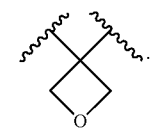

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(halo R$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Those skilled in the art will appreciate that some structures provided herein represent compounds that can exist in a plurality of isomeric (e.g., enantiomeric, diastereomeric, and geometric (or conformational)) forms; for example, the R and S configurations for each asymmetric center, Z and E double bond isomers, and Z and E conformational isomers. Single such isomers or forms (e.g. stereochemical isomers [e.g., enantiomeric, diastereomeric, etc.] and/or geometric (or conformational) isomers), as well as combinations or mixtures of such forms are within the scope of the invention. Similarly, all tautomeric forms of the compounds of the invention are within the scope of the invention. Additionally, those skilled in the art will appreciate that analogs of compounds having depicted structures that vary from the depicted compound only in the presence of one or more isotopically enriched atoms may readily be prepared; such "isotopic isomers" of provided compounds are also within the scope of the present invention, and may be provided individually or together with one or more other forms of the compound. For example, compounds having depicted structures wherein one or more hydrogen atoms has/have been replaced by deuterium and/or tritium, one or more carbon atoms has/have been replaced by a $^{13}C$- or $^{14}C$-enriched carbon are within the scope of this invention. Such isotopic isomers are useful, for example, as analytical tools, as probes in biological assays, or as therapeutic agents in accordance with the present invention.

3. Description of Exemplary Embodiments:

Androgen Receptor

The androgen receptor (AR), located on Xql 1-12, is a 110 kD nuclear receptor that, upon activation by androgens, mediates transcription of target genes that modulate growth and differentiation of prostate epithelial cells. Similar to other steroid receptors, unbound AR is mainly located in cytoplasm and associated with a complex of heat shock proteins (HSPs) through interactions with its ligand-binding domain. Upon agonist binding, AR undergoes a series of conformational changes: heat shock proteins dissociate from AR, and transformed AR undergoes dimerization, phosphorylation, and nuclear translocation, which is mediated by its nuclear localization signal. Translocated receptors then binds to androgen response elements (ARE), which are characterized by a six-nucleotide half-site consensus sequence 5'-TGTTCT-3' spaced by three random nucleotides and are located in promoter or enhancer regions of AR gene targets. Recruitment of other transcription co-regulators (including co-activators and co-repressors) and transcriptional machinery further ensures transactivation of AR-regulated gene expression. All of these processes are initiated by the ligand-induced conformational changes in the ligand-binding domain.

As used herein, "Androgen-dependent disorder" refers to any disorder that can benefit from a decrease in androgen stimulation and includes pathological conditions that depend on androgen stimulation. An "androgen-dependent disorder" can result from an excessive accumulation of testosterone or other androgenic hormone, increased sensitivity of androgen receptors to androgen, or an increase in androgen-stimulated transcription. Examples of "androgen-dependent disorders" include prostate cancer and skin disorders such as, for example, acne, seborrhea, hirsutism, alopecia, or hidradenitis suppurativa.

Prostate Cancer

Prostate cancer is the second most common cause of cancer death in men in the US, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites.

AR signaling is crucial for development and maintenance of male reproductive organs including prostate glands, as genetic males harboring loss of function AR mutations and mice engineered with AR defects do not develop prostates or prostate cancer. This dependence of prostate cells on AR signaling continues even upon neoplastic transformation.

Given that prostate cancer cells depend on AR for their proliferation and survival, these men are treated with agents that block production of testosterone (e.g. GnRH agonists), alone or in combination with antiandrogens, which antagonize effects of any residual testosterone. This approach is effective as evidenced by a drop in PSA and regression of any visible tumor.

Castration Resistant Prostate Cancer

This hormone-refractory state to which most patients eventually progresses in the presence of continued androgen ablation or anti-androgen therapy is known as "castration resistant" prostate cancer (CRPC).

Compelling data demonstrate that AR is expressed in most prostate cancer cells and overexpression of AR is necessary and sufficient for androgen-independent growth of prostate cancer cells. Failure in hormonal therapy, resulting from development of androgen-independent growth, is an obstacle for successful management of advanced prostate cancer. Instances of antiandrogen withdrawal syndrome have also been reported after prolonged treatment with antiandrogens. Antiandrogen withdrawal syndrome is commonly observed clinically and is defined in terms of tumor regression or symptomatic relief observed upon cessation of antiandrogen therapy. AR mutations that result in receptor promiscuity and the ability of these antiandrogens to exhibit agonist activity might at least partially account for this phenomenon. For example, hydroxyflutamide and bicalutamide act as AR agonists in T8787A, W741L and W741C AR mutants, respectively.

Treatment options for CPRC are an unmet need. Until recently, docetaxel was the only agent shown to prolong survival. More recently, four newer treatments have come onto the market, including sipuleucel-T, an immunotherapeutic agent; cabazitaxel, a novel microtubule inhibitor; abiraterone acetate, a new androgen biosynthesis inhibitor; and denosumab. Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

In certain embodiments, the present invention provides modulators, agonists, and antagonists of AR. In some such embodiments, the AR is an androgen-resistant AR or an AR mutant associated with castration-resistant prostate cancer. In some embodiments, the AR has an amino acid sequence as set forth in Table A.

TABLE A

| | |
|---|---|
| Human AR Protein Sequence (Swiss-Prot: P10275.2) | MEVQLGLGRVYPRPPSKTYRGAFQNLFQSVREVIQNPGPRHPEA ASAAPPGASLLLLQQQQQQQQQQQQQQQQQQQQQETSPRQQQ QQQGEDGSPQAHRRGPTGYLVLDEEQQPSQPQSALECHPERGC VPEPGAAVAASKGLPQQLPAPPDEDDSAAPSTLSLLGPTFPGLSS CSADLKDILSEASTMQLLQQQQQEAVSEGSSSGRAREASGAPTS SKDNYLGGTSTISDNAKELCKAVSVSMGLGVEALEHLSPGEQLR GDCMYAPLLGVPPAVRPTPCAPLAECKGSLLDDSAGKSTEDTAE YSPFKGGYTKGLEGESLGCSGSAAAGSSGTLELPSTLSLYKSGAL DEAAAYQSRDYYNFPLALAGPPPPPPPPHPHARIKLENPLDYGSA WAAAAAQCRYGDLASLHGAGAAGPGSGSPSAAASSSWHTLFT AEEGQLYGPCGGGGGGGGGGGGGGGGGGGGGGGEAGAVAP YGYTRPPQGLAGQESDFTAPDVWYPGGMVSRVPYPSPTCVKSE MGPWMDSYSGPYGDMRLETARDHVLPIDYYFPPQKTCLICGDE ASGCHYGALTCGSCKVFFKRAAEGKQKYLCASRNDCTIDKFRR KNCPSCRLRKCYEAGMTLGARKLKKLGNLKLQEEGEASSTTSPT EETTQKLTVSHIEGYECQPIFLNVLEAIEPGVVCAGHDNNQPDSF AALLSSLNELGERQLVHVVKWAKALPGFRNLHVDDQMAVIQY SWMGLMVFAMGWRSFTNVNSRMLYFAPDLVFNEYRMHKSRM YSQCVRMRHLSQEFGWLQITPQEFLCMKALLLFSIIPVDGLKNQ KFFDELRMNYIKELDRIIACKRKNPTSCSRRFYQLTKLLDSVQPI ARELHQFTFDLLIKSHMVSVDFPEMMAEIISVQVPKILSGKVKPI YFHTQ (SEQ ID NO: 1) |

In some embodiments, an AR modulator as described herein is one dimensioned to fit within the pocket defined by residues F876 and L741 of an AR receptor. In some embodiments, an AR modulator as described herein is one dimensioned to fit within the helix 12 pocket defined as a region of the AR LBD distal to F876 of an wild type AR receptor. In some embodiments, an AR modulator as described herein is one dimensioned to fit within the helix 12 pocket defined as a region of the AR LBD distal to residue 876 of an F876Xaa mutant AR receptor, wherein Xaa is selected from leucine, isoleucine, tyrosine, cysteine, or serine. In some embodiments, an AR modulator as described herein is one dimensioned to fit within the helix 12 pocket defined as a region of the AR LBD distal to residue L876 of an F876L mutant AR receptor.

In some embodiments, the present invention provides compounds of formula I:

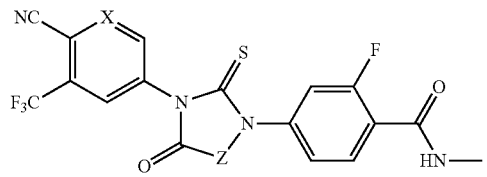

or a pharmaceutically acceptable salt thereof, wherein:
X is CH or N;
Z is —$CH_2$— or Ring B; and
Ring B is an optionally substituted 5-14 membered saturated or partially unsaturated carbocyclic monocyclic or bicyclic ring, wherein said ring is spiro-fused at point Z.

As defined generally above, X is CH or N. In some embodiments X is CH. In some embodiments X is N.

As defined generally above, Z is —$CH_2$— or Ring B.
In some embodiments, Z is —$CH_2$—. In some embodiments, Z is Ring B.

As defined generally above, Ring B is an optionally substituted saturated or partially unsaturated 5-14 membered carbocyclic monocyclic or bicyclic ring, wherein said ring is spiro-fused at point Z. In some embodiments, Ring B is an unsubstituted 5-14 membered saturated or partially unsaturated carbocyclic monocyclic or bicyclic ring, wherein said ring is spiro-fused at point Z. In some embodiments, Ring B is an optionally substituted 5-8 membered saturated or partially unsaturated carbocyclic monocyclic ring, wherein said ring is spiro-fused at point Z. In some embodiments, Ring B is an optionally substituted 7-14 membered saturated or partially unsaturated carbocyclic bicyclic ring, wherein said ring is spiro-fused at point Z. In some embodiments, Ring B is an optionally substituted saturated 5-8 membered monocyclic ring, wherein said ring is spiro-fused at point Z. In some embodiments, Ring B is an optionally substituted partially unsaturated 5-8 membered monocyclic ring, wherein said ring is spiro-fused at point Z.

One of skill in the art will appreciate that when Ring B is asymmetrically substituted on a tetrahedral carbon, a stereocenter exists. In some embodiments said stereocenter has R stereochemistry. In some embodiments said stereocenter has S stereochemistry. In some embodiments Ring B is substituted with multiple substituents and each stereocenter independently has R or S stereochemistry.

In some embodiments, the present invention provides a compound of formula I:

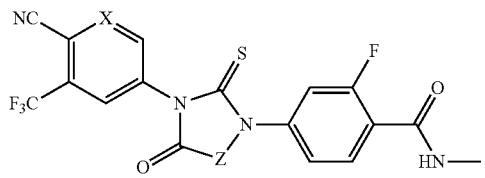

I or a pharmaceutically acceptable salt thereof, wherein:

X is CH or N;

Z is —CH$_2$— or Ring B; and

Ring B is an 5-14 membered saturated or partially unsaturated carbocyclic monocyclic or bicyclic ring substituted with n instances of R$^b$, wherein said ring is spiro-fused at point Z;

n is 0 to 4;

and each R$^b$ is independently substituted or unsubstituted C$_{1-6}$ aliphatic.

In some embodiments, the present invention provides a compound of formula I wherein Z is hydrogen, thereby forming a compound of formula II:

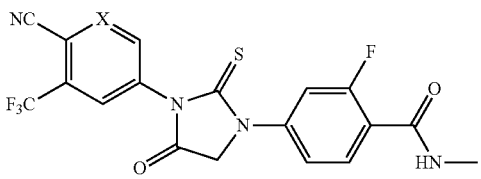

II or a pharmaceutically acceptable salt thereof, wherein X is CH or N.

In some embodiments, the present invention provides a compound of formula I wherein Z is Ring B, thereby forming a compound of formula III:

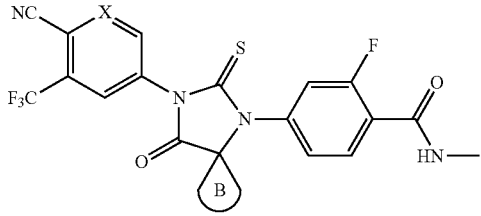

III or a pharmaceutically acceptable salt thereof, wherein each of X and Ring B is defined above and described in embodiments herein, both singly and in combination.

In some embodiments, the present invention provides a compound of formula I wherein Z is Ring B, thereby forming a compound of formula III:

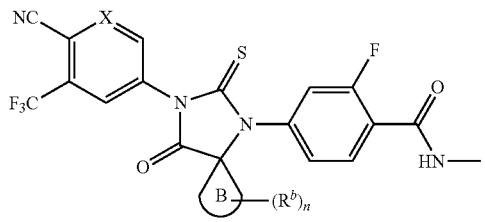

III or a pharmaceutically acceptable salt thereof, wherein each of X, Ring B, n and R$^b$ is as defined above and described in embodiments herein, both singly and in combination.

In some embodiments, the present invention provides a compound of formula I wherein Z is Ring B, and wherein Ring B is cyclohexyl substituted with n instances of R$^b$, wherein n is 0 to 4 and each R$^b$ is independently substituted or unsubstituted C$_{1-6}$ aliphatic, thereby forming a compound of formula IV:

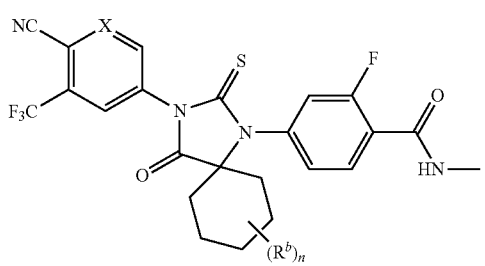

IV wherein X is defined above and described in embodiments herein, both singly and in combination.

As defined generally above, each R$^b$ is independently substituted or unsubstituted C$_{1-6}$ aliphatic. In some embodiments, each R$^b$ is independently unsubstituted C$_{1-6}$ aliphatic. In some embodiments, each R$^b$ is methyl.

As defined generally above, n is 0 to 4. In some embodiments, n is 0. In some embodiments, n is 1 to 4. In some embodiments, n is 2. In some embodiments, n is 4.

In some embodiments, the present invention provides a compound of formula IV wherein the spiro stereocenter formed between the cyclohexyl ring and the thiohydantoin ring is in the R configuration or the S configuration, thereby forming a compound of formulae IV-R or IV-S:

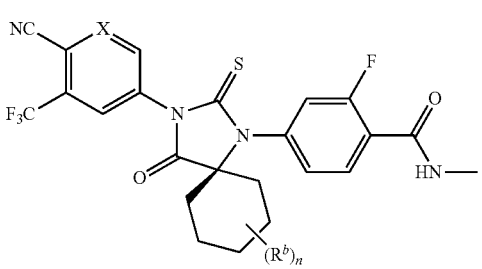

IV-R

-continued
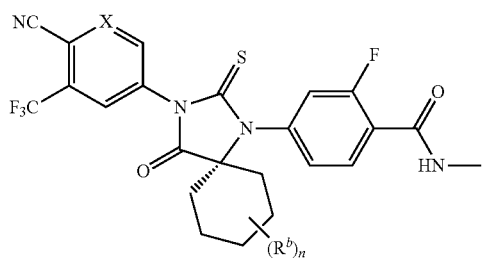
IV-S
wherein each of variables X, n, and $R^b$ is defined above and described in embodiments herein, both singly and in combination.
Exemplary compounds of formula I are set forth in Table 1, below:
TABLE 1
Exemplary Compounds of Formula I
| Compound ID | Compound Structure |
|---|---|
| I-1 | 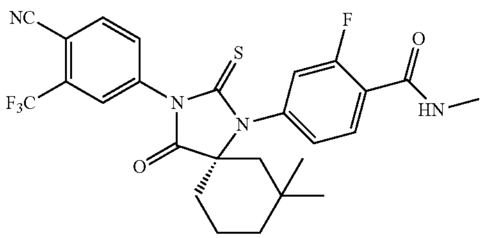 [SMILES: CNC(=O)c1ccc(N2C(=S)N(c3ccc(C#N)c(C(F)(F)F)c3)C(=O)[C@@]23CCCC(C)(C)C3)cc1F] |
| I-2 | 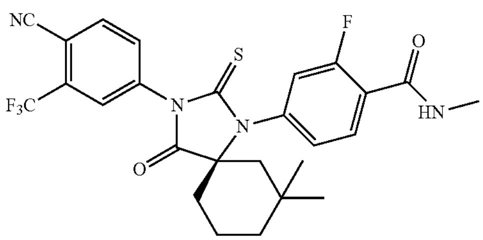 [SMILES: CNC(=O)c1ccc(N2C(=S)N(c3ccc(C#N)c(C(F)(F)F)c3)C(=O)[C@]23CCCC(C)(C)C3)cc1F] |
| I-3 | 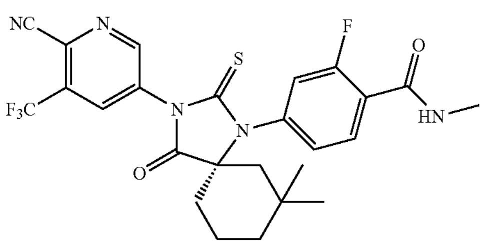 [SMILES: CNC(=O)c1ccc(N2C(=S)N(c3cnc(C#N)c(C(F)(F)F)c3)C(=O)[C@@]23CCCC(C)(C)C3)cc1F] |
| I-4 | 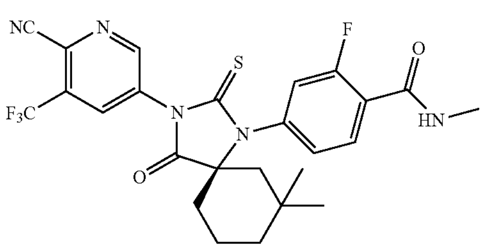 [SMILES: CNC(=O)c1ccc(N2C(=S)N(c3cnc(C#N)c(C(F)(F)F)c3)C(=O)[C@]23CCCC(C)(C)C3)cc1F] |
| I-5 | 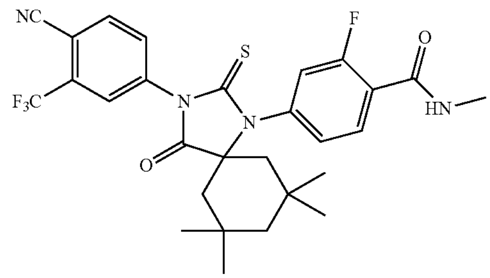 [SMILES: CNC(=O)c1ccc(N2C(=S)N(c3ccc(C#N)c(C(F)(F)F)c3)C(=O)C23CC(C)(C)CC(C)(C)C3)cc1F] |
| I-6 | 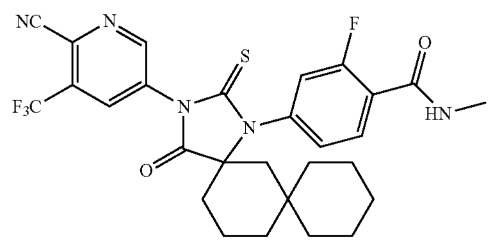 [SMILES: CNC(=O)c1ccc(N2C(=S)N(c3cnc(C#N)c(C(F)(F)F)c3)C(=O)C23CCCC2(CCCCC2)C3)cc1F] |
| I-7 | 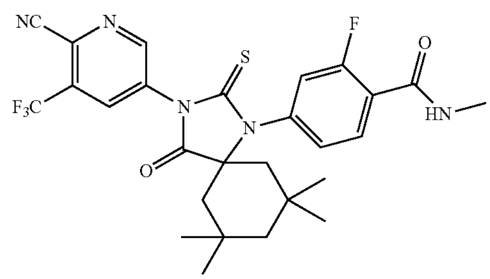 [SMILES: CNC(=O)c1ccc(N2C(=S)N(c3cnc(C#N)c(C(F)(F)F)c3)C(=O)C23CC(C)(C)CC(C)(C)C3)cc1F] |
| I-8 | 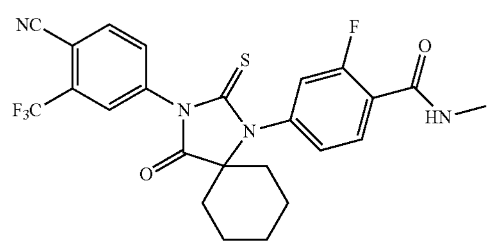 [SMILES: CNC(=O)c1ccc(N2C(=S)N(c3ccc(C#N)c(C(F)(F)F)c3)C(=O)C23CCCCC3)cc1F] |
| I-9 | 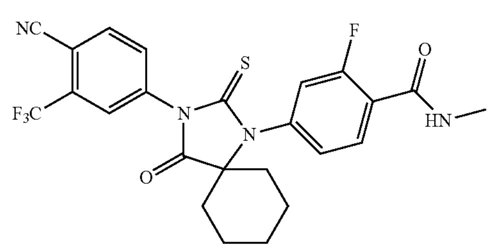 [SMILES: CNC(=O)c1ccc(N2C(=S)N(c3ccc(C#N)c(C(F)(F)F)c3)C(=O)C23CCCCC3)cc1F] |

TABLE 1-continued

Exemplary Compounds of Formula I

| Compound ID | Compound Structure |
|---|---|
| I-10 | 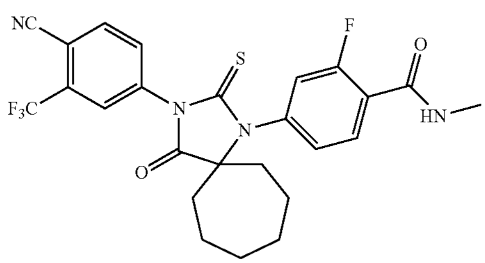 [SMILES: CNC(=O)c1ccc(N2C(=S)N(c3ccc(C#N)c(C(F)(F)F)c3)C(=O)C23CCCCCC3)cc1F] |
| I-11 | 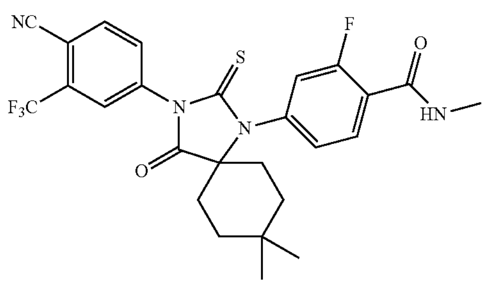 [SMILES: CNC(=O)c1ccc(N2C(=S)N(c3ccc(C#N)c(C(F)(F)F)c3)C(=O)C23CCC(C)(C)CC3)cc1F] |
| I-12 | 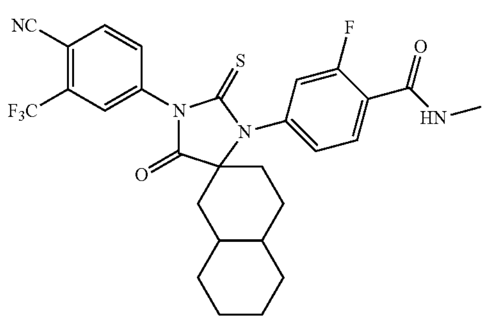 [SMILES: CNC(=O)c1ccc(N2C(=S)N(c3ccc(C#N)c(C(F)(F)F)c3)C(=O)C23CCC2CCCCC2C3)cc1F] |
| I-13 | 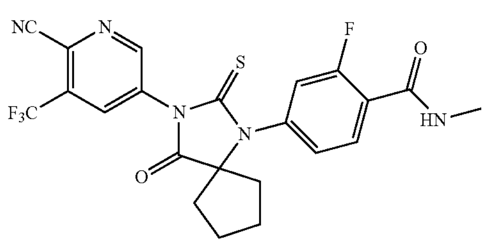 [SMILES: CNC(=O)c1ccc(N2C(=S)N(c3cnc(C#N)c(C(F)(F)F)c3)C(=O)C23CCCC3)cc1F] |
| I-14 | 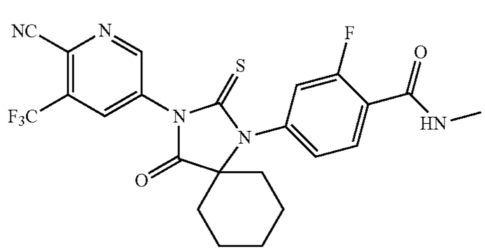 [SMILES: CNC(=O)c1ccc(N2C(=S)N(c3cnc(C#N)c(C(F)(F)F)c3)C(=O)C23CCCCC3)cc1F] |
| I-15 | |
| I-16 | |
| I-17 | |
| I-18 | |
| I-19 | |

TABLE 1-continued

Exemplary Compounds of Formula I

| Compound ID | Compound Structure |
|---|---|
| I-20 | (structure) |
| I-21 | (structure) |
| I-22 | (structure) |
| I-23 | (structure) |
| I-24 | (structure) |
| I-25 | (structure) |
| I-26 | (structure) |
| I-27 | (structure) |

In certain embodiments, the present invention provides any compound selected from those depicted in Table 1, above, or a pharmaceutically acceptable salt thereof, or any combination of the foregoing.

Compounds or salts thereof provided by the present invention may be utilized in any of a variety of physical forms. For example, in some embodiments, provided compounds (or salts thereof) are utilized in a solid form; in some such embodiments, provided compounds (or salts thereof) are utilized in an amorphous solid form. In some embodiments, provided compounds are utilized in a crystalline solid form. In some embodiments, provided compounds (or salts thereof) are utilized in a solid form (e.g., a crystalline solid form) that is a solvate or hydrate.

In some embodiments, a composition comprising a compound provided herein contains only a single physical form of the compound; in some embodiments, a composition comprising a compound provided herein contains more than one physical form of the compound. In some embodiments, a composition comprising a compound provided herein contains only a single isomeric (e.g., steroisomer, geometric isomer, or isotopic isomer) form of the compound. In some embodiments, a composition comprising a compound provided herein contains more than one isomeric form of the compound.

4. Uses, Formulation and Administration and Pharmaceutically Acceptable Compositions According to some embodiments, the invention provides a composition comprising a compound of this invention or a pharmaceutically acceptable derivative thereof and a pharmaceutically acceptable carrier, adjuvant, or vehicle.

In certain embodiments, the invention provides compositions containing an amount of compound effective to measurably modulate, agonize, or antagonize an AR, in a biological sample or in a patient. In certain embodiments, the amount of compound in compositions of this invention is such that is effective to measurably modulate, agonize, or antagonize an AR mediated biological process in a biological sample or in a patient. In certain embodiments, provided compositions contain a unit dose amount of a compound described herein, wherein administration of such unit dose amount as part of a therapeutic regimen correlates with a desired pharmacologic and/or therapeutic outcome.

In certain embodiments, a composition of this invention is formulated for administration to a patient in need of such composition. In some embodiments, a composition of this invention is formulated for oral administration to a patient.

As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

The term "patient," as used herein, means an animal, often a mammal, and in many embodiments a human.

The term "pharmaceutically acceptable carrier, adjuvant, or vehicle", as used herein, refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, or salt of an ester of a compound of this invention that, upon administration to a recipient, is capable of providing, either directly or indirectly, a compound of this invention or an inhibitorily active metabolite or residue thereof.

As used herein, the term "active metabolite or residue thereof" means that a metabolite or residue thereof is also an agonist or antagonist of AR or is retains therapeutic activity in treating the same disease, disorder or condition.

Compositions of the present invention may be formulated for any appropriate route of administration. For example, in some embodiments, provided compositions may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, provided compositions are administered orally, intraperitoneally or intravenously. Sterile injectable forms of the compositions of this invention may be aqueous or oleaginous suspension. Such suspensions may be formulated according to techniques known in the art using suitable dispersing or wetting agents and suspending agents.

In some embodiments, pharmaceutically acceptable compositions of the invention may be formulated as injectable preparations. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In some embodiments, injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In some embodiments, for example in order to prolong effects of a compound or composition, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively or additionally, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In some embodiments, sterile injectable preparations may be or include a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. Such oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and *acacia*, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

In some embodiments, provided compounds can be in micro-encapsulated form with one or more excipients as noted above. Solid dosage forms such as tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively or additionally, pharmaceutically acceptable compositions of this invention may be administered in the form of suppositories for rectal administration. Such compositions can be prepared by combining a provided compound with a suitable non-irritating excipient that is solid at room temperature but liquid at rectal temperature and therefore will melt in the rectum to release the drug. Such materials include cocoa butter, beeswax and polyethylene glycols.

In some embodiments, pharmaceutically acceptable compositions of this invention may be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively or additionally, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively or additionally, for ophthalmic uses, the pharmaceutically acceptable compositions may be formulated in an ointment such as petrolatum.

In some embodiments, pharmaceutically acceptable compositions of this invention may be administered by nasal aerosol or inhalation. Such compositions may be prepared according to techniques well-known in the art of pharmaceutical formulation, for example as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration. Such formulations may be administered with or without food. In some embodiments, pharmaceutically acceptable compositions of this invention are administered without food. In some embodiments, pharmaceutically acceptable compositions of this invention are administered with food.

The amount of compounds of the present invention that may be combined with the carrier materials to produce a composition in a single dosage form will vary depending upon the host treated, the particular mode of administration. In some embodiments provided compositions are formulated so that a dosage of between 0.01-100 mg/kg body weight/day of the inhibitor can be administered to a patient receiving these compositions.

It should also be understood that a specific dosage and treatment regimen for any particular patient may depend upon a variety of factors, including the activity of the specific compound employed, the age, body weight, general health, sex, diet, time of administration, rate of excretion, drug combination, and the judgment of the treating physician and the severity of the particular disease being treated. In some embodiments, amount of a compound of the present invention included in a composition described herein is determined by activity and/or bioavailability of the particular compound, so that compositions of different compounds may include different absolute amounts of compound.

Uses of Compounds and Pharmaceutically Acceptable Compositions

Compounds and compositions described herein are useful in the treatment of any of a variety of diseases, disorders, and conditions. In some embodiments, provided compounds and compositions are useful in the treatment of diseases, disorders, or conditions associated with activity of androgen receptors.

The activity of a compound utilized in this invention as a modulator, agonist or antagonist of AR or treatment for an AR-mediated disease, disorder or condition, may be assayed in vitro or in vivo. An in vivo assessment of the efficacy of the compounds of the invention may be made using an animal model of an AR-mediated disease, disorder or condition, e.g., a rodent or primate model. Cell-based assays may be performed using, e.g., a cell line isolated from a tissue that expresses either wild type or mutant AR. Additionally, biochemical or mechanism-based assays, e.g., transcription assays using a purified protein, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with compounds of the invention. Alternate or additional in vitro assays may be used to quantitate the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively or additionally, inhibitor binding may be determined by running a competition experiment where new inhibitors are incubated with purified proteins or nucleic acids bound to known radioligands. Detailed conditions of exemplary systems for assaying a compound utilized in this invention as a modulator, agonist or antagonist of AR are set forth in the Examples below. Such assays are exemplary and not intended to limit the scope of the invention. The skilled practitioner can appreciate that modifications can be made to conventional assays to develop equivalent or other assays that can be employed to comparably assess activity or otherwise characterize compounds and/or compositions as described herein.

As used herein, the terms "treatment," "treat," and "treating" refer to reversing, alleviating, delaying the onset of, reducing incidence or severity, or inhibiting the progress of a disease, disorder or condition, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Compounds and/or compositions described herein may be administered using any amount and any route of administration effective for treating a disease, disorder, or condition. In some embodiments, compounds and/or compostions are administered in an amount and/or by a route effective for treating a cardiovascular disease, disorder or condition, an inflammatory disease, disorder or condition, a neurological disease, disorder or condition, an ocular disease, disorder or condition, a metabolic disease, disorder or condition, a cancer or other proliferative disease, disorder or condition, a reproductive disease, disorder or condition, or a bone disease, disorder or condition.

In some embodiments, compounds and/or compositions described herein may be administered using any amount and any route of administration effective for treating or lessening the severity of a disease, disorder or condition associated with AR.

In some embodiments, the compounds and compositions, according to the method of the present invention, may be administered using any amount and any route of administration effective for treating a cancer or another proliferative disease, disorder or condition. In some embodiments, the cancer or other proliferative disease, disorder or condition is a prostate cancer. In some embodiments, the cancer or other proliferative disease, disorder or condition is a castration-resistant prostate cancer (CRPC). In some embodiments, the cancer or other proliferative disease, disorder or condition is a castration-resistant prostate cancer (CRPC) bearing a mutation in AR. In some embodiments, the mutation in AR is a mutation of Phe876. In some embodiments, the mutation in AR is a mutation of Phe876 to leucine. In some embodiments, the mutation in AR is a mutation of Phe876 to isoleucine. In some embodiments, the mutation in AR is a mutation of Phe876 to valine. In some embodiments, the mutation in AR is a mutation of Phe876 to serine. In some embodiments, the mutation in AR is a mutation of Phe876 to cysteine. In some embodiments, the mutation in AR is a mutation of Phe876 to tyrosine. In some embodiments, the cancer or other proliferative disease, disorder or condition is a prostate cancer that is resistant to treatment with Enzalutamide.

The present invention encompasses the recognition that mutations in the AR polypeptide can render the AR polypeptide resistant to anti-androgens or convert anti-androgens to androgen agonists. In some embodiments, the invention provides compounds that can be used to effect anti-androgenic effects despite the presence of such mutations.

The amino acid sequence of an AR polypeptide described herein can exist in a mutant AR containing, or can be modified to produce an mutant AR polypeptide variant at least one (e.g., 1, 2, 3, 4, 5, 6, 7, 8, 9, 10, or more) additions, substitutions, or deletions of a wild-type amino acid residue.

In some embodiments, the AR polypeptide variants described herein result in a loss of inhibition of AR activity by one or more antiandrogens of 0, 1, 2, 3, 4, 5, 6, 7, 8, 9, 10 up to 100%. In some embodiments, the AR polypeptide variants described herein convert anti-androgens to androgen receptor agonists.

Specific, nonlimiting amino acid residues that can be modified in an AR mutant include, e.g., E566, E589, E669, C687, A700, N772, H777, C785, F877, K911, of the AR polypeptide. These amino acid residues can be substituted with any amino acid or amino acid analog. For example, the substitutions at the recited positions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine). In particular instances, an amino acid substitution is E566K, E589K, E669K, C687Y, A700T, N772S, H777Y, C785R, F877C, F877I, F877L, F877S, F877V, F877Y and/or K911E.

In some embodiments, the AR mutants as described herein can include additional modifications of the AR polypeptide previously described in the art, including but not limited to, e.g., A597T, S648G, P683T, D696E, R727H, N728I, I738F, W741L, W741C, W741L, M743V, G751S, A871V, H874Y, T878A, T878S, and P914S.

In some embodiments, the compounds and compositions, according to the method of the present invention, may be administered using any amount and any route of administration effective for treating a bone disease, disorder or condition. In some embodiments, the bone disease, disorder or condition is osteoporosis.

In will be appreciated by those skilled in the art that the exact amount of a provided compound or composition may vary from subject to subject, depending on the species, age, and general condition of the subject, the severity of the infection, the particular agent, its mode of administration, and the like.

In some embodiments, compounds of the invention are formulated in dosage unit form, for example for ease of administration and uniformity of dosage. The expression "dosage unit form" or "unit dosage" as used herein refers to a physically discrete unit of agent appropriate for the patient to be treated. It will be understood, however, that total daily usage of the compounds and compositions of the present invention may be decided by the attending physician within the scope of sound medical judgment. The specific effective dose level for any particular patient or organism may depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

According to some embodiments, the invention relates to a method of modulating, agonizing or antagonizing AR in a biological sample comprising the step of contacting said biological sample with a compound of this invention, or a composition comprising said compound. In some embodiments, the invention provides a method of antagonizing AR in a biological sample comprising the step of contacting said biological sample with a compound of this invention. In some embodiments, the invention provides a method of agonizing AR in a biological sample comprising the step of contacting said biological sample with a compound of this invention. In some embodiments, the agonism of the AR is partial agonism.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Agonism or antagonism of receptors in a biological sample is useful for a variety of purposes that are known to one of skill in the art. Examples of such purposes include, but are not limited to biological assays, gene expression studies, and biological target identification.

Some embodiments of the present invention relate to a method of modulating, agonizing or antagonizing AR in a patient comprising the step of administering to said patient a compound of the present invention, or a composition comprising said compound. In some embodiments the invention provides a method of antagonizing AR in a patient comprising the step of administering to said patient a compound of the present invention, or a composition comprising said compound.

In some embodiments, the invention relates to a method of modulating, agonizing or antagonizing AR activity in a patient comprising the step of administering to said patient a compound of the present invention, or a composition comprising said compound. In certain embodiments, the present invention provides a method for treating a disease, disorder or condition mediated by AR, in a patient in need thereof, comprising the step of administering to said patient a compound according to the present invention or pharmaceutically acceptable composition thereof. Such diseases, disorders and conditions are described in detail herein.

In some embodiments compounds and/or compositions of the present invention may be used in a method of treating a cardiovascular disease, disorder, or condition, an inflammatory disease, disorder or condition, a neurological disease, disorder or condition, an ocular disease, disorder or condition, a metabolic disease, disorder or condition, a cancer or other proliferative disease, disorder or condition, a reproductive disease, disorder or condition, or a bone disease, disorder or condition. In certain embodiments the compounds and compositions of the present invention may be used to treat a cardiovascular disease, disorder or condition, an inflammatory disease, disorder or condition, a neurological disease, disorder or condition, an ocular disease, disorder or condition, a metabolic disease, disorder or condition, a cancer or other proliferative disease, disorder or condition, a reproductive disease, disorder or condition, or a bone disease, disorder or condition in a mammal. In certain embodiments the mammal is a human patient.

In some embodiments the present invention provides a method of treating a cardiovascular disease, disorder or condition, an inflammatory disease, disorder or condition, a neurological disease, disorder or condition, an ocular disease, disorder or condition, a metabolic disease, disorder or condition, a cancer or other proliferative disease, disorder or condition, a reproductive disease, disorder or condition, or a bone disease, disorder or condition, comprising administering a compound or composition of the present invention to a patient in need thereof. In certain embodiments the method of treating a cardiovascular disease, disorder or condition, an inflammatory disease, disorder or condition, a neurological disease, disorder or condition, an ocular disease, disorder or condition, a metabolic disease, disorder or condition, a cancer or other proliferative disease, disorder or condition, a reproductive disease, disorder or condition, or a bone disease, disorder or condition comprises administering compounds and compositions of the present invention to a mammal. In certain embodiments the mammal is a human.

In certain embodiments, the present invention provides a method of treating a cancer or another proliferative disease, disorder or condition, comprising administering a compound or composition of the present invention to a patient with a cancer or another proliferative disease, disorder or condition. In certain embodiments, the method of treating a cancer or other proliferative disorder comprises administering compounds and compositions of the present invention to a mammal. In certain embodiments, the cancer or other proliferative disorder is a prostate cancer. In certain embodiments, the prostate cancer is a castration-resistant prostate cancer. In certain embodiments, the mammal is a human.

As used herein, the terms "treating a cancer" refers to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the compounds and compositions described herein and against which the methods described herein are useful include but are not limited to breast, prostate, brain, blood, bone marrow, bone, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by compounds or compositions of the invention is a skin cancer, lung cancer, breast cancer, prostate cancer, leukemia, kidney cancer, esophageal cancer, brain cancer, bone cancer or colon cancer. In some embodiments, the cancer treated by the compounds or compositions of the invention is a prostate cancer.

Depending upon the particular disease, disorder or condition to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or composition thereof, is administered in combination with another modulator, agonist or antagonist of AR. In some embodiments, a provided compound, or composition thereof, is administered in combination with one or more other therapeutic agents. In some embodiments the AR modulators, agonists or antagonists include, but are not limited to non-steroidal antiandrogens, aminoglutethimide, enzalutamide, bicalutamide, nilutamide, flutamide, steroidal antiandrogens, finasteride, dutasteride, bexlosteride, izonsteride, turosteride, epristeride, other inhibitors of 5-alpha-reductase, 3,3'-diindolylmethane (DIM), N-butylbenzene-sulfonamide (NBBS).

In certain embodiments, a provided compound, or composition thereof, is administered in combination with another therapeutic agent, wherein said therapeutic agent is a an androgen deprivation therapeutic agent. In some embodiments, the androgen deprivation therapeutic agent is abiraterone, abiraterone acetate, buserelin, cyproterone, cyproterone acetate, degarelix, goserelin, ketoconazole, Lupron (leuprorelin, leuprolide acetate), orteronel (TAK-700), spironolactone, or triptorelin.

In certain embodiments, a provided compound, or a composition thereof, is administered in combination with another anti-cancer, cytotoxin, chemotherapeutic agent, or radio-therapeutic agent, and/or with another agent (e.g., a palliative agent, pain reliever, anti-emetic agent, anti-nausea agent, anti-inflammatory agent, etc.) commonly administered to cancer patients.

In certain embodiments, the anti-cancer or chemotherapeutic agents used in combination with compounds or compositions of the invention include, but are not limited to imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Proteinbound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In some embodiments, a provided compound, or a composition thereof, is administered to a patient undergoing radiation therapy. In some embodiments, the radiation therapy is external beam gamma or x-ray radiation therapy. In some embodiments, the radiation therapy is brachytherapy. In some embodiments, the brachytherapy uses $^{198}$Au, $^{252}$Cf, $^{60}$Co, $^{137}$Cs, $^{125}$I, $^{192}$Ir, $^{32}$P, $^{103}$Pd, $^{226}$Ra, $^{106}$Ru, $^{145}$Sm, $^{90}$Sr, and $^{182}$Ta.

In certain embodiments, a combination of 2 or more therapeutic agents may be administered together with compounds of the invention. In certain embodiments, a combination of 3 or more therapeutic agents may be administered with compounds of the invention.

Other examples of agents the inhibitors of this invention may also be combined with include, without limitation: vitamins and nutritional supplements, cancer vaccines, treatments for neutropenia (e.g. G-CSF, filgrastim, lenograstim), treatments for thrombocytopenia (e.g. blood transfusion, erythropoietin), antiemetics (e.g. 5-HT$_3$ receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, compounds of the present invention, or a pharmaceutically acceptable composition thereof, are administered in combination with antisense agents, a monoclonal or polyclonal antibody or an siRNA therapeutic.

Those additional agents may be administered separately from an inventive compound-containing composition, as part of a multiple dosage regimen. Alternatively or in addition to those additional agents administered separately, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Therapeutic Entities

Multifunctional agents described herein in many embodiments comprise at least one therapeutic entity, in addition to a targeting entity (e.g., compound of formula I) described above. Contemplated therapeutic entities include, without limitation, anti-cancer agents (e.g., agents that inhibit tumor growth, agents that inhibit proliferation of cancer cells, agents that preferentially kill cancer cells, agents that inhibit angiogenesis, etc.), agents that attenuate any adverse effects (e.g., antiemetics, etc.) and/or with other approved chemotherapeutic drugs, as well as adjuvants (e.g., agents that elicit adjuvant effects).

Suitable therapeutic entities include anti-cancer agents can belong to any of various classes of compounds including, but not limited to, small molecules, peptides, saccharides, steroids, antibodies, fusion proteins, antisense polynucleotides, ribozymes, small interfering RNAs, peptidomimetics, and the like. Similarly, suitable anti-cancer agents can be found among any of a variety of classes of anti-cancer agents including, but not limited to, alkylating agents, anti-metabolite drugs, anti-mitotic antibiotics, alkaloidal anti-tumor agents, hormones and anti-hormones, interferons, non-steroidal anti-inflammatory drugs, and various other anti-tumor agents.

Examples of chemotherapeutics include, but are not limited to, anti-mitotic agents, alkylating drugs (e.g., mechlorethamine, chlorambucil, cyclophosphamide, melphalan, ifosfamide, etc.), antimetabolites (e.g., methotrexate, etc.), purine antagonists and pyrimidine antagonists (e.g., 6-mercaptopurine, 5-fluorouracil, cytarabine, gemcitabine, etc.), spindle poisons (e.g., vinblastine, vincristine, vinorelbine, paclitaxel, etc.), podophyllotoxins (e.g., etoposide, irinotecan, topotecan, etc.), antibiotics (e.g., doxorubicin, bleomycin, mitomycin, etc.), nitrosureas (e.g., carmustine, lomustine, nomustine, etc.), inorganic ions (e.g., cisp latin, carboplatin, etc.), enzymes (e.g., asparaginase, etc.), and hormones (e.g., tamoxifen, leuprolide, flutamide, megestrol, etc.), to name a few. For a more comprehensive discussion of updated cancer therapies see, www.cancer.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Non-limiting examples of cytotoxic agents which can be employed as a therapeutic entity for any of the multifunctional agents contemplated in the present disclosure may be selected from: CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (adriamycin/doxorubicin, bleomycin, vinblastine, and dacarbazine); MOPP (mechloethamine, vincristine, prednisone and procarbazine) alternating with ABV (adriamycin/doxorubicin, bleomycin, and vinblastine); MOPP (mechloethamine, vincristine, prednisone, and procarbazine) alternating with ABVD (adriamycin/doxorubicin, bleomycin, vinblastine, and dacarbazine); ChIVPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); CVP-I (cyclophosphamide, vincristine, and prednisone), ESHOP (etoposide, methylpredisolone, high-dose cytarabine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP(B) (cyclophosphamide, etoposide, procarbazine, prednisone, and bleomycin), CHOP-B (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

In some embodiments, chemotherapeutic drugs prescribed for brain tumors may be employed as a therapeutic entity in accordance with the invention. These include, but are not limited to, temozolomide (Temodar®), procarbazine (Matulane), and lomustine (CCNU), which are taken orally; vincristine (Oncovin® or Vincasar PFS®), cisplatin (Platinol®), carmustine (BCNU, BiCNU), and carboplatin (Paraplatin®), which are administered intravenously; and mexotrexate (Rheumatrex® or Trexall®), which can be administered orally, intravenously or intrathecally (i.e., injected directly into spinal fluid). BCNU is also given under the form of a polymer wafer implant during surgery (Giadel® wafers). One of the most commonly prescribed combination therapy for brain tumors is PCV (procarbazine, CCNU, and vincristine) which is usually given every six weeks.

In embodiments where the tumor to be treated is a brain tumor of neuroectodermal origin, a composition or method of the present invention may employ agents for the management of symptoms such as seizures and cerebral edema. Examples of anticonvulsants successfully administered to control seizures associated with brain tumors include, but are not limited to, phenytoin (Dilantin®), Carbamazepine (Tegretol®) and divalproex sodium (Depakote®). Swelling of the brain may be treated with steroids (e.g., dexamethasone (Decadron®).

Certain Embodiments of Targeting Moiety Conjugate Agents

In a number of embodiments, the invention provides multifunctional agents comprising a target entity which essentially consists of a compound of formula I). In such embodiments, therefore, the multifunctional agents according to the present invention are conjugates of compounds of formula I. Non-limiting embodiments of useful conjugates are provided below.

For example, provided conjugates comprise a compound of formula I and a nucleic acid molecule that is useful as a therapeutic (e.g., anti-cancer) agent. A variety of chemical types and structural forms of nucleic acid can be suitable for such strategies. These include, by way of non-limiting example, DNA, including single-stranded (ssDNA) and double-stranded (dsDNA); RNA, including, but not limited to ssRNA, dsRNA, tRNA, mRNA, rRNA, enzymatic RNA; RNA:DNA hybrids, triplexed DNA (e.g., dsDNA in association with a short oligonucleotide), and the like.

In some embodiments, the nucleic acid agent is between about 5 and 2000 nucleotides long. In some embodiments, the nucleic acid agent is at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides long. In some embodiments, the nucleic acid agent is less than about 2000, 1900, 1800, 1700, 1600, 1500, 1400, 1300, 1200, 1100, 1000, 900, 800, 700, 600, 500, 450, 400, 350, 300, 250, 200, 150, 100, 50, 45, 40, 35, 30, 25, 20 or fewer nucleotides long.

In some embodiments, the nucleic acid agent comprises a promoter and/or other sequences that regulate transcription. In some embodiments, the nucleic acid agent comprises an origin of replication and/or other sequences that regulate replication. In some embodiments, the nucleic acid agent does not include a promoter and/or an origin of replication.

Nucleic acid anti-cancer agents suitable for use in the practice of the present invention include those agents that target genes associated with tumorigenesis and cell growth or cell transformation (e.g., proto-oncogenes, which code for proteins that stimulate cell division), angiogenic/anti-angiogenic genes, tumor suppressor genes (which code for proteins that suppress cell division), genes encoding proteins associated with tumor growth and/or tumor migration, and suicide genes (which induce apoptosis or other forms of cell death), especially suicide genes that are most active in rapidly dividing cells.

Examples of genes associated with tumorigenesis and/or cell transformation include MLL fusion genes, BCR-ABL, TEL-AML1, EWS-FLI1, TLS-FUS, PAX3-FKHR, Bcl-2, AML1-ETO, AML1-MTG8, Ras, Fos PDGF, RET, APC, NF-1, Rb, p53, MDM2 and the like; overexpressed genes such as multidrug resistance genes; cyclins; beta-Catenin; telomerase genes; c-myc, n-myc, Bcl-2, Erb-B1 and Erb-B2; and mutated genes such as Ras, Mos, Raf, and Met. Examples of tumor suppressor genes include, but are not limited to, p53, p21, RB1, WT1, NF1, VHL, APC, DAP kinase, p16, ARF, Neurofibromin, and PTEN. Examples of genes that can be targeted by nucleic acid agents useful in anti-cancer therapy include genes encoding proteins associated with tumor migration such as integrins, selectins, and metalloproteinases; anti-angiogenic genes encoding proteins that promote formation of new vessels such as Vascular Endothelial Growth Factor (VEGF) or VEGFr; anti-angiogenic genes encoding proteins that inhibit neovascularization such as endostatin, angiostatin, and VEGF-R2; and genes encoding proteins such as interleukins, interferon, fibroblast growth factor ($\alpha$-FGF and $\beta$-FGF), insulin-like growth factor (e.g., IGF-1 and IGF-2), Platelet-derived growth factor (PDGF), tumor necrosis factor (TNF), Transforming Growth Factor (e.g., TGF-$\alpha$ and TGF-$\beta$, Epidermal growth factor (EGF), Keratinocyte Growth Factor (KGF), stem cell factor and its receptor c-Kit (SCF/c-Kit) ligand, CD40L/CD40, VLA-4 VCAM-1, ICAM-1/LFA-1, hyalurin/CD44, and the like. As will be recognized by one skilled in the art, the foregoing examples are not exclusive.

Nucleic acid agents suitable for use in the invention may have any of a variety of uses including, for example, use as anti-cancer or other therapeutic agents, probes, primers, etc. Nucleic acid agents may have enzymatic activity (e.g., ribozyme activity), gene expression inhibitory activity (e.g., as antisense or siRNA agents, etc), and/or other activities. Nucleic acids agents may be active themselves or may be vectors that deliver active nucleic acid agents (e.g., through replication and/or transcription of a delivered nucleic acid). For purposes of the present specification, such vector nucleic acids are considered "therapeutic agents" if they encode or otherwise deliver a therapeutically active agent, even if they do not themselves have therapeutic activity.

In certain embodiments, conjugates comprise a nucleic acid therapeutic agent that comprises or encodes an antisense compound. The terms "antisense compound or agent," "antisense oligomer," "antisense oligonucleotide," and "antisense oligonucleotide analog" are used herein interchangeably, and refer to a sequence of nucleotide bases and a subunit-to-subunit backbone that allows the antisense compound to hybridize to a target sequence in an RNA by Watson-Crick base pairing to form an RNA oligomer heteroduplex within the target sequence. The oligomer may have exact sequence complementarity within the target sequence or near complementarity. Such antisense oligomers may block or inhibit translation of the mRNA containing the target sequence, or inhibit gene transcription. Antisense oligomers may bind to double-stranded or single-stranded sequences.

Examples of antisense oligonucleotides suitable for use in the practice of the present invention include, for example, those mentioned in the following reviews: R. A Stahel et al., Lung Cancer, 2003, 41: S81-S88; K. F. Pirollo et al., Pharmacol. Ther., 2003, 99: 55-77; A. C. Stephens and R. P. Rivers, Curr. Opin. Mol. Ther., 2003, 5: 118-122; N. M. Dean and C. F. Bennett, Oncogene, 2003, 22: 9087-9096; N. Schiavone et al., Curr. Pharm. Des., 2004, 10: 769-784; L. Vidal et al., Eur. J. Cancer, 2005, 41: 2812-2818; T. Aboul-Fadl, Curr. Med. Chem., 2005, 12: 2193-2214; M. E. Gleave and B. P. Monia, Nat. Rev. Cancer, 2005, 5: 468-479; Y. S. Cho-Chung, Curr. Pharm. Des., 2005, 11: 2811-2823; E. Rayburn et al., Lett. Drug Design & Discov., 2005, 2: 1-18; E. R. Rayburn et al., Expert Opin. Emerg. Drugs, 2006, 11: 337-352; I. Tamm and M. Wagner, Mol. Biotechnol., 2006, 33: 221-238 (each of which is incorporated herein by reference in its entirety).

Examples of suitable antisense oligonucleotides include, for example oblimersen sodium (also known as Genasense™ or G31239, developed by Genta, Inc., Berkeley Heights, N.J.), a phosphorothioate oligomer targeted towards the initiation codon region of the bcl-2 mRNA. Bcl-2 is a potent inhibitor of apoptosis and is overexpressed in many cancer including follicular lymphomas, breast cancer, colon cancer, prostate cancer, and intermediate/high-grade lymphomas (C. A. Stein et al., Semin. Oncol., 2005, 32: 563-573; S. R. Frankel, Semin. Oncol., 2003, 30: 300-304). Other suitable antisense oligonucleotides include GEM-231 (HYB0165, Hybridon, Inc., Cambridge, Mass.), which is a mixed backbone oligonucleotide directed against cAMP-dependent protein kinase A (PKA) (S. Goel et al., Clin. Cancer Res., 203, 9: 4069-4076); Affinitak (ISIS 3521 or aprinocarsen, ISIS pharmaceuticals, Inc., Carlsbad, Calif.), an antisense inhibitor of PKCalpha; OGX-011 (Isis 112989, Isis Pharmaceuticals, Inc.), a 2'-methoxyethyl modified antisense oligonucleotide against clusterin, a glycoprotein implicated in the regulation of the cell cycle, tissue remodeling, lipid transport, and cell death and which is overexpressed in cancers of breast, prostate and colon; ISIS 5132 (Isis 112989, Isis Pharmaceuticals, Inc.), a phosphorothioate oligonucleotide complementary to a sequence of the 3'-unstranslated region of the c-raf-1 mRNA (S. P. Henry et al., Anticancer Drug Des., 1997, 12: 409-420; B. P. Monia et al., Proc. Natl. Acad. Sci. USA, 1996, 93: 15481-15484; C. M. Rudin et al., Clin. Cancer Res., 2001, 7: 1214-1220); ISIS 2503 (Isis Pharmaceuticals, Inc.), a phosphorothioate oligonucleotide antisense inhibitor of human H-ras mRNA expression (J. Kurreck, Eur. J. Biochem., 2003, 270: 1628-1644); oligonucleotides targeting the X-linked inhibitor of apoptosis protein (XIAP), which blocks a substantial portion of the apoptosis pathway, such as GEM 640 (AEG 35156, Aegera Therapeutics Inc. and Hybridon, Inc.) or targeting survivin, an inhibitor of apoptosis protein (IAP), such as ISIS 23722 (Isis Pharmaceuticals, Inc.), a 2'-O-methoxyethyl chimeric oligonucleotide; MG98, which targets DNA methyl transferase; and GTI-2040 (Lorus Therapeutics, Inc. Toronto, Canada), a 20-mer oligonucleotide that is complementary to a coding region in the mRNA of the R2 small subunit component of human ribonucleotide reductase.

Other suitable antisense oligonucleotides include antisense oligonucleotides that are being developed against Her-2/neu, c-Myb, c-Myc, and c-Raf (see, for example, A. Biroccio et al., Oncogene, 2003, 22: 6579-6588; Y. Lee et al., Cancer Res., 2003, 63: 2802-2811; B. Lu et al., Cancer Res., 2004, 64: 2840-2845; K. F. Pirollo et al., Pharmacol. Ther., 2003, 99: 55-77; and A. Rait et al., Ann. N. Y. Acad. Sci., 2003, 1002: 78-89).

In certain embodiments, conjugates of the present invention comprise a nucleic acid anti-cancer agent that comprises or encodes an interfering RNA molecule. The terms "interfering RNA" and "interfering RNA molecule" are used herein interchangeably, and refer to an RNA molecule that can inhibit or downregulate gene expression or silence a gene in a sequence-specific manner, for example by mediating RNA interference (RNAi). RNA interference (RNAi) is an evolutionarily conserved, sequence-specific mechanism triggered by double-stranded RNA (dsRNA) that induces degradation of complementary target single-stranded mRNA and "silencing" of the corresponding translated sequences (McManus and Sharp, 2002, Nature Rev. Genet., 2002, 3: 737). RNAi functions by enzymatic cleavage of longer dsRNA strands into biologically active "short-interfering RNA" (siRNA) sequences of about 21-23 nucleotides in length (Elbashir et al., Genes Dev., 2001, 15: 188). RNA interference has emerged as a promising approach for therapy of cancer.

An interfering RNA suitable for use in the practice of the present invention can be provided in any of several forms. For example, an interfering RNA can be provided as one or more of an isolated short interfering RNA (siRNA), double-stranded RNA (dsRNA), micro-RNA (miRNA), or short hairpin RNA (shRNA).

Examples of interfering RNA molecules suitable for use in the present invention include, for example, the iRNAs cited in the following reviews: O. Milhavet et al., Pharmacol. Rev., 2003, 55: 629-648; F. Bi et al., Curr. Gene. Ther., 2003, 3: 411-417; P. Y. Lu et al., Curr. Opin. Mol. Ther., 2003, 5: 225-234; I. Friedrich et al., Semin. Cancer Biol., 2004, 14: 223-230; M. Izquierdo, Cancer Gene Ther., 2005, 12: 217-227; P. Y. Lu et al., Adv. Genet., 2005, 54: 117-142; G. R. Devi, Cancer Gene Ther., 2006, 13: 819-829; M. A. Behlke, Mol. Ther., 2006, 13: 644-670; and L. N. Putral et al., Drug News Perspect., 2006, 19: 317-324 (the contents of each of which are incorporated herein by reference in their entirety).

Other examples of suitable interfering RNA molecules include, but are not limited to, p53 interfering RNAs (e.g., T. R. Brummelkamp et al., Science, 2002, 296: 550-553; M. T. Hemman et al., Nat. Genet., 2003, 33: 396-400); interfering RNAs that target the bcr-abl fusion, which is associated with development of chronic myeloid leukemia and acute lymphoblastic leukemia (e.g., M. Scherr et al., Blood, 2003, 101: 1566-1569; M. J. Li et al., Oligonucleotides, 2003, 13: 401-409), interfering RNAs that inhibit expression of NPM-ALK, a protein that is found in 75% of anaplastic large cell lymphomas and leads to expression of a constitutively active kinase associated with tumor formation (U. Ritter et al., Oligonucleotides, 2003, 13: 365-373); interfering RNAs that target oncogenes, such as Raf-1 (T. F. Lou et al., Oligonucleotides, 2003, 13: 313-324), K-Ras (T. R. Brummelkamp et al., Cancer Cell, 2002, 2: 243-247), erbB-2 (G. Yang et al., J. Biol. Chem., 2004, 279: 4339-4345); interfering RNAs that target b-catenin protein, whose over-expression leads to transactivation of the T-cell factor target genes, which is thought to be the main transforming event in colorectal cancer (M. van de Wetering et al., EMBO Rep., 2003, 4: 609-615).

In certain embodiments, conjugates of the present invention comprise a nucleic acid therapeutic agent that is a ribozyme. As used herein, the term "ribozyme" refers to a catalytic RNA molecule that can cleave other RNA molecules in a target-specific marmer Ribozymes can be used to downregulate the expression of any undesirable products of genes of interest. Examples of ribozymes that can be used in the practice of the present invention include, but are not limited to, ANGIOZYME™ (RPI.4610, Sima Therapeutics, Boulder, Colo.), a ribozyme targeting the conserved region of human, mouse, and rat vascular endothelial growth factor receptor (VEGFR)-1 mRNA, and Herzyme (Sima Therapeutics).

In certain embodiments, entities or moieties within conjugates of the invention comprise a photosensitizer used in photodynamic therapy (PDT). In PDT, local or systemic administration of a photosensitizer to a patient is followed by irradiation with light that is absorbed by the photosensitizer in the tissue or organ to be treated. Light absorption by the photosensitizer generates reactive species (e.g., radicals) that are detrimental to cells. For maximal efficacy, a photosensitizer typically is in a form suitable for administration, and also in a form that can readily undergo cellular internalization at the target site, often with some degree of selectivity over normal tissues.

While some photosensitizers (e.g., Photofrin®, QLT, Inc., Vancouver, BC, Canada) have been delivered successfully as part of a simple aqueous solution, such aqueous solutions may not be suitable for hydrophobic photosensitizer drugs, such as those that have a tetra- or poly-pyrrole-based structure. These drugs have an inherent tendency to aggregate by molecular stacking, which results in a significant reduction in the efficacy of the photosensitization processes (Siggel et al., J. Phys. Chem., 1996, 100: 2070-2075). Approaches to minimize aggregation include liposomal formulations (e.g., for benzoporphyrin derivative monoacid A, BPDMA, Verteporfin®, QLT, Inc., Vancouver, Canada; and zinc phthalocyanine, CIBA-Geigy, Ltd., Basel, Switzerland), and conjugation of photosensitizers to biocompatible block copolymers (Peterson et al., Cancer Res., 1996, 56: 3980-3985) and/or antibodies (Omelyanenko et al., Int. J. Cancer, 1998, 75: 600-608).

Conjugates of the invention comprising a compound of the invention associated with a photosensitizer can be used as new delivery systems in PDT. In addition to reducing photosensitizer aggregation, delivery of photosensitizers according to the present invention exhibits other advantages such as increased specificity for target tissues/organ and cellular internalization of the photosensitizer.

Photosensitizers suitable for use in the present invention include any of a variety of synthetic and naturally occurring molecules that have photosensitizing properties useful in PDT. In certain embodiments, the absorption spectrum of the photosensitizer is in the visible range, typically between 350 nm and 1200 nm, preferably between 400 nm and 900 nm, e.g., between 600 nm and 900 nm. Suitable photosensitizers that can be coupled to toxins according to the present invention include, but are not limited to, porphyrins and porphyrin derivatives (e.g., chlorins, bacteriochlorins, isobacteriochlorins, phthalocyanines, and naphthalocyanines); metalloporphyrins, metallophthalocyanines, angelicins, chalcogenapyrrillium dyes, chlorophylls, coumarins, flavins and related compounds such as alloxazine and riboflavin, fullerenes, pheophorbides, pyropheophorbides, cyanines (e.g., merocyanine 540), pheophytins, sapphyrins, texaphyrins, purpurins, porphycenes, phenothiaziniums, methylene blue derivatives, naphthalimides, nile blue derivatives, quinones, perylenequinones (e.g., hypericins, hypocrellins, and cercosporins), psoralens, quinones, retinoids, rhodamines, thiophenes, verdins, xanthene dyes (e.g., eosins, erythrosins, rose bengals), dimeric and oligomeric forms of porphyrins, and prodrugs such as 5-aminolevulinic acid (R. W. Redmond and J. N. Gamlin, Photochem. Photobiol., 1999, 70: 391-475).

Exemplary photosensitizers suitable for use in the present invention include those described in U.S. Pat. Nos. 5,171,741; 5,171,749; 5,173,504; 5,308,608; 5,405,957; 5,512,675; 5,726,304; 5,831,088; 5,929,105; and 5,880,145 (the contents of each of which are incorporated herein by reference in their entirety).

In certain embodiments, conjugates of the invention comprise a radiosensitizer. As used herein, the term "radiosensitizer" refers to a molecule, compound or agent that makes tumor cells more sensitive to radiation therapy. Administration of a radiosensitizer to a patient receiving radiation therapy generally results in enhancement of the effects of radiation therapy. Ideally, a radiosensitizer exerts its function only on target cells. For ease of use, a radiosensitizer should also be able to find target cells even if it is administered systemically. However, currently available radiosensitizers are typically not selective for tumors, and they are distributed by diffusion in a mammalian body. Conjugates of the present invention can be used as a new delivery system for radiosensitizers.

A variety of radiosensitizers are known in the art. Examples of radiosensitizers suitable for use in the present invention include, but are not limited to, paclitaxel (TAXOL), carboplatin, cisplatin, and oxaliplatin (Amorino et al., Radiat. Oncol. Investig. 1999; 7: 343-352; Choy, Oncology, 1999, 13: 22-38; Safran et al., Cancer Invest., 2001, 19: 1-7; Dionet et al., Anticancer Res., 2002, 22: 721-725; Cividalli et al., Radiat. Oncol. Biol. Phys., 2002, 52: 1092-1098); gemcitabine (Gemzar®) (Choy, Oncology, 2000, 14: 7-14; Mornex and Girard, Annals of Oncology, 2006, 17: 1743-1747); etanidazole (NitroImidazole®) (Inanami et al., Int. J. Radiat. Biol., 2002, 78: 267-274); misonidazole (Tamulevicius et al., Br. J. Radiology, 1981, 54: 318-324; Palcic et al., Radiat. Res., 1984, 100: 340-347), tirapazamine (Masunaga et al., Br. J. Radiol., 2006, 79: 991-998; Rischin et al., J. Clin. Oncol., 2001, 19: 535-542; Shulman et al., Int. J. Radiat. Oncol. Biol. Phys., 1999, 44: 349-353); and nucleic acid base derivatives, e.g., halogenated purines or pyrimidines, such as 5-fluorodeoxyuridine (Buchholz et al., Int. J. Radiat. Oncol. Biol. Phys., 1995, 32: 1053-1058).

In certain embodiments, conjugates of the invention comprise a radioisotope. Examples of suitable radioisotopes include any α-, β- or γ-emitter, which, when localized at a tumor site, results in cell destruction (S. E. Order, "Analysis, Results, and Future Prospective of the Therapeutic Use of Radiolabeled Antibody in Cancer Therapy", Monoclonal Antibodies for Cancer Detection and Therapy, R. W. Baldwin et al. (Eds.), Academic Press, 1985). Examples of such radioisotopes include, but are not limited to, iodine-131 ($^{131}$I), iodine-125 ($^{125}$I), bismuth-212 ($^{212}$Bi), bismuth-213 ($^{213}$Bi), astatine-211 ($^{211}$At), rhenium-186 ($^{186}$Re), rhenium-188 ($^{188}$Re), phosphorus-32 ($^{32}$P), yttrium-90 ($^{90}$yY), samarium-153 ($^{153}$Sm), and lutetium-177 ($^{177}$Lu).

In certain embodiments, conjugates of the invention comprise a superantigen or biologically active portion thereof. Superantigens constitute a group of bacterial and viral proteins that are extremely efficient in activating a large fraction of the T-cell population. Superantigens bind directly to the major histocompatibility complex (MHC) without being processed. In fact, superantigens bind unprocessed outside the antigenbinding groove on the MHC class II molecules, thereby avoiding most of the polymorphism in the conventional peptide-binding site.

A superantigen-based tumor therapeutic approach has been developed for the treatment of solid tumors. In this approach, a targeting moiety, for example, an antibody or antibody fragment, is conjugated to a superantigen, providing a targeted superantigen. If the antibody, or antibody fragment, recognizes a tumor-associated antigen, the targeted superantigen, bound to tumors cells, can trigger superantigen-activated cytotoxic T-cells to kill the tumor cells directly by superantigen-dependent cell mediated cytotoxicity. (See, e.g., Søgaard et al., (1996) "Antibody-targeted superantigens in cancer immunotherapy," Immunotechnology, 2(3): 151-162, the entire contents of which are herein incorporated by reference.)

Superantigen-based tumor therapeutics have had some success. For example, fusion proteins with wild-type staphylococcal enterotoxin A (SEA) have been investigated in clinical trials of colorectal and pancreatic cancer (Giantonio et al., J. Clin. Oncol., 1997, 15: 1994-2007; Alpaugh et a., Cancer Res., 1998, 4: 1903-1914; Cheng et al., J. Clin. Oncol., 2004, 22: 602-609; the entire contents of each of which are herein incorporated by reference); staphylococcal superantigens of the enterotoxin gene cluster (egc) have been studied for the treatment of non-small cell lung cancer (Terman et al., Clin. Chest Med., 2006, 27: 321-324, the entire contents of which are herein incorporated by reference), and staphylococcal enterotoxin B has been evaluated for the intravesical immunotherapy of superficial bladder cancer (Perabo et al., Int. J. Cancer, 2005, 115: 591-598, the entire contents of which are herein incorporated by reference).

A superantigen, or a biologically active portion thereof, can be associated to a compound of the invention to form a conjugate according to the present invention and used in a therapy, e.g., an anti-cancer therapy, as described herein.

Examples of superantigens suitable for use in the present invention include, but are not limited to, staphylococcal enterotoxin (SE) (e.g., staphylococcal enterotoxin A (SEA) or staphylococcal enterotoxin E (SEE)), *Streptococcus pyogenes* exotoxin (SPE), *Staphylococcus aureus* toxic shock-syndrome toxin (TSST-1), streptococcal mitogenic exotoxin (SME), streptococcal superantigen (SSA), and staphylococcal superantigens of the enterotoxin gene cluster. As known to one skilled in the art, the three-dimensional structures of the above listed superantigens can be obtained from the Protein Data Bank. Similarly, the nucleic acid sequences and the amino acid sequences of the above listed superantigens and other superantigens can be obtained from GenBank.

In certain embodiments, a conjugate of the present invention may be used in directed enzyme prodrug therapy. In a directed enzyme prodrug therapy approach, a directed/targeted enzyme and a prodrug are administered to a subject, wherein the targeted enzyme is specifically localized to a portion of the subject's body where it converts the prodrug into an active drug. The prodrug can be converted to an active drug in one step (by the targeted enzyme) or in more than one step. For example, the prodrug can be converted to a precursor of an active drug by the targeted enzyme. The precursor can then be converted into the active drug by, for example, the catalytic activity of one or more additional targeted enzymes, one or more non-targeted enzymes administered to the subject, one or more enzymes naturally present in the subject or at the target site in the subject (e.g., a protease, phosphatase, kinase or polymerase), by an agent that is administered to the subject, and/or by a chemical process that is not enzymatically catalyzed (e.g., oxidation, hydrolysis, isomerization, epimerization, etc.).

Different approaches have been used to direct/target the enzyme to the site of interest. For example, in ADEPT (antibody-directed enzyme prodrug therapy), an antibody designed/developed against a tumor antigen is linked to an enzyme and injected in a subject, resulting in selective binding of the enzyme to the tumor. When the discrimination between tumor and normal tissue enzyme levels is sufficient, a prodrug is administered to the subject. The prodrug is converted to its active form by the enzyme only within the tumor. Selectivity is achieved by the tumor specificity of the antibody and by delaying prodrug administration until there is a large differential between tumor and normal tissue enzyme levels. Early clinical trials are promising and indicate that ADEPT may become an effective treatment for all solid cancers for which tumor-associated or tumor-specific antibodies are known. Tumors have also been targeted with the genes encoding for prodrug activating enzymes. This approach has been called virus-directed enzyme prodrug therapy (VDEPT) or more generally GDEPT (gene-directed enzyme prodrug therapy, and has shown good results in laboratory systems. Other versions of directed enzyme prodrug therapy include PDEPT (polymer-directed enzyme prodrug therapy), LEAPT (lectin-directed enzyme-activated prodrug therapy), and CDEPT (clostridial-directed enzyme prodrug therapy). A conjugate according to the present invention, which comprises a prodrug activating enzyme associated with a compound of the invention, can be used in a similar way.

Nonlimiting examples of enzyme/prodrug/active drug combinations suitable for use in the present invention are described, for example, in Bagshawe et al., Current Opinions in Immunology, 1999, 11: 579-583; Wilman, "Prodrugs in Cancer Therapy", Biochemical Society Transactions, 14: 375-382, 615$^{th}$ Meeting, Belfast, 1986; Stella et al., "*Prodrugs: A Chemical Approach To Targeted Drug Delivery*", in "*Directed Drug Delivery*", Borchardt et al., (Eds), pp. 247-267 (Humana Press, 1985). Nonlimiting examples of enzyme/prodrug/active anti-cancer drug combinations are described, for example, in Rooseboom et al., Pharmacol. Reviews, 2004, 56: 53-102.

Examples of prodrug activating enzymes include, but are not limited to, nitroreductase, cytochrome P450, purine-nucleoside phosphorylase, thymidine kinase, alkaline phosphatase, β-glucuronidase, carboxypeptidase, penicillin amidase, β-lactamase, cytosine deaminase, and methionine γ-lyase.

Examples of anti-cancer drugs that can be formed in vivo by activation of a prodrug by a prodrug activating enzyme include, but are not limited to, 5-(aziridin-1-yl)-4-hydroxyl-amino-2-nitro-benzamide, isophosphoramide mustard, phosphoramide mustard, 2-fluoroadenine, 6-methylpurine, ganciclovir-triphosphate nucleotide, etoposide, mitomycin C, p-[N,N-bis(2-chloroethyl)amino]phenol (POM), doxorubicin, oxazolidinone, 9-aminocamptothecin, mustard, methotrexate, benzoic acid mustard, doxorubicin, adriamycin, daunomycin, carminomycin, bleomycins, esperamicins, melphalan, palytoxin, 4-desacetylvinblastine-3-carboxylic acid hydrazide, phenylenediamine mustard, 4'-carboxyphthalato (1,2-cyclohexane-diamine) platinum, taxol, 5-fluorouracil, methylselenol, and carbonothionic difluoride.

In certain embodiments, a therapeutic (e.g., anti-cancer) agent within a conjugate of the present invention comprises an anti-angiogenic agent. Antiangiogenic agents suitable for use in the present invention include any molecule, compound, or factor that blocks, inhibits, slows down, or reduces the process of angiogenesis, or the process by which new blood vessels form by developing from preexisting vessels. Such a molecule, compound, or factor can block angiogenesis by blocking, inhibiting, slowing down, or reducing any of the steps involved in angiogenesis, including (but not limited to) steps of (1) dissolution of the membrane of the originating vessel, (2) migration and proliferation of endothelial cells, and (3) formation of new vasculature by migrating cells.

Examples of anti-angiogenic agents include, but are not limited to, bevacizumab (AVASTIN®), celecoxib (CELEBREX®), endostatin, thalidomide, EMD121974 (Cilengitide), TNP-470, squalamine, combretastatin A4, interferon-α, anti-VEGF antibody, SU5416, SU6668, PTK787/2K 22584, Marimistal, AG3340, COL-3, Neovastat, and BMS-275291.

Anti-angiogenic agents may be used in a variety of therapeutic contexts, including, but not limited to, anti-cancer therapies and therapies for macular degeneration.

As will be recognized by one skilled in the art, the specific examples of therapeutic agents cited herein represent only a very small number of the therapeutic agents that are suitable for use in the practice of the present invention.

Detection Entities

Multifunctional agents described herein in many embodiments comprise at least one detection entity, in addition to a targeting entity described above.

A detection entity may be any entity that allows detection of a targeting agent after binding to a tissue or localization at a system of interest. Any of a wide variety of detectable agents can be used as detection entity (e.g., labeling moieties) in multifunctional conjugate agents of the present invention. A detection entity may be directly detectable or indirectly detectable. Examples of detection entity include, but are not limited to: various ligands, radionuclides (e.g., $^{3}$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99m}$Tc, $^{177}$Lu, etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

In certain embodiments, a detection entity comprises a fluorescent label. Numerous known fluorescent labeling moieties of a wide variety of chemical structures and physical characteristics are suitable for use in the practice of methods of diagnosis of the present invention. Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514., etc.), Texas Red, Texas Red-X, Spectrum Red™, Spectrum Green™, cyanine dyes (e.g., Cy-3™, Cy-5™, Cy-3.5™, Cy-5.5™ etc.), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660, Alexa Fluor 680, etc.), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", 9$^{111}$Ed., Molecular Probes, Inc., Eugene, Oreg.

Favorable properties of fluorescent labeling agents include high molar absorption coefficient, high fluorescence quantum yield, and photostability. In certain embodiments, labeling fluorophores desirably exhibit absorption and emission wavelengths in the visible (i.e., between 400 and 750 nm) rather than in the ultraviolet range of the spectrum (i.e., lower than 400 nm).

In certain embodiments, a detection entity comprises an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a targeting entity (e.g., compound of the invention of formula I) using a linker group such as a carbodiimide, a diisocyanate, a glutaraldehyde, and the like. More detailed description of suitable linkers is provided elsewhere herein.

In certain embodiments, a detection entity comprises a radioisotope that is detectable by Single Photon Emission Computed Tomography (SPECT) or Position Emission Tomography (PET). Examples of such radionuclides include, but are not limited to, iodine-131 ($^{131}$I), iodine-125 ($^{125}$I), bismuth-212 ($^{212}$Bi), bismuth-213 ($^{213}$Bi), astatine-221 ($^{211}$At), copper-67 ($^{67}$Cu), copper-64 ($^{64}$Cu), rhenium-186 ($^{186}$Re), rhenium-186 ($^{188}$Re), phosphorus-32 ($^{32}$P), samarium-153 ($^{153}$Sm), lutetium-177 ($^{117}$Lu) technetium-99m ($^{99m}$Tc), gallium-67 ($^{67}$Ga), indium-I11 ($^{111}$In), and thallium-201 ($^{201}$Tl).

In certain embodiments, a labeling moiety comprises a radioisotope that is detectable by Gamma camera. Examples of such radioisotopes include, but are not limited to, iodine-131 ($^{131}$I), and technetium-99m ($^{99m}$Tc).

In certain embodiments, a detection entity comprises a paramagnetic metal ion that is a good contrast enhancer in Magnetic Resonance Imaging (MRI). Examples of such paramagnetic metal ions include, but are not limited to, gadolinium III ($Gd^{3+}$), chromium III ($Cr^{3+}$), dysprosium III ($Dy^{3+}$), iron III ($Fe^{3+}$), manganese II ($Mn^{2+}$), and ytterbium III ($Yb^{3+}$). In certain embodiments, the detection entity comprises gadolinium III ($Gd^{3+}$). Gadolinium is an FDA-approved contrast agent for MRI, which accumulates in abnormal tissues causing these abnormal areas to become very bright (enhanced) on the magnetic resonance image. Gadolinium is known to provide great contrast between normal and abnormal tissues in different areas of the body, in particular in the brain.

In certain embodiments, a labeling moiety comprises a stable paramagnetic isotope detectable by nuclear magnetic resonance spectroscopy (MRS). Examples of suitable stable paramagnetic isotopes include, but are not limited to, carbon-13 ($^{13}$C) and fluorine-19 ($^{19}$F).

Conjugation

As stated above, multifunctional agents described herein comprise multiple entities, each having at least one function. As already noted, certain embodiments of contemplated multifunctional agents comprise a targeting entity and at least one of the following entities: a detection entity and a therapeutic entity. In some embodiments, a multifunctional agent of the invention contains a targeting entity and a therapeutic entity; but not a detection entity. In some embodiments, a multifunctional agent of the invention contains a targeting entity; a detection entity; but not a therapeutic entity. In some embodiments, a multifunctional agent of the invention contains a targeting entity; a therapeutic entity; and a detection entity. In any of contemplated embodiments, the entities of an agent are conjugated to one another. Conjugation of various entities to form a multifunctional agent is not limited to particular modes of conjugation. For example, two entities may be covalently conjugated directly to each other. Alternatively, two entities may be indirectly conjugated to each other, such as via a linker entity. In some embodiments, a multifunctional agent may include different types of conjugation within the agent, such that some entities of the agent are conjugated via direct conjugation while other entities of the agent are indirectly conjugated via one or more linkers. In some embodiments, a multifunctional agent of the invention comprises a single type of a linker entity. In other embodiments, a multifunctional agent of the invention comprises more than one types of a linker entities. In some embodiments, a multifunctional agent includes a single type of linker entities but of varying length.

In many of the embodiments described herein, association between or amongst entities contained in a multifunctional agent is covalent. As will be appreciated by one skilled in the art, the moieties may be attached to each other either directly or indirectly (e.g., through a linker, as described above).

In certain embodiments, where one entity (such as a targeting entity) and a second entity of a multifunctional agent are directly covalently linked to each other, such direct covalent conjugation can be through a linkage (e.g., a linker or linking entity) such as an amide, ester, carbon-carbon, disulfide, carbamate, ether, thioether, urea, amine, or carbonate linkage. Covalent conjugation can be achieved by taking advantage of functional groups present on the first entity and/or the second entity of the multifunctional agent. Alternatively, a non-critical amino acid may be replaced by another amino acid that will introduce a useful group (such as amino, carboxy or sulfhydryl) for coupling purposes. Alternatively, an additional amino acid may be added to at least one of the entities of the multifunctional agent to introduce a useful group (such as amino, carboxy or sulfhydryl) for coupling purposes. Suitable functional groups that can be used to attach moieties together include, but are not limited to, amines, anhydrides, hydroxyl groups, carboxy groups, thiols, and the like. An activating agent, such as a carbodiimide, can be used to form a direct linkage. A wide variety of activating agents are known in the art and are suitable for conjugating one entity to a second entity.

In other embodiments, entities of a multifunctional agent embraced by the present invention are indirectly covalently linked to each other via a linker group. Such a linker group may also be referred to as a linker or a linking entity. This can be accomplished by using any number of stable bifunctional agents well known in the art, including homofunctional and heterofunctional agents (for examples of such agents, see, e.g., Pierce Catalog and Handbook). The use of a bifunctional linker differs from the use of an activating agent in that the former results in a linking moiety being present in the resulting conjugate (agent), whereas the latter results in a direct coupling between the two moieties involved in the reaction. The role of a bifunctional linker may be to allow reaction between two otherwise inert moieties. Alternatively or additionally, the bifunctional linker that becomes part of the reaction product may be selected such that it confers some degree of conformational flexibility to the targeting agent in relation to the detecting moiety (e.g., the bifunctional linker comprises a straight alkyl chain containing several atoms, for example, the straight alkyl chain contains between 2 and 10 carbon atoms). Alternatively or additionally, the bifunctional linker may be selected such that the linkage formed between a targeting agent and therapeutic agent is cleavable, e.g. hydrolysable (for examples of such linkers, see e.g. U.S. Pat. Nos. 5,773,001; 5,739,116 and 5,877,296, each of which is incorporated herein by reference in its entirety). Such linkers, for example, may be used when higher activity of certain entities, such as a targeting agent (e.g., compound of formula I) and/or of a therapeutic entity is observed after hydrolysis of the conjugate. Exemplary mechanisms by which an entity may be cleaved from a multifunctional agent include hydrolysis in the acidic pH of the lysosomes (hydrazones, acetals, and cis-aconitate-like amides), peptide cleavage by lysosomal enzymes (the capthepsins and other lysosomal enzymes), and reduction of disulfides). Another mechanism by which such an entity is cleaved from the multifunctional agent includes hydrolysis at physiological pH extra- or intra-cellularly. This mechanism applies when the crosslinker used to couple one entity to another entity is a biodegradable/bioerodible component, such as polydextran and the like.

For example, hydrazone-containing multifunctional agents can be made with introduced carbonyl groups that provide the desired release properties. Multifunctional agents can also be made with a linker that comprise an alkyl chain with a disulfide group at one end and a hydrazine derivative at the other end. Linkers containing functional groups other than hydrazones also have the potential to be cleaved in the acidic milieu of lysosomes. For example, multifunctional agents can be made from thiol-reactive linkers that contain a group other than a hydrazone that is cleavable intracellularly, such as esters, amides, and acetals/ketals.

Another example of class of pH sensitive linkers are the cis-aconitates, which have a carboxylic acid group juxtaposed to an amide group. The carboxylic acid accelerates amide hydrolysis in the acidic lysosomes. Linkers that achieve a similar type of hydrolysis rate acceleration with several other types of structures can also be used.

Another potential release method for targeting agents is the enzymatic hydrolysis of peptides by the lysosomal enzymes. In one example, a peptidic toxin is attached via an amide bond to para-aminobenzyl alcohol and then a carbamate or carbonate is made between the benzyl alcohol and the therapeutic agent. Cleavage of the peptide leads to collapse of the amino benzyl carbamate or carbonate, and release of the therapeutic agent. In another example, a phenol can be cleaved by collapse of the linker instead of the carbamate. In another variation, disulfide reduction is used to initiate the collapse of a para-mercaptobenzyl carbamate or carbonate.

Useful linkers which may be used as a linking entity of a multifunctional agent provided herein include, without limitation: polyethylene glycol, a copolymer of ethylene glycol, a polypropylene glycol, a copolymer of propylene glycol, a carboxymethylcellulose, a polyvinyl pyrrolidone, a poly-1,3-dioxolane, a poly-1,3,6-trioxane, an ethylene/maleic anhydride copolymer, a polyaminoacid, a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polyacetal, a long chain fatty acid, a long chain hydrophobic aliphatic group.

Embraced also herein are multifunctional agents that include at least one entity which involves non-covalent association. Examples of non-covalent interactions include, but are not limited to, hydrophobic interactions, electrostatic interactions, dipole interactions, van der Waals interactions, and hydrogen bonding. Irrespective of the nature of the binding, interaction, or coupling, the association between a first entity and a second entity is, in some embodiments, selective, specific and strong enough so that the second entity contained in the agent does not dissociate from the first entity before or during transport/delivery to and into the target. Thus, Association amongst multiple entities of a multifunctional agent may be achieved using any chemical, biochemical, enzymatic, or genetic coupling known to one skilled in the art.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

In certain embodiments, compounds of formula I are prepared according to the procedure outlined in Scheme 1.

Scheme 1

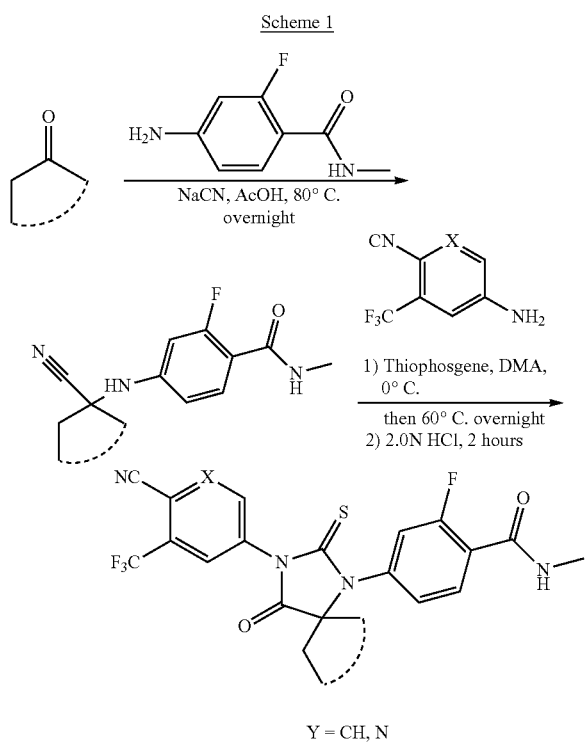

Y = CH, N

The syntheses were executed according to a general scheme starting from a given ketone and reacting it under Strecker reaction conditions, using sodium cyanide and 4-amino-2-fluoro-N-methylbenzamide. The resulting cyanamine was then reacted with 4-cyano-3-trifluoromethylaniline (X=CH) or a 2-cyano-3-trifluoromethyl-5-aminopyridine (X=N) in the present of thiophosgene to give the desired thiohydantoins after acid hydrolysis of the intermediate imine.

Example 1

Strecker Reaction

A general procedure for the first step of the synthesis of compounds of formula I follows. To a mixture of 4-amino-2-fluoro-N-methylbenzamide (0.3 mmol) and desired ketone (1.0-2.0 eq) in glacial acetic acid (2 mL) was added NaCN (100 mg, 2.0 mmol, 7.0 eq), and the mixture was heated to 80° C. overnight. The solvent was then removed under reduced pressure and the residue was dissolved in water (20 mL), then pH was brought to neutrality with aqueous saturated NaHCO$_3$ solution. The mixture was extracted with ethyl acetate (3×50 mL), and the combined organic layers were dried over anhydrous Na$_2$SO$_4$. The solution was filtered and concentrated under reduced pressure and the resulting residue was chromatographed on a short path silica gel column using the gradient hexane/ethyl acetate 2/1 to 1/1.5 (v/v) to yield each desired product in more than 85% yield.

Example 2

Thiohydantoin Synthesis

A general procedure for the second step of the synthesis of compounds of formula I follows. Thiophosgene (5.1 uL, 66 umol) was added dropwise to a solution of 5-amino-2-cyano-3-trifluoromethylpyridine or 4-amino-2-(trifluoromethyl) benzonitrile (60 umol) and the given Strecker products above N-methyl-4-(1-cyanocycloalkylamino)-2-fluorobenzamides (60 umol) in dry DMA (0.6 mL) under argon at 0° C. After 5 min, the solution was stirred overnight at 60 C. At room temperature, this mixture was then diluted with MeOH (1 mL) and aq. 2.0 N HCl (0.5 mL), and the reaction was brought to reflux for 2 hours. After cooling to ambient temperature, the reaction mixture was poured into ice water (10 mL) and extracted with EtOAc (3×20 mL). The combined organic layers were briefly dried over anhydrous Mg$_2$SO$_4$, concentrated and the resulting residue was chromatographed on silica gel using the gradient system hexane/ethyl acetate 2/1 to 1.5/1 (v/v) to yield the desired thiohydantoin in yields up to 90%.

The following non-limiting examples illustrate analytical data obtained for compounds of formula I produced by the synthesis of Scheme 1. Where a given compound can exist as two or more enantiomers or diastereomers, such isomers can be separated by techniques well known in the art such as HPLC. By way of example, preparative HPLC purifications can be carried out utilizing a Shimadzu [Prominence LC-20AP], equipped with a Chiralpak AGP column (50×21.2 mm, 50 utilizing the following method: Solvent A=Acetonitrile, Solvent B=Water; Gradient=95% solvent B to 10% solvent B over 20 min with a flow rate of 10 mL/min. Analytical LCMS data can be acquired using a Shimadzu [LCMS-2020] equipped with a SHIMPAK, XR ODS-II column (50×2 mm) utilizing the following method: Flow Rate=0.2 mL/min, Solvent A=Acetonitrile, Solvent B=0.1% TFA in water; Gradient=Initial 95% of solvent B to 10% solvent B over 10 min followed by 10% solvent B for an additional 10 min.

Analytical data for compound I-8: 4-(3-(4-cyano-3-(trifluoromethyl)phenyl)-4-oxo-2-thioxo-1,3-diazaspiro[4.4]nonan-1-yl)-2-fluoro-N-methylbenzamide.

This compound was isolated as an off-white foam. $^1$HNMR (CDCl3): 8.28 (t, 1 H, J=8.5 Hz), 7.79 (d, 1 H, J=8.3 Hz), 7.96 (bs, 1 H), 7.84 (dd, 1 H, J=8.3 Hz, J=1.5 Hz), 7.27 (dd, 1 H, J=8.3 Hz, J=1.8 Hz), 7.17 (dd, 1 H, J=11.7 Hz, J=1.5 Hz), 6.71 (m, 1 H), 3.07 (d, 3 H, J=4.7 Hz), 2.36 (m, 2 H), 2.16 (m, 2 H), 1.91 (m, 2 H), 1.56 (m, 2 H). $^{19}$FNMR (CDCl$_3$): −61.98, −110.64. LRMS [M+H]+ found: 491.22; calculated: 491.12.

Analytical data for compound I-9: 4-(3-(4-cyano-3-(trifluoromethyl)phenyl)-4-oxo-2-thioxo-1,3-diazaspiro[4.5]decan-1-yl)-2-fluoro-N-methylbenzamide.

The compound was obtained as an off-white foam. $^1$HNMR (CDCl$_3$): 8.27 (t, 1 H, J=8.4 Hz), 7.98 (d, 1 H, J=8.3 Hz), 7.93 (bs, 1 H), 7.82 (dd, 1 H, J=8.2 Hz, J=1.6 Hz), 7.19 (dd, 1 H, J=8.3 Hz, J=1.8 Hz), 7.08 (dd, 1 H, J=11.6 Hz, J=1.6 Hz), 6.70 (m, 1 H), 3.08 (d, 3 H, J=4.7 Hz), 2.07 (m, 4 H), 1.70 (m, 6 H). $^{19}$FNMR (CDCl$_3$): −61.97, −110.92. LRMS [M+H]+ found: 505.30; calculated: 505.13.

Analytical data for compound I-10: 4-(3-(4-cyano-3-(trifluoromethyl)phenyl)-4-oxo-2-thioxo-1,3-diazaspiro[4.6]undecan-1-yl)-2-fluoro-N-methylbenzamide.

This compound was isolated as off-white solid. $^1$HNMR (CDCl$_3$): 8.28 (t, 1 H, J=8.4 Hz), 7.98 (d, 1 H, J=8.3 Hz), 7.93 (bs, 1 H), 7.82 (dd, 1 H, J=8.2 Hz, J=1.6 Hz), 7.24 (dd, 1 H, J=8.3 Hz, J=1.6 Hz), 7.14 (dd, 1 H, J=11.6 Hz, J=1.5 Hz), 6.72 (m, 1 H), 3.08 (d, 3 H, J=4.7 Hz), 2.28 (m, 2 H), 2.17 (m, 2 H), 1.81 (m, 2 H), 1.60 (m, 2 H), 1.44 (m, 2 H), 1.32 (m, 2 H). $^{19}$FNMR (CDCl$_3$): −61.98, −110.82. LRMS [M+H]+ found: 519.38; calculated: 519.15.

Analytical data for racemic compound I-1: 4-(3-(4-cyano-3-(trifluoromethyl)phenyl)-7,7-dimethyl-4-oxo-2-thioxo-1,3-diazaspiro[4.5]decan-1-yl)-2-fluoro-N-methylbenzamide.

This compound was synthesized in 70% overall yield as an off-white powder. $^1$HNMR (CDCl$_3$): 8.27 (t, 1 H, J=8.4 Hz), 7.98 (d, 1 H, J=8.3 Hz), 7.92 (bs, 1 H), 7.80 (dd, 1 H, J=8.2 Hz, J=1.7 Hz), 7.17 (dd, 1 H, J=8.3 Hz, J=1.7 Hz), 7.07 (dd, 1 H, J=11.6 Hz, J=1.6 Hz), 6.70 (m, 1 H), 3.08 (d, 3 H, J=4.7 Hz), 2.27 (m, 1 H), 2.17 (m, 1 H), 1.93 (m, 1 H), 1.67 (m, 1 H), 1.62 (m, 1 H), 1.57 (m, 1 H), 1.52 (m, 2 H), 1.20 (s, 3 H), 0.95 (s, 3 H). $^{19}$FNMR (CDCl$_3$): −61.98, −110.89. LRMS [M+H]+ found: 533.33; calculated: 533.17.

Analytical data for compound I-11: 4-(3-(4-cyano-3-(trifluoromethyl)phenyl)-8,8-dimethyl-4-oxo-2-thioxo-1,3-diazaspiro[4.5]decan-1-yl)-2-fluoro-N-methylbenzamide.

This compound was isolated as an off-white powder. $^1$HNMR (CDCl$_3$): 8.30 (t, 1 H, J=8.4 Hz), 7.98 (d, 1 H, J=8.3 Hz), 7.93 (bs, 1 H), 7.82 (dd, 1 H, J=8.2 Hz, J=1.6 Hz), 7.22 (dd, 1 H, J=8.3 Hz, J=1.6 Hz), 7.11 (dd, 1 H, J=11.6 Hz, J=1.5 Hz), 6.72 (m, 1 H), 3.08 (d, 3 H, J=4.7 Hz), 2.04 (m, 2 H), 1.93 (m, 4 H), 1.37 (m, 2 H), 0.99 (s, 3 H), 0.73 (s, 3 H). $^{19}$FNMR (CDCl$_3$): −61.98, −110.75. LRMS [M+H]+ found: 533.33; calculated: 533.17.

Analytical data for compound I-5: 4-(3-(4-cyano-3-(trifluoromethyl)phenyl)-7,7,9,9-tetramethyl-4-oxo-2-thioxo-1,3-diazaspiro[4.5]decan-1-yl)-2-fluoro-N-methylbenzamide.

This compound was isolated as a beige foam. $^1$HNMR (CDCl$_3$): 8.21 (t, 1 H, J=8.4 Hz), 7.90 (d, 1 H, J=8.3 Hz), 7.85 (bs, 1 H), 7.73 (dd, 1 H, J=8.2 Hz, J=1.2 Hz), 7.12 (dd, 1 H, J=8.3 Hz, J=1.2 Hz), 7.02 (dd, 1 H, J=11.6 Hz, J=1.2 Hz), 6.64 (m, 1 H), 3.01 (d, 3 H, J=4.7 Hz), 1.94 (d, 2H, J=14.4 Hz), 1.62 (d, 2H, J=14.4 Hz), 1.50 (s, 2 H), 1.17 (s, 6 H), 0.83 (s, 6 H). $^{19}$FNMR (CDCl$_3$): −61.98, −110.89. LRMS [M+H]+ found: 561.29; calculated: 561.20.

Analytical data for racemic compound I-3: 4-(3-(6-cyano-5-(trifluoromethyl)pyridin-3-yl)-7,7-dimethyl-4-oxo-2-thioxo-1,3-diazaspiro[4.5]decan-1-yl)-2-fluoro-N-methylbenzamide.

This compound was isolated as an off-white foam. $^1$HNMR (CDCl$_3$): 9.06 (d, 1 H, J=1.9 Hz), 8.33 (d, 1 H, J=1.9 Hz), 8.29 (t, 1 H, J=8.4 Hz), 7.18 (dd, 1 H, J=8.4 Hz, J=1.6 Hz), 7.07 (dd, 1 H, J=11.5 Hz, J=1.5 Hz), 6.71 (m, 1 H), 3.08 (d, 3 H, J=4.7 Hz), 2.30 (m, 1 H), 2.18 (m, 1 H), 1.94 (m, 1 H), 1.72 (m, 1 H), 1.63 (m, 1 H), 1.57 (m, 1 H), 1.52 (m, 2 H), 1.20 (s, 3 H), 0.94 (s, 3 H). $^{19}$FNMR (CDCl$_3$): −61.87, −110.71. LRMS [M+H]+ found: 534.31; calculated: 534.16.

Analytical data for compound I-26: 4-(3-(4-cyano-3-(trifluoromethyl)phenyl)-4-oxo-2-thioxoimidazolidin-1-yl)-2-fluoro-N-methylbenzamide.

This compound was isolated as a white to off-white powder. $^1$HNMR (CDCl$_3$): 8.26 (t, 1 H, J=8.4 Hz), 8.02 (d, 1 H, J=8.3 Hz), 7.91 (bs, 1 H), 7.79 (m, 2 H), 7.45 (dd, 1 H, J=10.7 Hz, J=1.3 Hz), 6.71 (m, 1 H), 4.71 (s, 2 H), 3.06 (d, 3 H, J=4.7 Hz). $^{19}$FNMR (CDCl$_3$): −62.05, −110.31. LRMS [M+H]+ found: 437.19; calculated: 437.07.

Analytical data for compound (+)-I-12: 4-(1-(4-cyano-3-(trifluoromethyl)phenyl)-5-oxo-2-thiooctahydro-1'H-spiro[imidazolidine-4,2'-naphthalen]-3-yl)-2-fluoro-N-methylbenzamide.

This compound was isolated as off-white foam. $^1$HNMR (CDCl$_3$): 8.30 (t, 1 H, J=8.4 Hz), 7.98 (d, 1 H, J=8.3 Hz), 7.93 (bs, 1 H), 7.82 (dd, 1 H, J=8.2 Hz, J=1.8 Hz), 7.21 (dd, 1 H, J=8.3 Hz, J=1.7 Hz), 7.11 (dd, 1 H, J=11.6 Hz, J=1.6 Hz), 6.73 (m, 1 H), 3.08 (d, 3 H, J=4.7 Hz), 2.62 (m, 1 H), 2.35 (m, 1 H), 2.10-1.09 (m, 14 H). $^{19}$FNMR (CDCl$_3$): −61.96, −110.72. LRMS [M+H]+ found: 559.32; calculated: 559.18.

Analytical data for compound I-13: 4-(3-(6-cyano-5-(trifluoromethyl)pyridin-3-yl)-4-oxo-2-thioxo-1,3-diazaspiro[4.4]nonan-1-yl)-2-fluoro-N-methylbenzamide.

This compound was isolated as off-white foam. $^1$HNMR (CDCl$_3$): 9.09 (d, 1 H, J=2.0 Hz), 8.35 (d, 1 H, J=1.9 Hz), 8.30 (t, 1 H, J=8.4 Hz), 7.27 (dd, 1 H, J=8.4 Hz, J=1.8 Hz), 7.17 (dd, 1 H, J=11.6 Hz, J=1.7 Hz), 6.71 (m, 1 H), 3.08 (d, 3 H, J=4.7 Hz), 2.37 (m, 2 H), 2.19 (m, 2 H), 1.92 (m, 2 H), 1.57 (m, 2 H). $^{19}$FNMR (CDCl$_3$): −61.87, −110.47. LRMS [M+H]+ found: 492.27; calculated: 492.11.

Analytical data for compound I-14: 4-(3-(6-cyano-5-(trifluoromethyl)pyridin-3-yl)-4-oxo-2-thioxo-1,3-diazaspiro[4.5]decan-1-yl)-2-fluoro-N-methylbenzamide.

This compound was obtained as off-white foam. $^1$HNMR (CDCl$_3$): 9.07 (d, 1 H, J=1.7 Hz), 8.33 (d, 1 H, J=1.7 Hz), 8.29 (t, 1 H, J=8.4 Hz), 7.19 (dd, 1 H, J=8.3 Hz, J=1.4 Hz), 7.17 (dd, 1 H, J=11.5 Hz, J=1.4 Hz), 6.70 (m, 1 H), 3.08 (d, 3 H, J=4.7 Hz), 2.09 (m, 4 H), 1.70 (m, 6 H). $^{19}$FNMR (CDCl$_3$): −61.87, −110.75. LRMS [M+H]+ found: 506.28; calculated: 506.13.

Analytical data for compound I-15: 4-(3-(6-cyano-5-(trifluoromethyl)pyridin-3-yl)-4-oxo-2-thioxo-1,3-diazaspiro[4.6]undecan-1-yl)-2-fluoro-N-methylbenzamide.

This compound was isolated as off-white foam. $^1$HNMR (CDCl$_3$): 9.06 (d, 1 H, J=1.9 Hz), 8.33 (d, 1 H, J=1.9 Hz), 8.29 (t, 1 H, J=8.4 Hz), 7.24 (dd, 1 H, J=8.4 Hz, J=1.6 Hz), 7.13 (dd, 1 H, J=11.5 Hz, J=1.5 Hz), 6.71 (m, 1 H), 3.08 (d, 3 H, J=4.7 Hz), 2.30 (m, 2 H), 2.18 (m, 2 H), 1.82 (m, 2 H), 1.61 (m, 2 H), 1.45 (m, 2 H), 1.32 (m, 2 H). $^{19}$FNMR (CDCl$_3$): −61.87, −110.47. LRMS [M+H]+ found: 520.30; calculated: 520.15.

Analytical data for compound I-16: 4-(3-(6-cyano-5-(trifluoromethyl)pyridin-3-yl)-8,8-dimethyl-4-oxo-2-thioxo-1,3-diazaspiro[4.5]decan-1-yl)-2-fluoro-N-methylbenzamide.

$^1$HNMR (CDCl3): 9.06 (d, 1H, J=1.7 Hz), 8.33 (d, 1H, J=1.7 Hz), 8.30 (t, 1 H, J=8.4 Hz), 7.22 (dd, 1 H, J=8.3 Hz, J=1.6 Hz), 7.11 (dd, 1 H, J=11.6 Hz, J=1.5 Hz), 6.72 (m, 1 H), 3.08 (d, 3 H, J=4.7 Hz), 2.04-1.94 (m, 6H), 1.37 (m, 2 H), 0.99 (s, 3 H), 0.73 (s, 3 H). $^{19}$FNMR (CDCl$_3$): −61.87, −110.57. LRMS [M+H]+ found: 534.31; calculated: 534.15.

Analytical data for compound (+)-I-17: 4-(1-(6-cyano-5-(trifluoromethyl)pyridin-3-yl)-5-oxo-2-thiooctahydro-1'H-spiro[imidazolidine-4,2'-naphthalen]-3-yl)-2-fluoro-N-methylbenzamide.

This compound was obtained as off-white foam. $^1$HNMR (CDCl$_3$): 9.06 (d, 1 H, J=1.9 Hz), 8.32 (d, 1 H, J=1.9 Hz), 8.30 (t, 1 H, J=8.4 Hz), 7.21 (dd, 1 H, J=8.4 Hz, J=1.7 Hz), 7.11 (dd, 1 H, J=11.5 Hz, J=1.7 Hz), 6.72 (m, 1 H), 3.09 (d, 3 H, J=4.7 Hz), 2.61 (m, 1 H), 2.34 (m, 1 H), 2.10-1.09 (m, 14 H). $^{19}$FNMR (CDCl$_3$): −61.86, −110.54. LRMS [M+H]+ found: 560.31; calculated: 560.18.

Analytical data for compound I-27: 4-(3-(6-cyano-5-(trifluoromethyl)pyridin-3-yl)-4-oxo-2-thioxoimidazolidin-1-yl)-2-fluoro-N-methylbenzamide.

$^1$HNMR (CDCl$_3$): 9.03 (d, 1H, J=1.7 Hz), 8.28 (d, 1H, J=1.7 Hz), 8.25 (t, 1 H, J=8.4 Hz), 7.79 (dd, 1 H, J=8.4 Hz, J=1.6 Hz), 7.45 (dd, 1 H, J=10.7 Hz, J=1.3 Hz), 6.71 (m, 1 H), 4.75 (s, 1 H), 4.15 (d, 1H, J=6.7 Hz), 3.06 (d, 3 H, J=4.7 Hz). $^{19}$FNMR (CDCl$_3$): −61.97, −110.14. LRMS [M+H]+ found: 438.18; calculated: 438.06.

Analytical Data for Compound (+)-I-6:

$^1$HNMR (CDCl$_3$): 9.06 (d, 1H, J=1.7 Hz), 8.33 (d, 1H, J=1.7 Hz), 8.28 (t, 1 H, J=8.4 Hz), 7.11 (dd, 1 H, J=8.3 Hz, J=1.6 Hz), 7.00 (dd, 1 H, J=11.6 Hz, J=1.5 Hz), 6.72 (m, 1 H), 3.01 (d, 3 H, J=4.7 Hz), 2.16-2.03 (m, 3H), 1.77 (m, 2 H), 1.61-1.55 (m, 8 H), 1.40-1.29 (m, 4 H). $^{19}$FNMR (CDCl$_3$): −61.88, −110.70. LRMS [M+H]+ found: 574.26; calculated: 574.6.

Analytical data for compound (+)-I-18: 4-((7R)-3-(4-cyano-3-(trifluoromethyl)phenyl)-7-methyl-4-oxo-2-thioxo-1,3-diazaspiro[4.4]nonan-1-yl)-2-fluoro-N-methylbenzamide.

$^1$HNMR (CDCl$_3$): 8.23 (m, 1H), 7.90 (d, 1H, J=8.2 Hz), 7.75 (d, 1 H, J=8.2 Hz), 7.21 (m, 1H), 7.10 (m, 1 H), 6.72 (m, 1 H), 3.08 (d, 3 H, J=4.7 Hz), 2.45 (m, 3H), 2.36 (m, 1H), 2.28 (m, 1H), 2.04 (m, 1H), 1.58 (m, 1H), 1.45 (m 1H), 0.96 (d, 1H, J=6.1 Hz), 0.85 (d, 1H, J=6.1 Hz). $^{19}$FNMR (CDCl$_3$): −61.98, −110.59. LRMS [M+H]+ found: 505.30; calculated: 505.50.

Analytical data for compound (+)-I-19: 4-(3-(4-cyano-3-(trifluoromethyl)phenyl)-7-methyl-4-oxo-2-thioxo-1,3-diazaspiro[4.5]decan-1-yl)-2-fluoro-N-methylbenzamide.

$^1$HNMR (CDCl$_3$): 8.27 (t, 1 H, J=8.4 Hz), 7.97 (d, 1 H, J=8.3 Hz), 7.93 (d, 1 H, J=1.5 Hz), 7.82 (d, 1 H, J=1.5 Hz), 7.19 (d, 1 H, J=8.3 Hz), 7.09 (d, 1H, J=10 Hz), 6.73 (m, 1 H), 3.08 (d, 3 H, J=4.5 Hz), 2.6 (m, 1H), 2.11-2.04 (m, 2H), 1.77 (m, 2H), 1.63 (m, 2H), 1.26 (m, 2 H), 0.92 (d, 3H, 18.4 Hz). $^{19}$FNMR (CDCl$_3$): −61.96, −110.89. LRMS [M+H]+ found: 519.25; calculated: 519.53.

Analytical data for compound (+)-I-20: 4-((7R)-3-(4-cyano-3-(trifluoromethyl)phenyl)-7-methyl-4-oxo-2-thioxo-1,3-diazaspiro[4.5]decan-1-yl)-2-fluoro-N-methylbenzamide.

$^1$HNMR (CDCl$_3$): 8.27 (t, 1 H, J=8.4 Hz), 7.97 (d, 1 H, J=8.3 Hz), 7.92 (d, 1 H, J=1.4), 7.82 (d, 1 H, J=6.5 Hz), 7.19 (d, 1 H, J=8.3 Hz), 7.09 (d, 1H, J=10 Hz), 6.73 (m, 1 H), 3.08 (d, 3 H, J=4.5 Hz), 2.6 (m, 1H), 2.11-2.04 (m, 2H), 1.77 (m, 2H), 1.63 (m, 2H), 1.26 (m, 2H), 0.92 (d, 3H, 18.4 Hz). $^{19}$FNMR (CDCl$_3$): −61.96, −110.89. LRMS [M+H]+ found: 519.25; calculated: 519.53.

Analytical data for compound (+)-I-21: 4-(1'-(4-cyano-3-(trifluoromethyl)phenyl)-5'-oxo-2'-thioxospiro[bicyclo[3.2.0]hept[2]ene-6,4'-imidazolidin]-3'-yl)-2-fluoro-N-methylbenzamide.

$^1$HNMR (CDCl$_3$): 8.28 (t, 1 H, J=8.4 Hz), 7.90 (d, 1 H, J=8.4 Hz), 7.85 (d, 1 H, J=1.4), 7.72 (m, 1 H), 7.31 (d, 1 H, J=8.4 Hz), 7.22 (d, 1H, J=10 Hz), 6.66 (m, 1 H), 5.85 (m, 1H), 5.66 (m, 1H), 3.41 (m, 1H), 3.01 (d, 3 H, J=4.5 Hz), 2.94 (m, 1H), 2.76 (m, 1H), 2.58 (m, 1H), 2.53 (m, 2H). $^{19}$FNMR (CDCl$_3$): −62.00, −110.53. LRMS [M+H]+ found: 515.30; calculated: 515.49.

Analytical data for compound (+)-I-22: 4-((7R)-3-(6-cyano-5-(trifluoromethyl)pyridin-3-yl)-7-methyl-4-oxo-2-thioxo-1,3-diazaspiro[4.4]nonan-1-yl)-2-fluoro-N-methylbenzamide.

$^1$HNMR (CDCl$_3$): 9.08 (d, 1H, J=2.0 Hz), 8.34 (d, 1H, J=2.0 Hz), 8.31 (m, 1H), 7.28 (m, 1H), 7.17 (m, 1H), 6.71 (m, 1H), 3.08 (d, 3 H, J=4.7 Hz), 2.45 (m, 3H), 2.36 (m, 1H), 2.28 (m, 1H), 2.04 (m, 1H), 1.67 (m, 1H), 1.54 (m 1H), 1.04 (d, 1H, J=6.4 Hz), 0.93 (d, 1H, J=6.4 Hz). $^{19}$FNMR (CDCl$_3$): −61.87, −110.47. LRMS [M+H]+ found: 506.28; calculated: 506.49.

Analytical data for compound (+)-I-23: 4-(3-(6-cyano-5-(trifluoromethyl)pyridin-3-yl)-7-methyl-4-oxo-2-thioxo-1,3-diazaspiro[4.5]decan-1-yl)-2-fluoro-N-methylbenzamide.

$^1$HNMR (CDCl$_3$): 9.07 (d, 1H, J=2.0 Hz), 8.33 (d, 1H, J=2.0 Hz), 8.28 (t, 1H, J=8.4 Hz), 7.26 (d, 1H, J=3.4 Hz), 7.08 (d, 1H, J=1.7 Hz), 6.71 (m, 1H), 4.25 (bs, 1H), 3.08 (d, 3H, J=4.5 Hz), 2.6 (m, 1H), 2.11-2.04 (m, 2H), 1.77 (m, 2H), 1.63 (m, 2H), 1.26 (m, 2 H), 0.92 (d, 3H, 18.4 Hz). $^{19}$FNMR (CDCl$_3$): −61.86, −110.70. LRMS [M+H]+ found: 520.23; calculated: 520.51.

Analytical data for compound (+)-I-24: 4-((7R)-3-(6-cyano-5-(trifluoromethyl)pyridin-3-yl)-7-methyl-4-oxo-2-thioxo-1,3-diazaspiro[4.5]decan-1-yl)-2-fluoro-N-methylbenzamide.

$^1$HNMR (CDCl$_3$): 9.08 (d, 1H, J=2.0 Hz), 8.33 (d, 1H, J=2.0 Hz), 8.28 (t, 1H, J=8.4 Hz), 7.26 (d, 1H, J=3.4 Hz), 7.08 (d, 1H, J=1.7 Hz), 6.71 (m, 1H), 4.25 (bs, 1H), 3.08 (d, 3H, J=4.5 Hz), 2.6 (m, 1H), 2.11-2.04 (m, 2H), 1.77 (m, 2H), 1.63 (m, 2H), 1.26 (m, 2 H), 0.92 (d, 3H, 18.4 Hz). $^{19}$FNMR (CDCl$_3$): −61.86, −110.71. LRMS [M+H]+ found: 520.23; calculated: 520.51.

Analytical data for compound (+)-I-25: 4-(1'-(6-cyano-5-(trifluoromethyl)pyridin-3-yl)-5'-oxo-2'-thioxospiro[bicyclo[3.2.0]hept[2]ene-6,4'-imidazolidin]-3'-yl)-2-fluoro-N-methylbenzamide.

$^1$HNMR (CDCl$_3$): 9.08 (d, 1H, J=2.1 Hz), 8.33 (t, 1H, J=8.4 Hz), 8.31 (d, 1H, J=2.1 Hz), 7.38 (d, 1H, J=1.8 Hz), 7.29 (d, 1 H, J=9.8 Hz), 6.71 (m, 1H), 5.92 (m, 1 H), 5.74 (m, 1H), 3.50 (m, 1H), 3.08 (d, 3 H, J=4.7 Hz), 3.00 (m, 1H), 2.8 (m, 1H), 2.66-2.59 (m, 3 H). $^{19}$FNMR (CDCl$_3$): −61.89, −110.34. LRMS [M+H]+ found: 516.29; calculated: 516.51.

Analytical data for compound I-7: 4-(3-(6-cyano-5-(trifluoromethyl)pyridin-3-yl)-7,7,9,9-tetramethyl-4-oxo-2-thioxo-1,3-diazaspiro[4.5]decan-1-yl)-2-fluoro-N-methylbenzamide.

This compound was isolated as a beige foam. $^1$HNMR (CDCl$_3$): 8.9 (d, 1H, J=1.5 Hz), 8.24 (d, 1H, J=1.5 Hz), 8.22 (t, 1 H, J=8.4 Hz), 7.19 (dd, 1 H, J=8.3 Hz, J=1.6 Hz), 7.03 (dd, 1 H, J=11.6 Hz, J=1.5 Hz), 6.65 (m, 1 H), 3.01 (d, 3 H, J=4.7 Hz), 1.97 (d, 2H, J=14.4 Hz), 1.62 (d, 2H, J=14.4 Hz), 1.50 (s, 2 H), 1.17 (s, 6H), 0.83 (s, 6H). $^{19}$FNMR (CDCl$_3$): −61.89, −110.57. LRMS [M+H]+ found: 562.28; calculated: 562.59.

Additional compounds of formula I were prepared in a manner substantially similar to that described above.

Example 17

In Vitro GFP Reporter Assay

Compounds of the present invention were assayed in an in vitro GFP (green fluorescent protein) reporter assay, which can be used to determine the effect of compounds on AR transcriptional activity. LNCaP (prostate cancer) cells were engineered to express an AR-regulated GFP reporter (Pb.PSE.EGFP), such that GFP expression indicates AR transcriptional activity. A representative procedure for this assay follows.

LNCaP-Pb.PSE.EGFP cells overexpressing either wild-type AR (WT) or the F876L mutant AR (FL) were treated with vehicle (DMSO) or with either 1 uM or 10 uM of Enzalutamide or ARN509, or 10 uM of a compound of formula I. After 4 days the treated cells were subjected to flow cytometric analysis and the histogram overlays of GFP expression (FL1) were displayed Results of certain compounds are depicted (together with the geometric mean fluorescence intensity is indicated in the legends below the histogram) in each of FIGS. 1 through 15. In each of the figures, results for the assay using WT AR is on the left side graph and the F876L mutant AR is on the right side graph. FIG. 16 depicts tabulated results obtained for some of the test compounds. In some embodiments, a provided compound is considered to be a modulator of a tested AR if it results in similar effects on induced GFP expression as compared with a reference androgen or anti-androgen.

Example 18

AR Luciferase Reporter Assay

Compounds of the present invention were assayed in an in vitro AR luciferase reporter assay reporter assay, which can be used to determine the effect of compounds on AR transcriptional activity. CV1 cells were engineered to express an AR-regulated luciferase reporter, such that luciferase expression indicates AR transcriptional activity. A representative procedure for this assay follows.

CV1 cells ($10^6$ cells/10 cm plate) were cotransfected with 50 ng of SV40 *Renilla* Luciferase, 5 ug of ARE(4X)-Luciferase, and 10 ug of one pWZL-AR expression construct using Lipofectamine 2000 (Invitrogen). Transfection media was removed 4-6 hours later and replaced with phenol red free DME-HG containing 10% charcoal stripped serum. The following day each plate was split into 24- or 48-well plates, in 10% CSS media, containing the indicated drugs in triplicate. Twenty-four to forty-eight hours later, luciferase activity was assayed using Dual-Luciferase Reporter Assay System (Promega) on a 96-well luminometer (Turner Biosystems). In some embodiments, a provided compound is considered to be a modulator of a tested AR if it results in similar effects on induced expression of luciferase in the luciferase reporter assay as compared with a reference androgen or anti-androgen.

Example 19

In Vitro Cell Viability Assay

Compounds of the present invention were assayed in an in vitro cell viability assay, which can be used to determine the effect of compounds on LNCaP cell growth and survival. A representative procedure for this assay follows.

LNCaP-Pb.PSE-EGFP cells for flow cytometric analysis were treated with test compounds (1 uM or 10 uM) for 4-6 days, changing media and drug every 2-3 days. Cells were collected using Accumax dissociation solution (Innovative Cell Technologies) and dead cells were counterstained using TO-PRO3-Iodide (Invitrogen). EGFP expression was measured using the BD-FACSCalibur flow cytometer using the 488 nm laser and 530/30 bandpass filter to detect EGFP expression, and the 633 nm laser and 661/16 bandpass filter to detect TO-PRO3-Iodide labeled dead cells. For each sample, 2-5×104 cell events were collected and analysis was done using FlowJo software. FACS-sorting of LNCaP-Pb.PSE.E-GFP cells was performed on a BD FACSVantage cell sorter. EGFP expression was detected using the 488 nm laser and 530/30 bandpass filter, and DAPI-labeled dead cells were detected using the 355 nm laser and 450/50 bandpass filter. Results of an in vitro cell viability assay are depicted in FIG. 17. In some embodiments, a provided compound is considered to be a modulator of a tested AR if it results in similar effects on cell viability as compared with a reference androgen or anti-androgen.

Example 20

Compounds of the present invention were also assayed in an in vitro cell viability assay in CWR22PC cancer cells. A representative procedure follows. CWR22PC cells ectopically expressing wild-type AR or AR F876L, cultured in full-serum containing media, were treated with vehicle (DMSO) or 10 uM of enzalutamide or compound I-1. Cell-TiterGLO assay was performed on days 1, 4, and 7 to determine cell viability. Results of a cell viability assay in CWR22PC cells are depicted in FIG. 18. On the y-axis RLU means relative light units. More light scattered means more viable cells. In some embodiments, a provided compound is considered to be a modulator of a tested AR if it results in similar effects on cell viability as compared with a reference androgen or anti-androgen.

Example 21

Initial Models of AR-Antiandrogen Complex Structures

No structures have been solved experimentally for enzalutamide or ARN-509 in complex with AR (agonist or antagonist conformation). Therefore, 3D structures of antiandrogens were first built using the computer program Gaussview (version 4.1.2, part of the computer program Gaussian 03) and then geometrically optimized in a quantum mechanical force field at the level of restricted Hartree-Fock (RHF) 6-31g* using the program Gaussian 03. The partial atomic charges were derived from the optimized structures by Restrained ElectroStatic Potential (RESP) fitting to the RHF/6-31g* potentials. The other parameters modeling the antiandrogens were taken from the CHARMm22 force field after assigning CHARMm22 atom types to antiandrogens with an in-house program.

The initial AR-antiandrogen complex structures were then modeled with the molecular modeling program CHARMM5, 6. Starting with the atomic coordinates of AR WT and A ring of 51 in the template crystal structure (PDB accession code, 2AXA), the side chain of residue 761 were replaced with CHARMm22-parameterized side chain of a leucine in cases of AR F876L and a CH group on the A ring was replaced with a nitrogen in cases of ARN-509. The rest of each antiandrogen was "grown" from the A ring using the ideal, unbound structures solved by geometry optimization. Missing side chain atoms were built using standard CHARMm22 parameters and hydrogen atoms were added with the HBUILD module of CHARMM. All these newly-introduced atoms without 3D crystal coordinates treated flexible and the rest under harmonic constraints with the force constant of 100 Kcal/mol/$Å^2$, each AR-antiandrogen complex structure was energetically minimized with 1 round of 100-step steepest decent followed by 2 rounds of 100-step Adopted-Basis Newton-Raphson (ABNR) energy minimization. Harmonic constraints were reset at the beginning of each round of minimization. No nonbonded cutoff was used. Solvent effects were implicitly modeled in this stage with a distance-dependent dielectric constant.

Example 22

Molecular Dynamics Simulations

The all-atom MD simulations were performed with explicit solvent atoms using the program CHARMM (version 36a1). Each initial AR-antiandrogen model was first centered and overlaid with a 50 Å×50 Å×50 Å cube of approximately 47,000 equilibrated water molecules. Any water molecule whose oxygen atom was within 2.8 Å away from any non-hydrogen atom of AR or antiandrogen was removed. Proper amount of sodium and chloride ions were automatically added to achieve overall charge neutrality and physiological level of ion concentration (0.145 M). Their positions were optimized with 10 independent trajectories of randomly replacing water molecules and performing 50 steps of steepest decent and 125 steps of ABNR energy minimization.

The molecular system including AR, antiandrogen, waters, and ions was heated to 298 K and equilibrated with two rounds of 0.1-ns MD simulations under successively weaker harmonic constraints on AR or antiandrogen atoms. After the MD equilibration, three sets of random velocities were assigned to initiate three independent 10-ns MD productions. The MD equilibration and production were performed using the crystal form of rhombic dodecahedron (RHDO) and the canonical ensemble (NVT). A nonbonded cutoff of 10 Å, periodic boundary conditions in conjunction with Ewald summation method, the leapfrog Verlet integrator, and the Hoover thermostat for pressure and temperature were used. The timestep was set as 2 fs. Parallel jobs for MD simulations were run on a computer cluster of Intel Xeon X5650 series (2.66 GHz and 4 GB memory for each CPU).

Structural models were visualized in a molecular graphics program, UCSF Chimera. The default option used when aligning structures. Results of the molecular modeling experiments are depicted in FIGS. 19 through 23. In some embodiments, the AR modulator, agonist or antagonist, as described herein, is one dimensioned to fit within the pocket defined by the computational model described above.

Example 23

Ligand Binding Assay

The relative binding affinity of DHT and AR antagonists in LNCaP cells ectopically expressing AR WT or AR F876L was determined using a competition assay in which increasing concentrations of cold competitor are added to cells preincubated with 18F-FDHT. The cells were propagated in RPMI media supplemented with 10% CSS (charcoal-stripped, dextran-treated fetal bovine serum). Cells were trypsinized, washed in PBS, and triplicate cell samples were mixed with 20,000 cpm 18F-FDHT and increasing amounts of cold competitor (0.1 nM to 10 uM). The solutions were shaken on an orbital shaker at ambient temperature, and after 1 hour the cells were isolated and washed with ice-cold Tris-buffered saline using a Brandel cell harvester (Gaithersburg, Md.). All the isolated cell samples were counted using a scintillation counter, with appropriate standards of total activity and blank controls, and the specific uptake of $^{18}$F-FDHT determined. These data were plotted against the concentration of the cold competitor to give sigmoidal displacement curves. The $IC_{50}$ values were determined using a one site model and a least squares curve fitting routine (Origin, OriginLab, Northampton, Mass.) with the $R^2$ of the curve fit being >0.99.

These data show that DHT binds to both AR WT and AR F876L expressing cells at a comparable IC50. However, MDV3100 is able to displace $^{18}$F-FDHT from the mutant AR F876L cells at a lower IC50 than for AR WT cells, suggesting a higher binding affinity of MDV3100 to the AR F876L mutant. These data are in line with previous data that showed the mutant AR T877A, which confers agonism on the antiandrogen hydroxyflutamide, binds to hydroxyflutamide (and several other hormones) with a higher affinity than to AR WT. (Ozers, et al. "The androgen receptor T877A mutant recruits LXXLL and FXXLF peptides differently than wild-type androgen receptor in a time-resolved fluorescence resonance energy transfer assay." Biochemistry (2007) 46, 683).

In some embodiments, a provided compound is considered to be a modulator, agonist or antagonist of a tested AR if it displaces $^{18}$F-FDHT from an AR.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula IV:

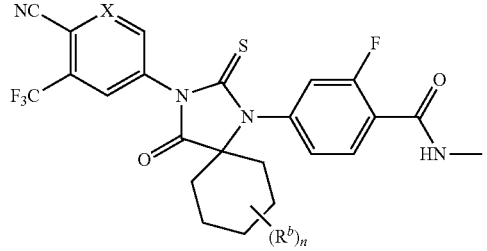

or a pharmaceutically acceptable salt thereof, wherein:

X is CH or N;

each $R^b$ is independently a substituted or unsubstituted $C_{1-6}$ aliphatic; and n is 0 to 4.

2. The compound according to claim 1, wherein the compound is:

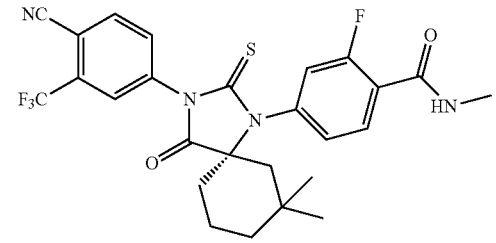

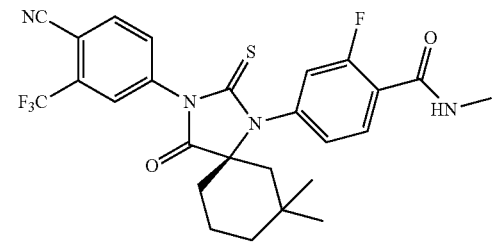

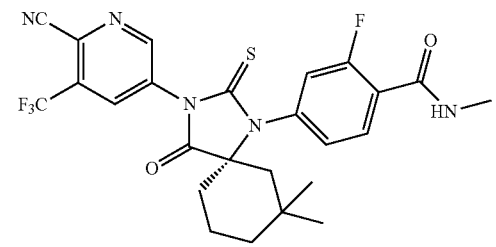

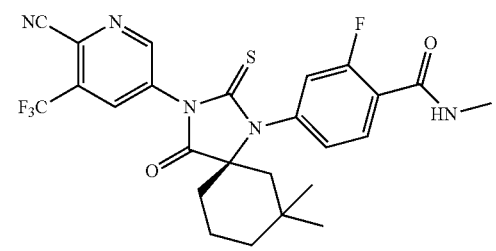

-continued
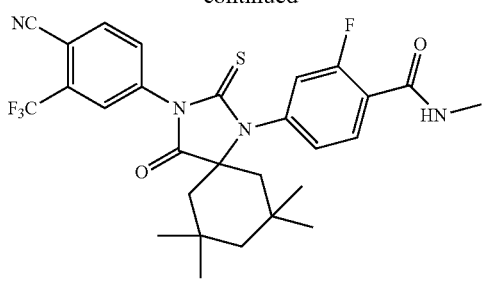
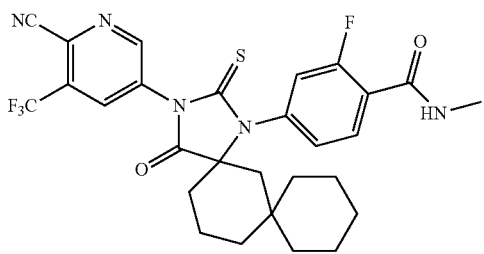
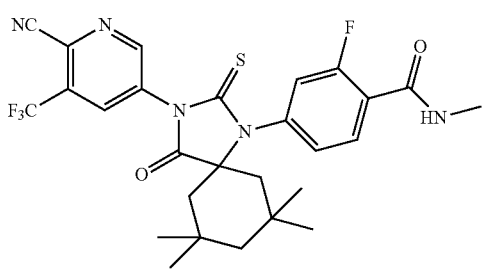
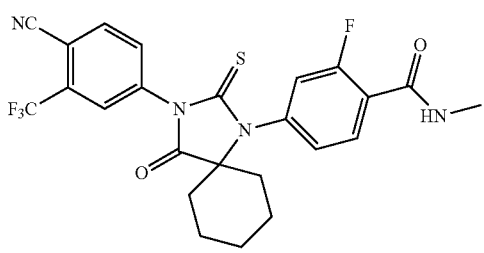
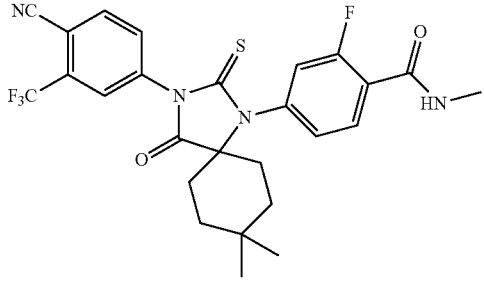
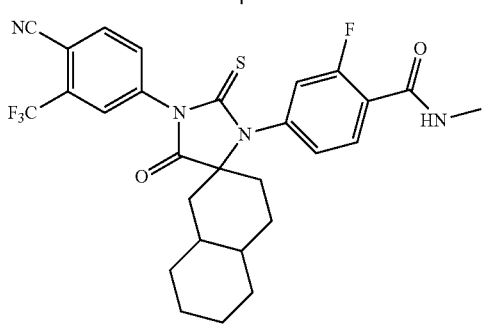
-continued
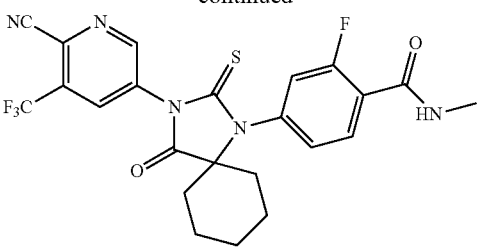
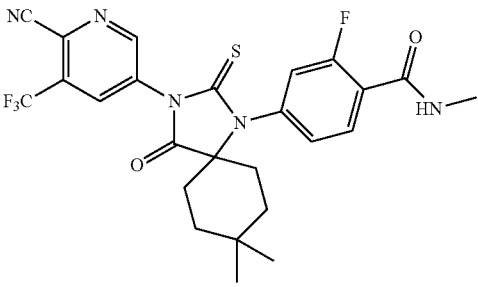
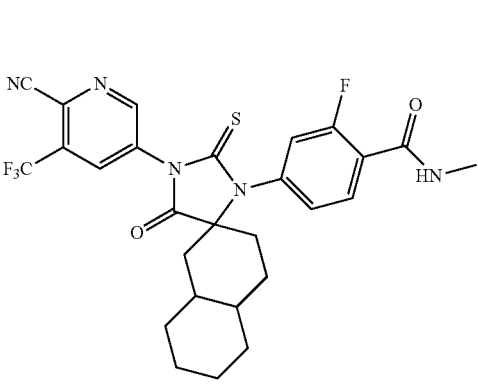
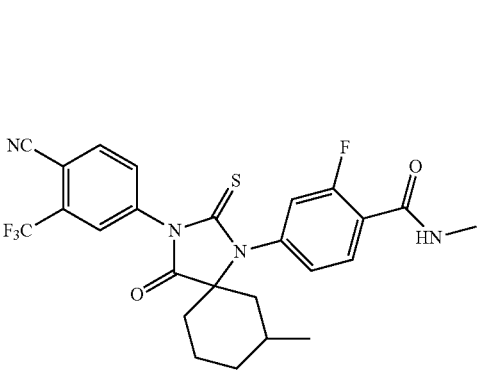
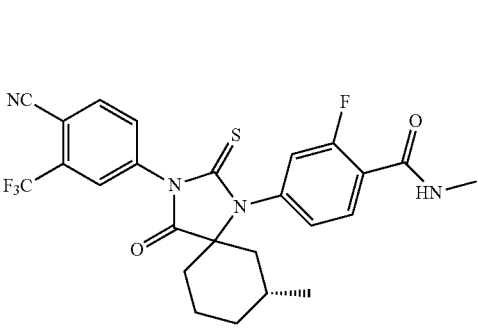

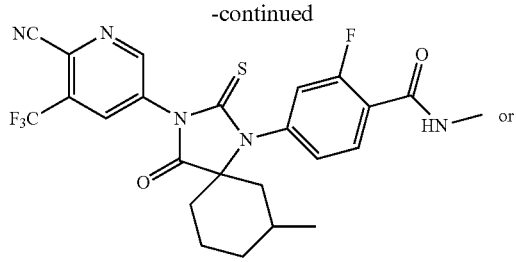

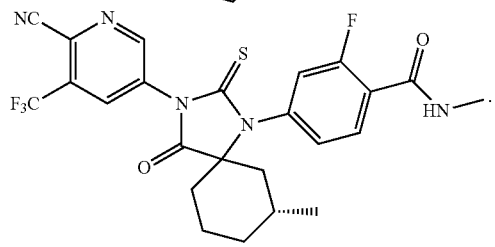 or

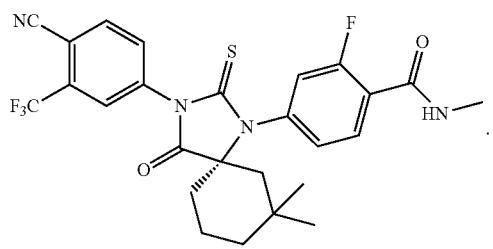 [SMILES: CNC(=O)c1ccc(N2C(=S)N(c3ccc(C#N)c(C(F)(F)F)c3)C(=O)[C@@]23CCCC(C)(C)C3)cc1F]

5. The compound of claim 1, wherein the compound is represented by the following structural formula:

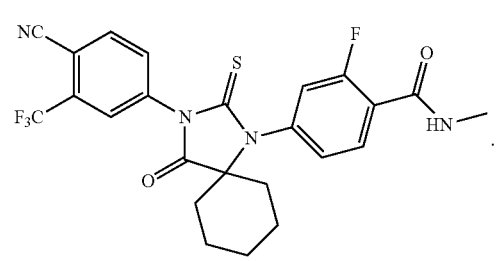 [SMILES: CNC(=O)c1ccc(N2C(=S)N(c3ccc(C#N)c(C(F)(F)F)c3)C(=O)C23CCCCC3)cc1F]

3. A pharmaceutical composition comprising a compound according to claim 1, or a pharmaceutically acceptable salt thereof, and a pharmaceutically acceptable carrier, adjuvant, or vehicle.

4. The compound of claim 1, wherein the compound is represented by the following structural formula:

* * * * *